United States Patent
Kudo et al.

(10) Patent No.: US 11,618,740 B2
(45) Date of Patent: Apr. 4, 2023

(54) COMPOUND, MATERIAL FOR ORGANIC ELECTROLUMINESCENCE DEVICES, ORGANIC ELECTROLUMINESCENCE DEVICE, AND ELECTRONIC DEVICE

(71) Applicant: IDEMITSU KOSAN CO., LTD., Chiyoda-ku (JP)

(72) Inventors: Yu Kudo, Sodegaura (JP); Tasuku Haketa, Sodegaura (JP); Hirokatsu Ito, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 188 days.

(21) Appl. No.: 16/864,185

(22) Filed: May 1, 2020

(65) Prior Publication Data
US 2020/0290985 A1   Sep. 17, 2020

Related U.S. Application Data

(63) Continuation of application No. PCT/JP2020/009500, filed on Mar. 5, 2020.

(30) Foreign Application Priority Data

Mar. 15, 2019 (JP) .............................. JP2019-049104

(51) Int. Cl.
 *C07C 211/61* (2006.01)
 *C07D 307/91* (2006.01)
 (Continued)

(52) U.S. Cl.
 CPC .......... *C07D 307/91* (2013.01); *H01L 51/006* (2013.01); *H01L 51/0073* (2013.01); *H01L 51/5024* (2013.01); *H01L 51/5056* (2013.01)

(58) Field of Classification Search
 CPC .. C07D 307/91; C07D 209/86; C07D 403/10; C09K 2211/1092; C09K 2211/1011;
 (Continued)

(56) References Cited

U.S. PATENT DOCUMENTS 9,087,997 B2 * 7/2015 Yabunouchi .......... H01L 51/006
10,693,079 B2 * 6/2020 Miyake .................. C09K 11/06
(Continued)

FOREIGN PATENT DOCUMENTS

| CN | 101432272 | 5/2009 |
|---|---|---|
| CN | 102046613 | 5/2011 |

(Continued)

OTHER PUBLICATIONS

Machine Translation of JP2016-103639 A (Itoi et al ) (Jun. 2, 2016). (Year: 2016).*
(Continued)

*Primary Examiner* — Caridad Everhart
(74) *Attorney, Agent, or Firm* — Oblon, McClelland, Maier & Neustadt, L.L.P.

(57) ABSTRACT

A compound represented by formula (A):

(A)

(Continued)

wherein Ar, $R^1$ to $R^7$, $R^{11}$ to $R^{14}$, $R^{21}$ to $R^{24}$, $R^{31}$ to $R^{34}$, *1, and $R^{41}$ to $R^{48}$ are as defined in the description provides organic electroluminescence devices with improved device performance.

15 Claims, 1 Drawing Sheet

(51) Int. Cl.
*H01L 51/00* (2006.01)
*H01L 51/50* (2006.01)

(58) Field of Classification Search
CPC ... C09K 11/06; C09K 11/025; H01L 51/0073; Y10S 428/917
See application file for complete search history.

(56) References Cited

U.S. PATENT DOCUMENTS

| | | | |
|---|---|---|---|
| 10,811,612 B2 | 10/2020 | Nakano et al. | |
| 2009/0284140 A1* | 11/2009 | Osaka | C09K 11/06 313/504 |
| 2011/0071317 A1* | 3/2011 | Osaka | C07D 209/86 564/308 |
| 2014/0217335 A1* | 8/2014 | Tanabe | C07D 307/91 252/519.21 |
| 2016/0118597 A1* | 4/2016 | Itoi | C07D 307/91 257/40 |
| 2016/0172593 A1* | 6/2016 | Takada | H01L 51/0074 257/40 |
| 2016/0240783 A1 | 8/2016 | Yen et al. | |
| 2016/0322578 A1* | 11/2016 | Hwang | H01L 51/006 |
| 2016/0372677 A1* | 12/2016 | Miyake | H01L 51/0058 |
| 2017/0012204 A1* | 1/2017 | Jin | H01L 51/0072 |
| 2017/0170402 A1* | 6/2017 | Itoi | C09K 11/06 |
| 2017/0179401 A1* | 6/2017 | Kim | H01L 51/0067 |
| 2020/0317653 A1 | 10/2020 | Ito et al. | |
| 2021/0384430 A1 | 12/2021 | Nakano et al. | |
| 2022/0045272 A1 | 2/2022 | Haketa et al. | |
| 2022/0059775 A1 | 2/2022 | Nakano et al. | |
| 2022/0069232 A1 | 3/2022 | Haketa et al. | |
| 2022/0158101 A1* | 5/2022 | Montenegro | C07D 405/10 |

FOREIGN PATENT DOCUMENTS

| | | | | |
|---|---|---|---|---|
| CN | 105541790 | | 5/2016 | |
| EP | 2 295 421 | | 3/2011 | |
| EP | 3 680 948 A2 | | 7/2020 | |
| JP | 2016103639 A | * | 6/2016 | ........... H01L 51/006 |
| KR | 10-2017-0094665 A | | 8/2017 | |
| KR | 10-2019-0020514 A | | 3/2019 | |
| WO | WO 2007/125714 A1 | | 11/2007 | |
| WO | WO 2009/145016 A1 | | 12/2009 | |
| WO | WO 2014/034793 A1 | | 3/2014 | |
| WO | WO 2019/088517 A1 | | 5/2019 | |
| WO | WO 2019/146781 A1 | | 8/2019 | |
| WO | WO 2020/075758 A1 | | 4/2020 | |
| WO | WO 2020/075759 A1 | | 4/2020 | |
| WO | WO 2020/075760 A1 | | 4/2020 | |
| WO | WO 2020/080416 A1 | | 4/2020 | |
| WO | WO 2020/080417 A1 | | 4/2020 | |
| WO | WO 2020/095998 A1 | | 5/2020 | |
| WO | WO 2020/096001 A1 | | 5/2020 | |
| WO | WO 2020/096012 A1 | | 5/2020 | |
| WO | WO 2020/096021 A1 | | 5/2020 | |
| WO | WO 2020/111253 A1 | | 6/2020 | |
| WO | WO 2020/115933 A1 | | 6/2020 | |
| WO | WO 2020/116418 A1 | | 6/2020 | |
| WO | WO 2020/116561 A1 | | 6/2020 | |
| WO | WO 2020/116562 A1 | | 6/2020 | |

OTHER PUBLICATIONS

International Search Report dated Jun. 2, 2020, in PCT Application No. PCT/JP2020/009500.

Supplementary European Search Report in corresponding European patent Application No. 20725613.2, dated Oct. 12, 2022 (Reference 15 is cited therein).

Office Action dated Dec. 28. 2052 in Chinese Patent Application No. 202080000925.X.

* cited by examiner

COMPOUND, MATERIAL FOR ORGANIC ELECTROLUMINESCENCE DEVICES, ORGANIC ELECTROLUMINESCENCE DEVICE, AND ELECTRONIC DEVICE

CROSS-REFERENCE TO RELATED APPLICATIONS

The present application is a continuation application of International Application No. PCT/JP2018/029217, filed Aug. 3, 2018, which claims priority to Japanese Patent Application No. 2017-151141, filed Aug. 3, 2017. The contents of these applications are incorporated herein by reference in their entirety.

TECHNICAL FIELD

The present invention relates to compounds, materials for organic electroluminescence devices, organic electroluminescence devices, and electronic devices comprising the organic electroluminescence devices.

BACKGROUND ART

An organic electroluminescence device ("organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for obtaining an organic EL device with a high efficiency to develop a compound that transports electrons or holes into the light emitting region efficiently and facilitates the recombination of electrons and holes.

Patent Literature 1 describes an aromatic amine derivative, wherein the nitrogen atom has a group comprising a dibenzofuran structure, a group comprising a terphenyl structure, and an aryl group. In the working examples, the aromatic amine derivative is used in a hole transporting layer.

Patent Literature 2 describes an aromatic amine derivative having at least one group comprising a dibenzofuran structure and an aryl group on the nitrogen atom. In the working examples, the aromatic amine derivative is used in a hole transporting layer.

CITATION LIST

Patent Literature

Patent Literature 1: WO 2009/145016
Patent Literature 2: WO 2007/125714

SUMMARY OF INVENTION

Technical Problem

Various compounds for organic EL devices have been reported. However, compounds that further improve the performance of organic EL devices have been still demanded.

The present invention has been made to solve the above problem and an object of the invention is to provide compounds further improving the performance of organic EL devices, organic EL devices having their performance further improved, and electronic devices comprising such organic EL devices.

Solution to Problem

The inventors have extensively studied organic EL devices comprising the compounds described in Patent Literatures 1 and 2. As a result thereof, the inventors have found that, as evident from the comparison between Examples 1 to 5 with Comparative Examples 1 to 4 described below, a monoamine compound wherein the central nitrogen atom has three substituents in a specific combination not described in Patent Literatures 1 and 2 provides an organic EL device having high efficiencies.

In an aspect, the present invention provides a compound represented by formula (A) (hereinafter also referred to as "inventive compound"):

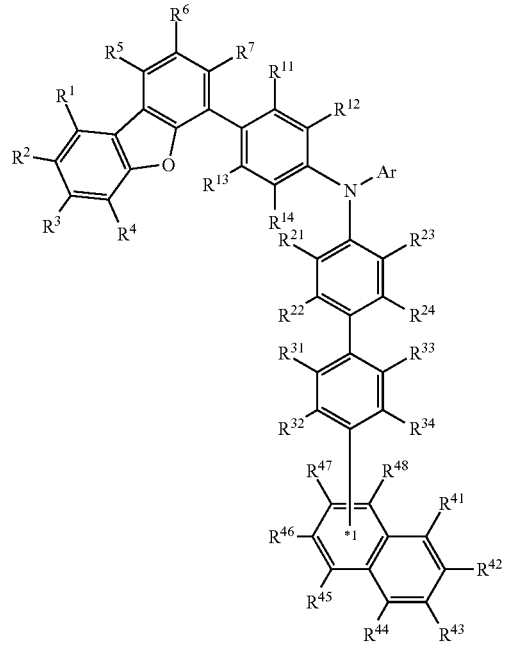

(A)

wherein:
Ar is a substituted or unsubstituted phenyl group, a substituted or unsubstituted biphenylyl group, a substituted or unsubstituted naphthyl group, or a substituted or unsubstituted phenanthryl group;
$R^1$ to $R^7$ are each independently a hydrogen atom, a halogen atom, an alkyl group having 1 to 10 carbon atoms, or a cycloalkyl group having 3 to 6 ring carbon atoms;
$R^{11}$ to $R^{14}$ are each independently a hydrogen atom, a halogen atom, an alkyl group having 1 to 10 carbon atoms, a cycloalkyl group having 3 to 6 ring carbon atoms;
$R^{21}$ to $R^{24}$ are each independently a hydrogen atom, a halogen atom, an alkyl group having 1 to 10 carbon atoms, or a cycloalkyl group having 3 to 6 ring carbon atoms;
$R^{31}$ to $R^{34}$ are each independently a hydrogen atom, a halogen atom, an alkyl group having 1 to 10 carbon atoms, or a cycloalkyl group having 3 to 6 ring carbon atoms;
$R^{41}$ to $R^{48}$ are each independently a hydrogen atom, a halogen atom, an alkyl group having 1 to 10 carbon atoms, or a cycloalkyl group having 3 to 6 ring carbon atoms, provided that one of $R^{47}$ and $R^{48}$ is a single bond bonded to *1;

the optional substituent for the phenyl group, the biphenylyl group, the naphthyl group, and the phenanthryl group is independently a halogen atom, an alkyl group having 1 to 10 carbon atoms, or a cycloalkyl group having 3 to 6 ring carbon atoms;

adjacent two selected from $R^1$ to $R^7$, $R^{11}$ to $R^{14}$, $R^{21}$ to $R^{24}$, $R^{31}$ to $R^{34}$, and $R^{41}$ to $R^{48}$ not the single bond bonded to *1 are not bonded to each other thereby failing to form a ring structure; and if the phenyl group, the biphenylyl group, the naphthyl group, or the phenanthryl group has adjacent two optional substituents, the adjacent two optional substituents are not bonded to each other thereby failing to form a ring structure.

In another aspect, the present invention provides a material for organic EL device comprising the inventive compound.

In another aspect, the present invention provides an organic electroluminescence device comprising an anode, a cathode, and an organic layer disposed between the anode and the cathode, wherein the organic layer comprises a light emitting layer and at least one layer of the organic layer comprises the inventive compounds.

In another aspect, the present invention provides an electronic device comprising the organic electroluminescence device.

Advantageous Effects of Invention

The organic EL device comprising the inventive compound exhibits a high efficiency.

DESCRIPTION OF EMBODIMENTS

Figure 1:
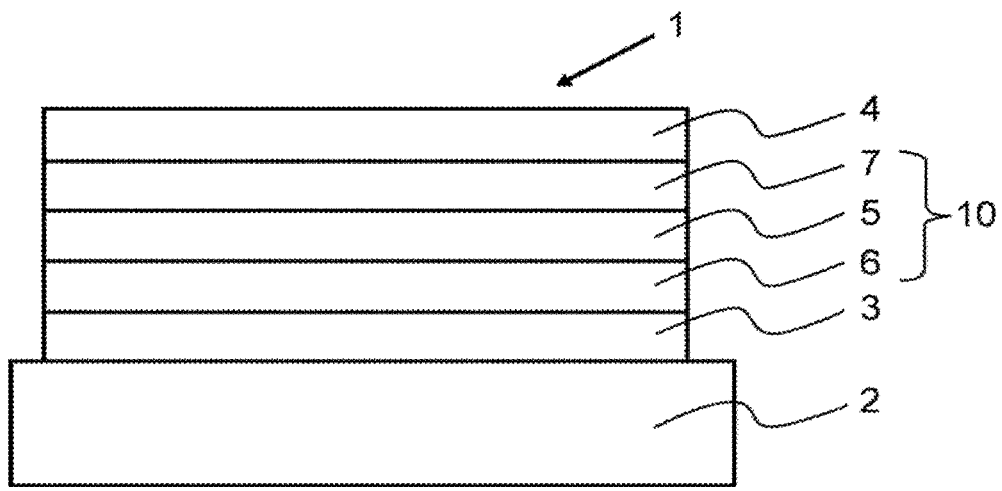
FIG. 1 is a schematic view showing the layered structure of an organic EL device in an embodiment of the invention.

The definition of "hydrogen atom" used herein includes isotopes different in the neutron numbers, i.e., light hydrogen (protium), heavy hydrogen (deuterium), and tritium.

The number of ring carbon atoms referred to herein means the number of the carbon atoms included in the atoms that form the ring itself of a compound in which a series of atoms are bonded to form a cyclic compound (for example, a monocyclic compound, a fused ring compound, a cross-linked compound, a carbocyclic compound, and a heterocyclic compound) and a compound in which two or more cyclic compounds are directly bonded (ring assembly compound). If the ring has a substituent, the carbon atom in the substituent is not included in the ring carbon atom. Unless otherwise noted, the same applies to the number of ring carbon atoms mentioned below.

For example, a benzene ring has 6 ring carbon atoms, a naphthalene ring has 10 ring carbon atoms, a pyridinyl group has 5 ring carbon atoms, a furan ring has 4 ring carbon atoms, 9,9-diphenylfluorenyl group has 13 ring carbon atoms, and a 9,9'-spirobifluorenyl group has 25 ring carbon atoms.

If a benzene ring has, for example, an alkyl substituent, the carbon atom in the alkyl substituent is not counted as the ring carbon atom of the benzene ring. Therefore, an alkyl-substituted benzene ring has 6 ring carbon atoms. If a naphthalene ring has, for example, an alkyl substituent, the carbon atom in the alkyl substituent is not counted as the ring carbon atom of the naphthalene ring. Therefore, an alkyl-substituted naphthalene ring has 10 ring carbon atoms.

The number of ring atom referred to herein means the number of the atoms that form the ring itself of the cyclic compounds and the ring assembly compounds mentioned above. The hydrogen atom bonded to the ring atom and the atom in the substituent bonded to the ring atom are not counted as the ring atom. Unless otherwise noted, the same applies to the number of ring atoms mentioned below.

For example, a pyridine ring has 6 ring atoms, a quinazoline ring has 10 ring atoms, and a furan ring has 5 ring atoms. The hydrogen atom and the atom in a substituent bonded to a pyridine ring are not counted as the ring atom. Therefore, a substituted pyridine ring has 6 ring atoms. The hydrogen atom and the atom in a substituent bonded to a quinazoline ring are not counted as the ring atom. Therefore, a substituted quinazoline ring has 10 ring atoms.

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The term of "substituted group ZZ" referred to by "substituted or unsubstituted group ZZ" used herein means that at least one hydrogen atom in the group ZZ is substituted by a substituent. The term "group BB substituted by group AA" means that at least one hydrogen atom in the group BB is substituted by the group AA.

The compound of the invention will be described below.
The inventive compound is represented by formula (A):

(A)

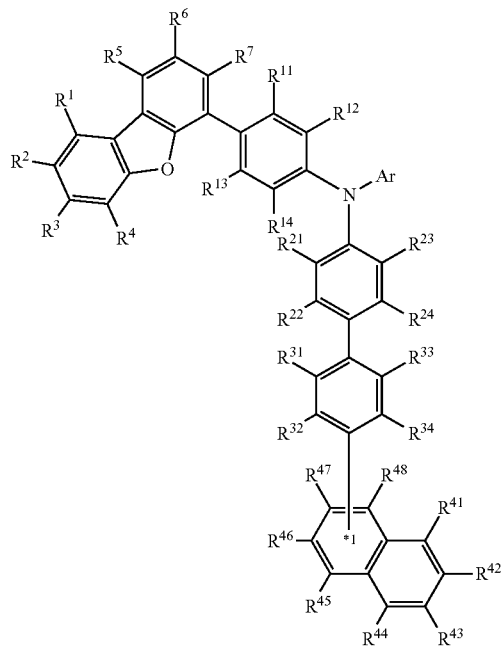

The inventive compound includes a compound represented by formula (1) or (11), preferably formula (1):
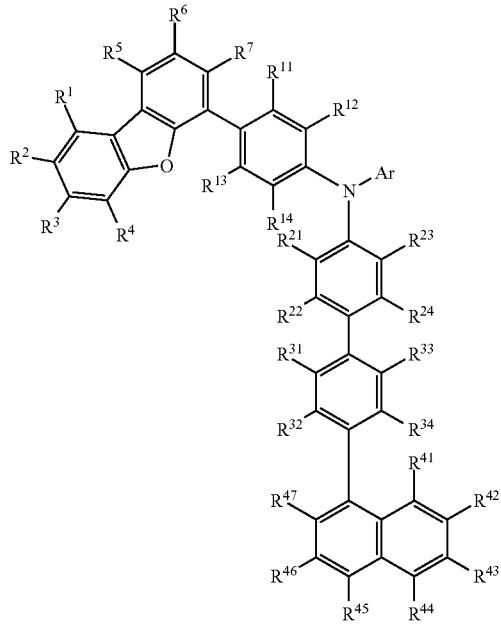
(1)
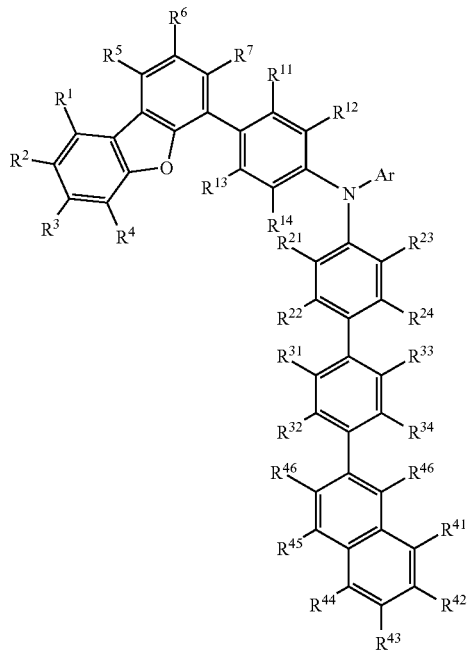
(11)
The inventive compound is preferably represented by any of formulae (2) to (5), more preferably represented by any of formulae (2) to (4):
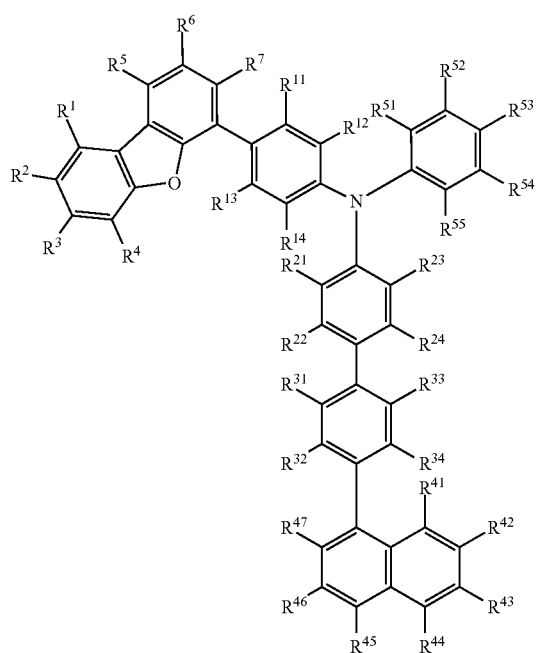
(2)

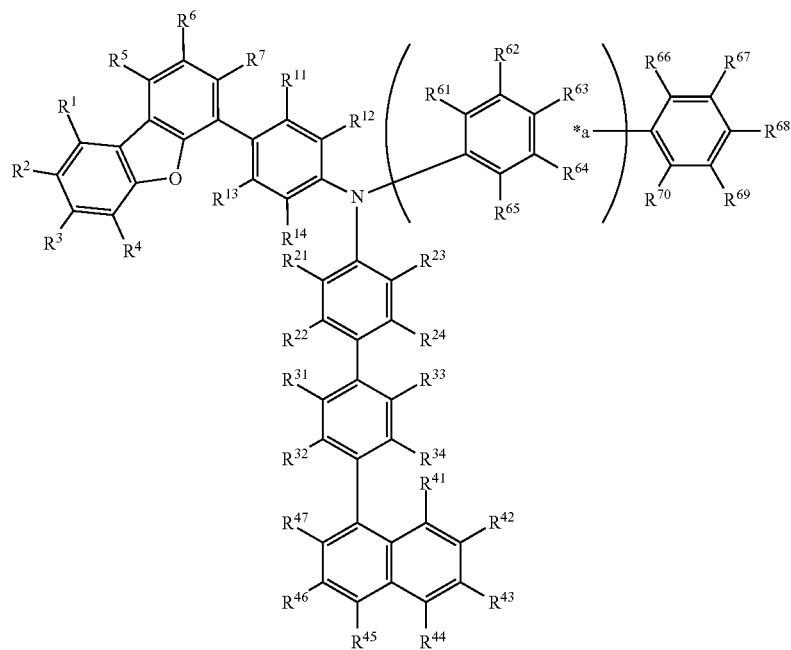
(3)
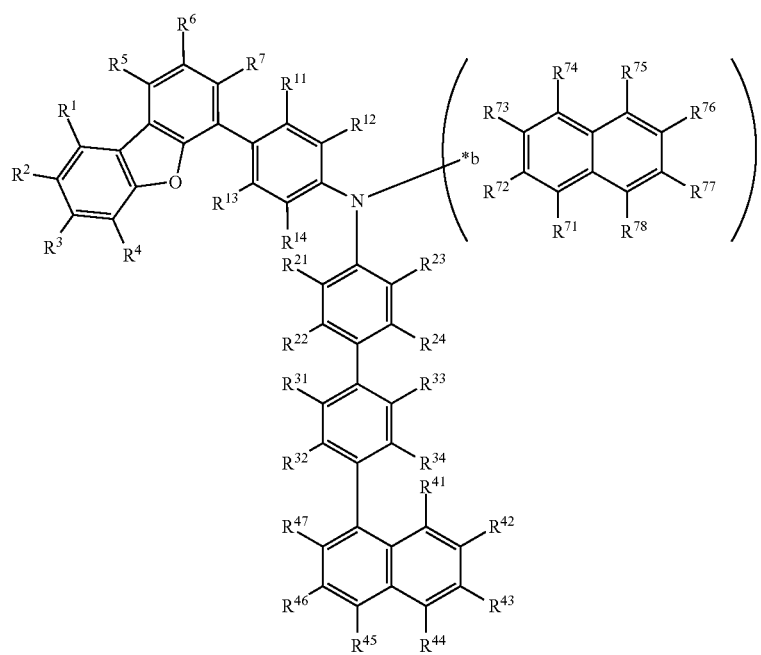
(4)

-continued
(5)
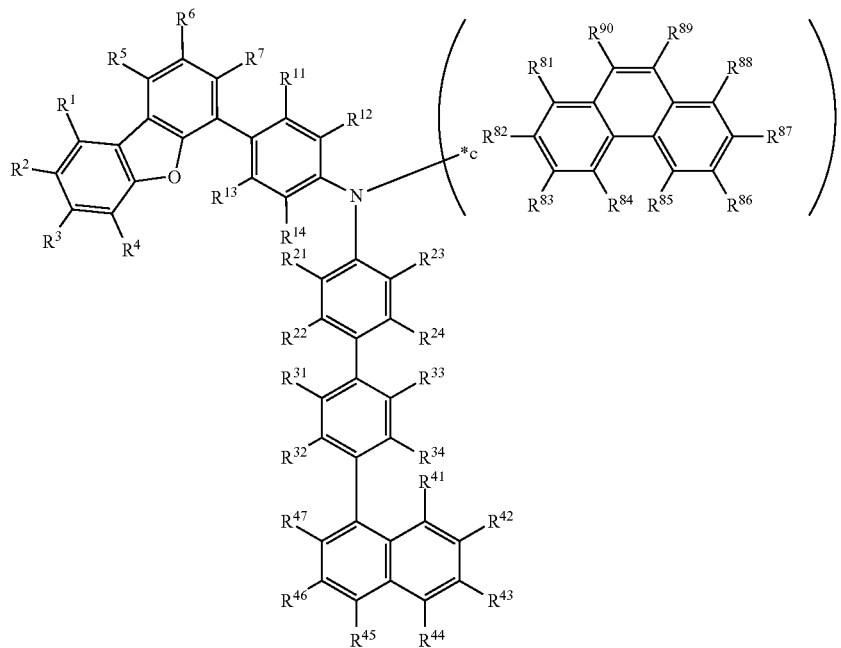
In an embodiment, the inventive compound is preferably represented by any of formulae (12) to (15), more preferably represented by any of formulae (12) to (14):
(12)
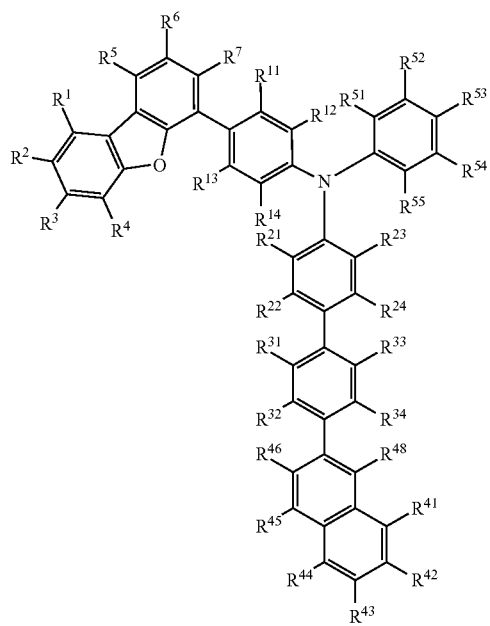

(13)
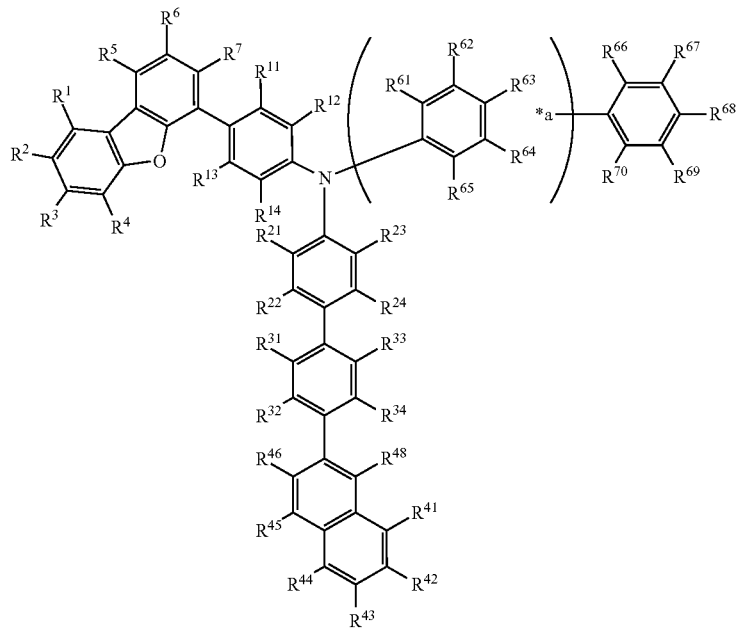
(14)
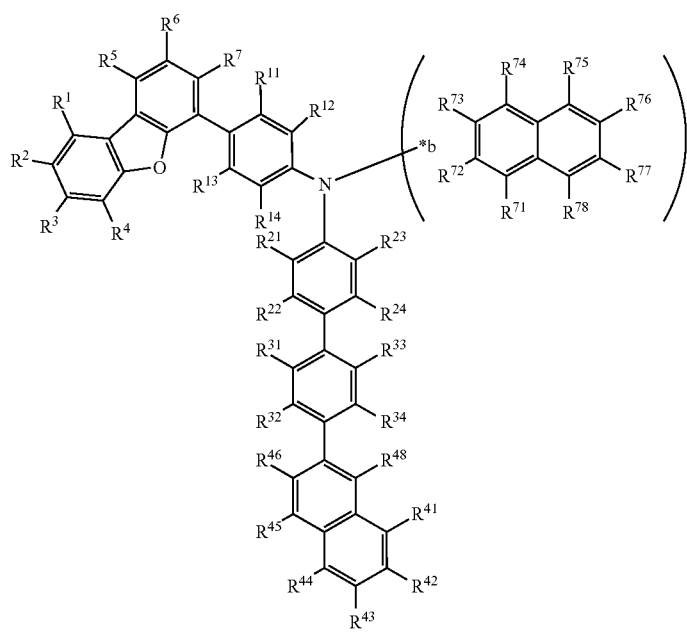

-continued
(15)
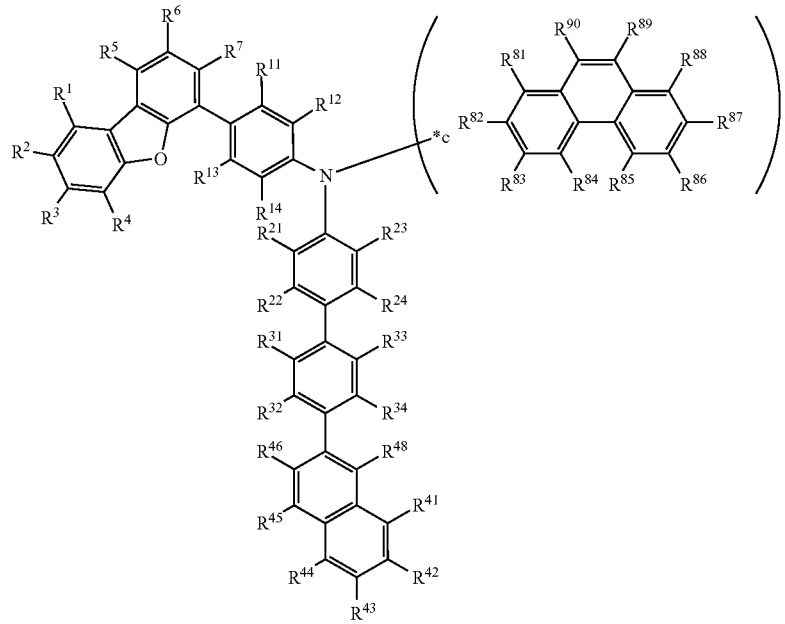
Formula (3) is represented by any of formulae (3a) to (3c), preferably represented by formula (3a) or (3c):
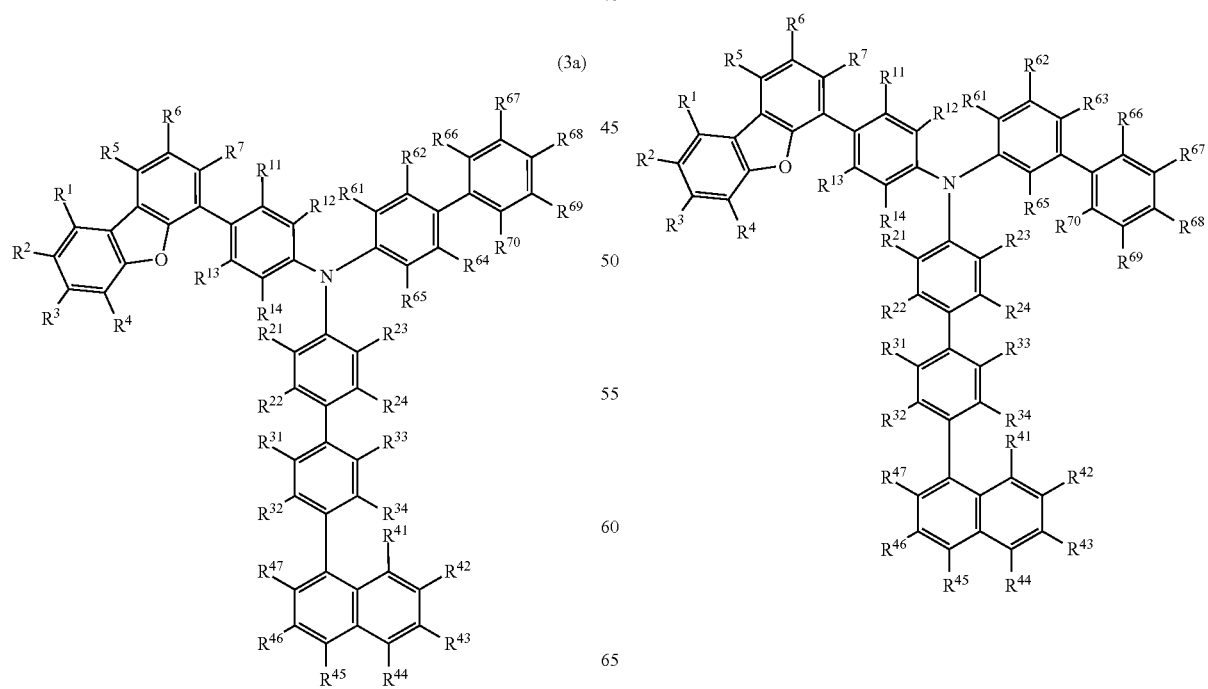

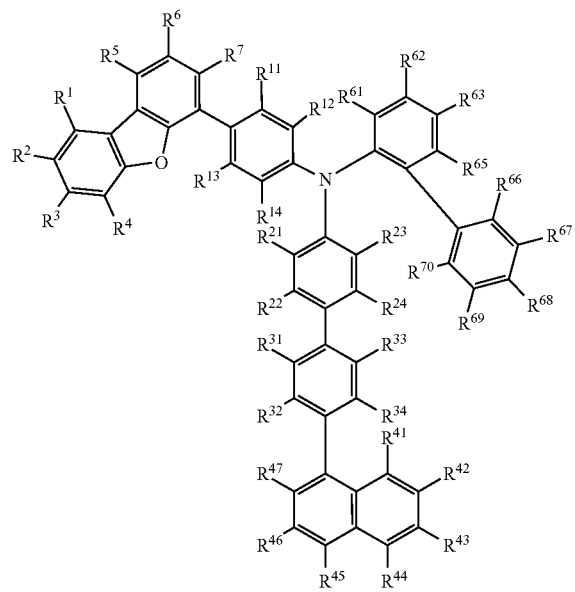
(3c)
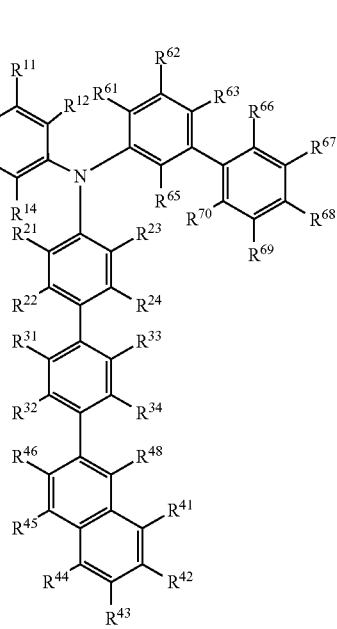
(13b)
Formula (13) is represented by any of formulae (13a) to (13c), preferably represented by formula (13a) or (13c):
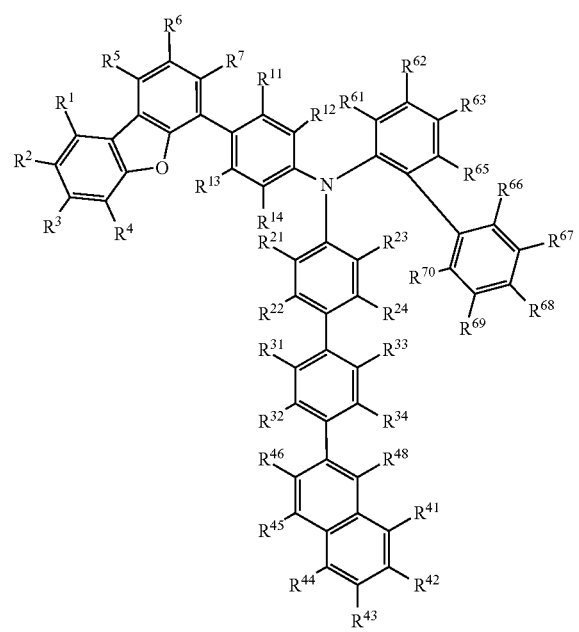
(13a)
(13c)
Formula (4) is represented by formula (4a) or (4b), preferably represented by formula (4a):

(4a)
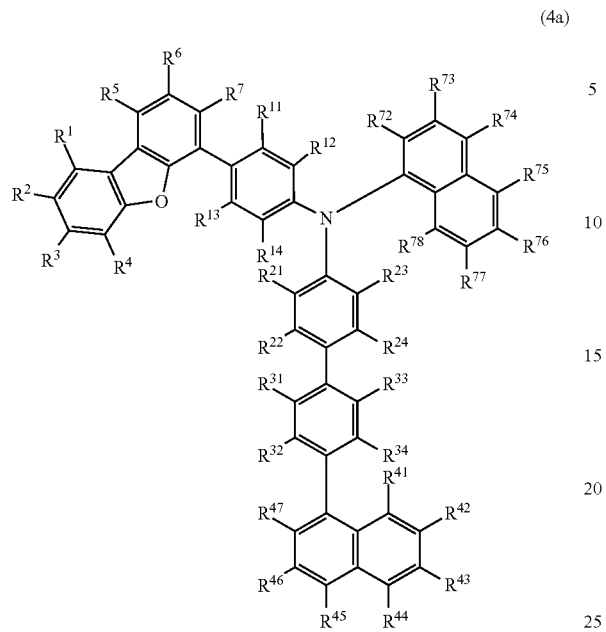
(14a)
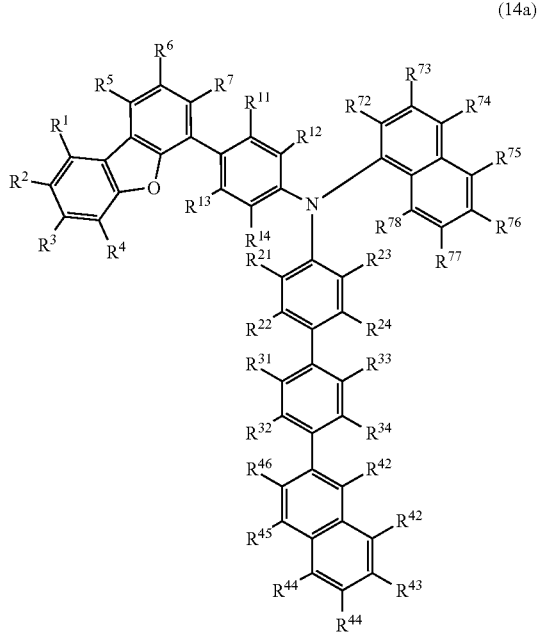
(4b)
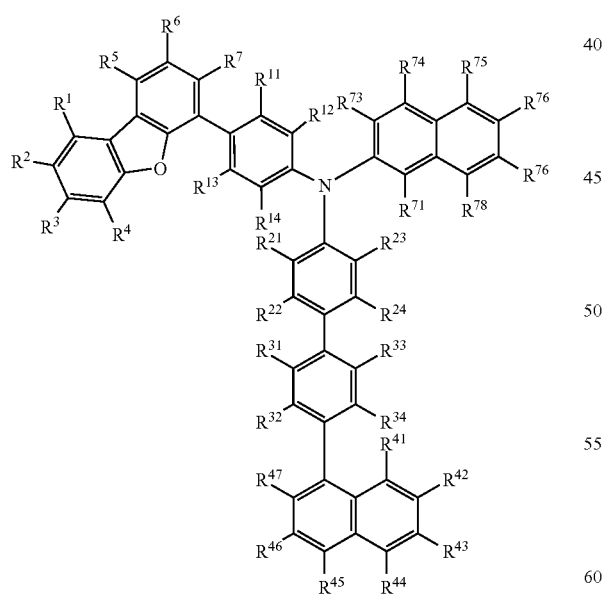
(14b)
Formula (14) is represented by formula (14a) or (14b), preferably represented by formula (14a):
Formula (5) is represented by any of formulae (5a) to (5e), preferably represented by formula (5b) or (5e):

(5a)
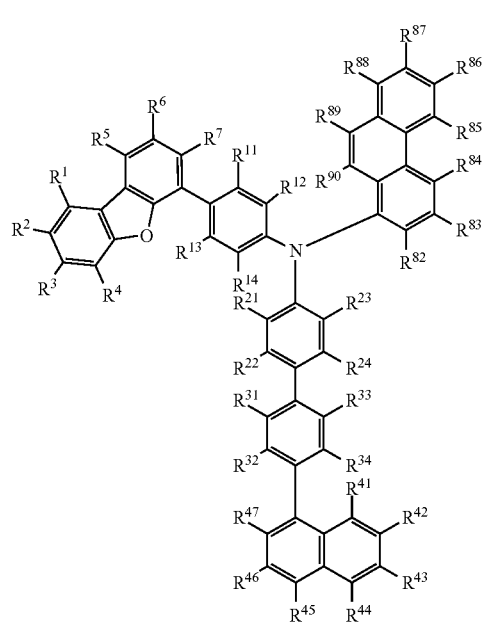
(5c)
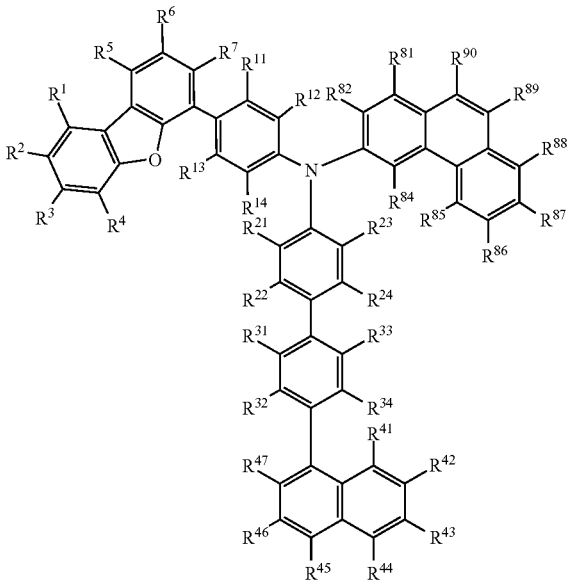
(5b)
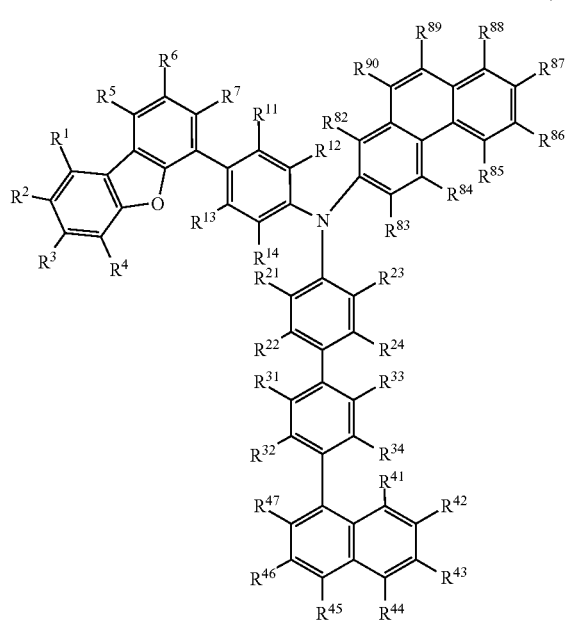
(5d)
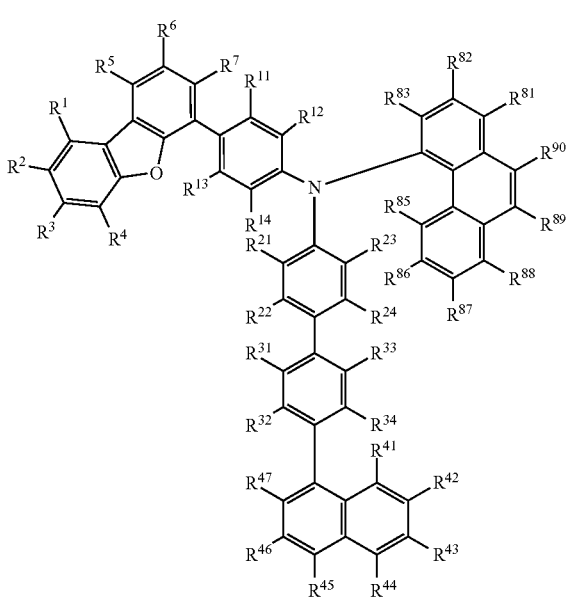

(5e)
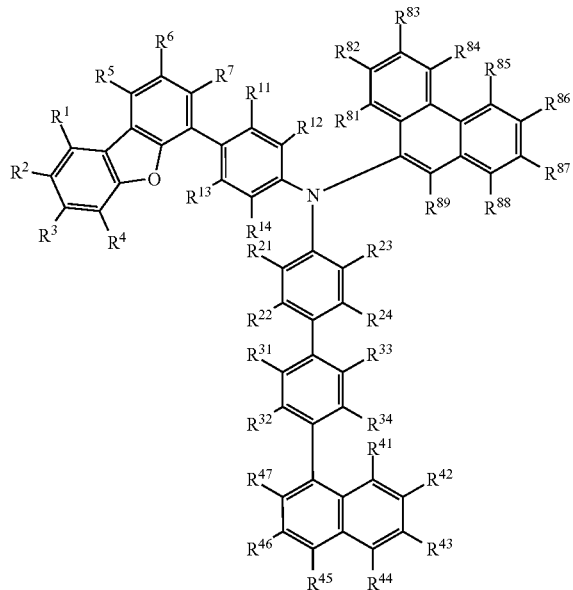
(15b)
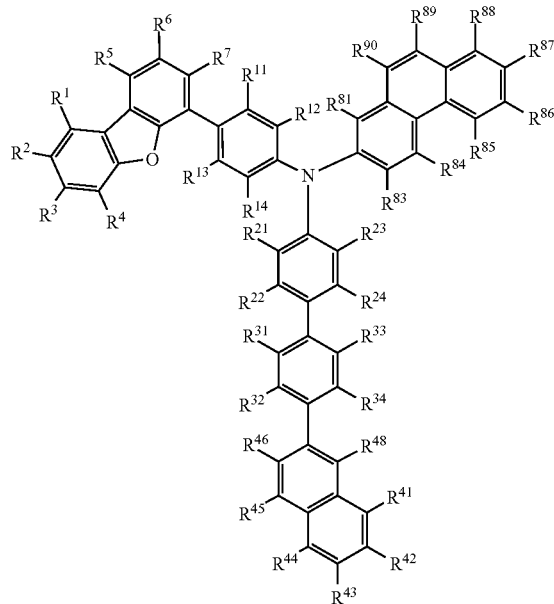
Formula (15) is represented by any of formulae (15a) to (15e), preferably represented by formula (5b) or (5e):
(15a)
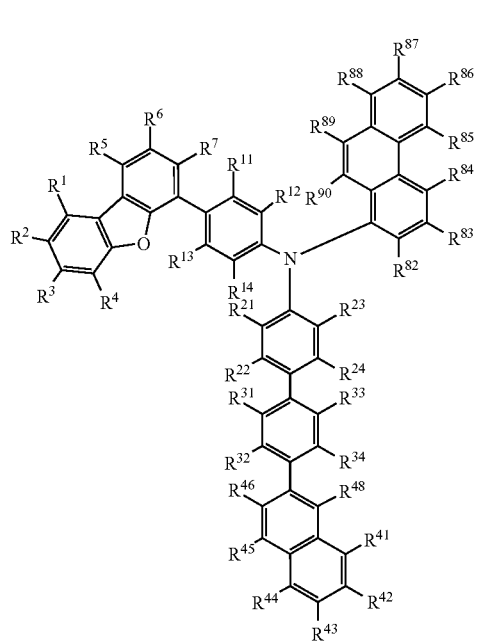
(15c)
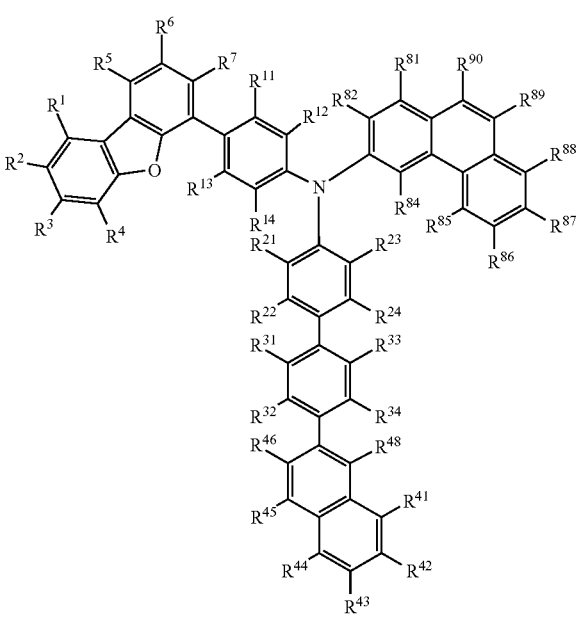

-continued

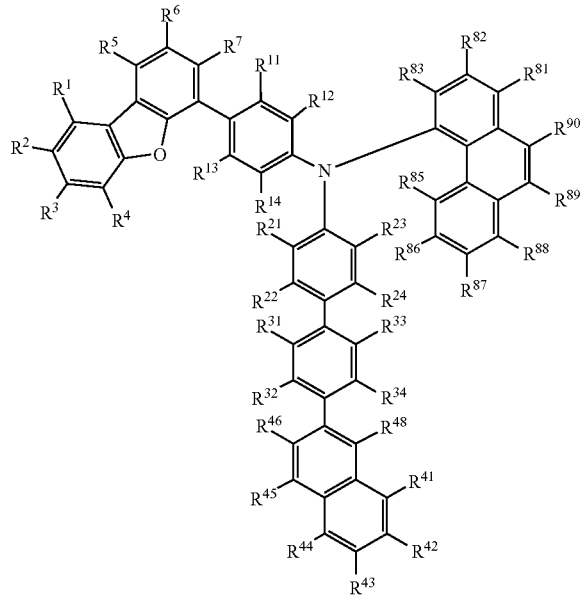

(15d)

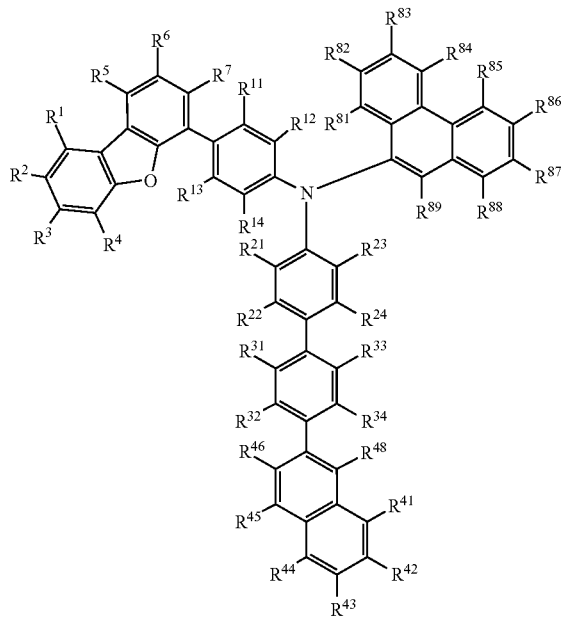

(15e)

The symbols in the formulae above will be explained below. Unless otherwise noted, the same symbols have the same meaning.

The halogen atom, the alkyl group having 1 to 10 carbon atoms, and the cycloalkyl group having 3 to 6 ring carbon atoms are defined as follows, unless otherwise noted.

The halogen atom is preferably an iodine atom, a bromine atom, a chlorine atom, or a fluorine atom, with a chlorine atom and a fluorine atom being preferred.

The alkyl group having 1 to 10 carbon atoms is preferably an alkyl group having 1 to 6 carbon atoms, and more preferably an alkyl group having 1 to 4 carbon atoms. Examples thereof include a methyl group, an ethyl group a n-propyl group, a sec-propyl group, an isopropyl group, a n-butyl group, a sec-butyl group, an isobutyl group, and a t-butyl group, with a methyl group, an ethyl group, an isopropyl group, an isobutyl group, and a t-butyl group being preferred, a methyl group, an ethyl group, an isopropyl group, and a t-butyl group being more preferred, and a methyl group and a t-butyl group being still more preferred.

The cycloalkyl group having 3 to 6 ring carbon atoms is preferably a cycloalkyl group having 5 or 6 ring carbon atoms. Examples thereof include a cyclopropyl group, a cyclobutyl group, a cyclopentyl group, and a cyclohexyl group, with a cyclopentyl group and a cyclohexyl group being preferred.

Ar is a substituted or unsubstituted phenyl group, a substituted or unsubstituted biphenylyl group, a substituted or unsubstituted naphthyl group, or a substituted or unsubstituted phenanthryl group.

The biphenylyl group includes an o-biphenylyl group, a m-biphenylyl group, and a p-biphenylyl group; the naphthyl group includes a 1-naphthyl group and 2-naphthyl group; and the phenanthryl group includes a 1-phenanthryl group, a 2-phenanthryl group, a 3-phenanthryl group, a 4-phenanthryl group, and a 9-phenanthryl group.

The biphenylyl group is preferably an o-biphenylyl group or a p-biphenylyl group, the naphthyl group is preferably a 1-naphthyl group, and the phenanthryl group is preferably a 2-phenanthryl group or a 9-phenanthryl group.

In an embodiment of the invention, Ar is preferably an unsubstituted phenyl group, an unsubstituted biphenylyl group, an unsubstituted naphthyl group, or an unsubstituted phenanthryl group.

The optional substituent for the phenyl group, the biphenylyl group, the naphthyl group, and the phenanthryl group is independently selected from a halogen atom, an alkyl group having 1 to 10 carbon atoms, and a cycloalkyl group having 3 to 6 ring carbon atoms. The details of the halogen atom, the alkyl group having 1 to 10 carbon atoms, and the cycloalkyl group having 3 to 6 ring carbon atoms are as described above.

If the phenyl group, the biphenylyl group, the naphthyl group, or the phenanthryl group has adjacent two optional substituent, the adjacent two optional substituents are not bonded to each other thereby failing to form a ring structure.

$R^1$ to $R^7$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In an embodiment of the invention, $R^1$ to $R^7$ are preferably all hydrogen atoms.

$R^{11}$ to $R^{14}$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In an embodiment of the invention, $R^{11}$ to $R^{14}$ are preferably all hydrogen atoms.

$R^{21}$ to $R^{24}$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In an embodiment of the invention, $R^{21}$ to $R^{24}$ are preferably all hydrogen atoms.

$R^{31}$ to $R^{34}$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In an embodiment of the invention, $R^{31}$ to $R^{34}$ are preferably all hydrogen atoms.

$R^{41}$ to $R^{48}$ are each independently a hydrogen atom, a halogen atom, an alkyl group having 1 to 10 carbon atoms, or a cycloalkyl group having 3 to 6 ring carbon atoms, provided that one of $R^{47}$ and $R^{48}$ is a single bond bonded to *1. The details of the halogen atom, the alkyl group having 1 to 10 carbon atoms, and the cycloalkyl group having 3 to 6 ring carbon atoms are as described above.

In an embodiment of the invention, $R^{41}$ to $R^{48}$ not the single bond bonded to *1 are preferably all hydrogen atoms.

In formula (A), adjacent two selected from $R^1$ to $R^7$, $R^{11}$ to $R^{14}$, $R^{21}$ to $R^{24}$, $R^{31}$ to $R^{34}$, and $R^{41}$ to $R^{48}$ not the single bond bonded to *1 are not bonded to each other thereby failing to form a ring structure.

In formulae (2) and (12), $R^{51}$ to $R^{55}$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In formulae (2) and (12), $R^1$ to $R^7$, $R^{11}$ to $R^{14}$, $R^{21}$ to $R^{24}$, $R^{31}$ to $R^{34}$, and $R^{41}$ to $R^{48}$ are as defined in formula (A), and adjacent two selected from $R^{51}$ to $R^{55}$ are not bonded to each other thereby failing to form a ring structure.

In an embodiment of the invention, $R^{51}$ to $R^{55}$ are preferably all hydrogen atoms.

In formulae (3) and (13), one selected from $R^{61}$ to $R^{65}$ is a single bond bonded to *a.

$R^{61}$ to $R^{65}$ not the single bond bonded to *a and $R^{66}$ to $R^{70}$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In formulae (3) and (13), $R^1$ to $R^7$, $R^{11}$ to $R^{14}$, $R^{21}$ to $R^{24}$, $R^{31}$ to $R^{34}$, and $R^{41}$ to $R^{48}$ are as defined in formula (A), and adjacent two selected from $R^{61}$ to $R^{65}$ not the single bond bonded to *a and $R^{66}$ to $R^{70}$ are not bonded to each other thereby failing to form a ring structure.

In an embodiment of the invention, $R^{61}$ to $R^{65}$ not the single bond bonded to *a and $R^{66}$ to $R^{70}$ are preferably all hydrogen atoms.

In formulae (4) and (14), one selected from $R^{71}$ and $R^{72}$ is a single bond bonded to *b.

$R^{71}$ or $R^{72}$ not the single bond bonded to *b and $R^{73}$ to $R^{78}$ are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In formulae (4) and (14), $R^1$ to $R^7$, $R^{11}$ to $R^{14}$, $R^{21}$ to $R^{24}$, $R^{31}$ to $R^{34}$, and $R^{41}$ to $R^{48}$ are as defined in formula (A), and adjacent two selected from $R^{71}$ or $R^{72}$ not the single bond bonded to *b and $R^{73}$ to $R^{78}$ are not bonded to each other thereby failing to form a ring structure.

In an embodiment of the invention, $R^{71}$ or $R^{72}$ not the single bond bonded to *b and $R^{73}$ to $R^{78}$ are preferably all hydrogen atoms.

In formulae (5) and (15), one selected from $R^{81}$ to $R^{90}$ is a single bond bonded to *c.

$R^{81}$ to $R^{90}$ not the single bond bonded to *c are each independently a hydrogen atom, a halogen atom, an alkyl group having 1 to 10 carbon atoms, or a cycloalkyl group having 3 to 6 ring carbon atoms. The details of the halogen atom, the alkyl group having 1 to 10 carbon atoms, and the cycloalkyl group having 3 to 6 ring carbon atoms are as described above.

In formulae (5) and (15), $R^1$ to $R^7$, $R^{11}$ to $R^{14}$, $R^{21}$ to $R^{24}$, $R^{31}$ to $R^{34}$, and $R^{41}$ to $R^{48}$ are as defined in formula (A), and adjacent two selected from $R^{81}$ to $R^{90}$ not the single bond bonded to *c are not bonded to each other thereby failing to form a ring structure.

In an embodiment of the invention, $R^{81}$ to $R^{90}$ not the single bond bonded to *c are preferably all hydrogen atoms.

In an embodiment of the invention, the inventive compound is preferably represented by any of the following formulae:

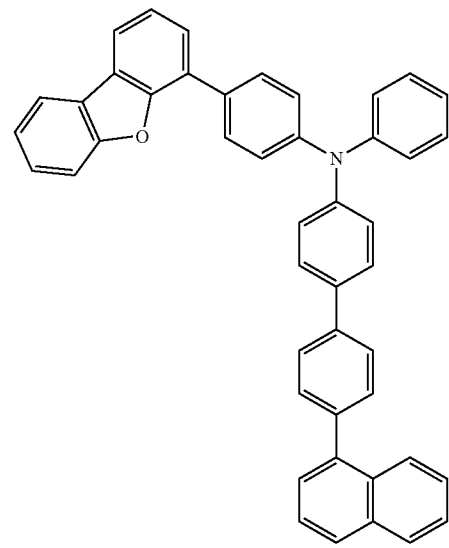

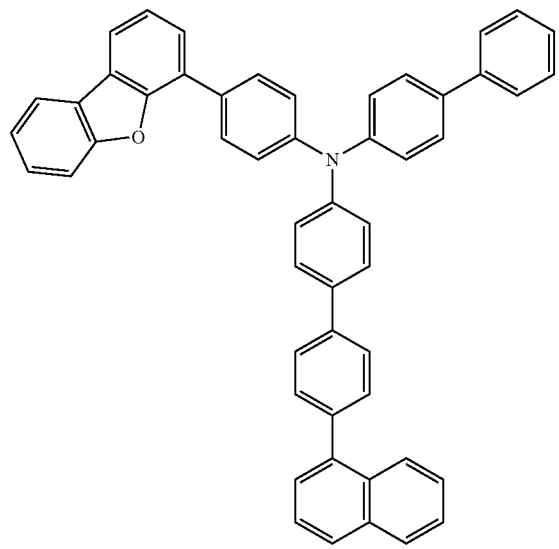

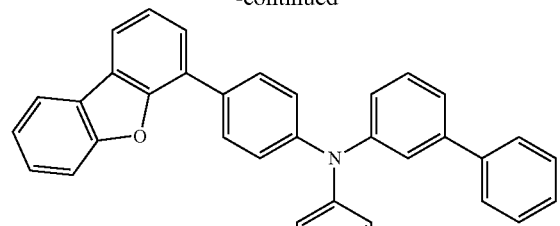
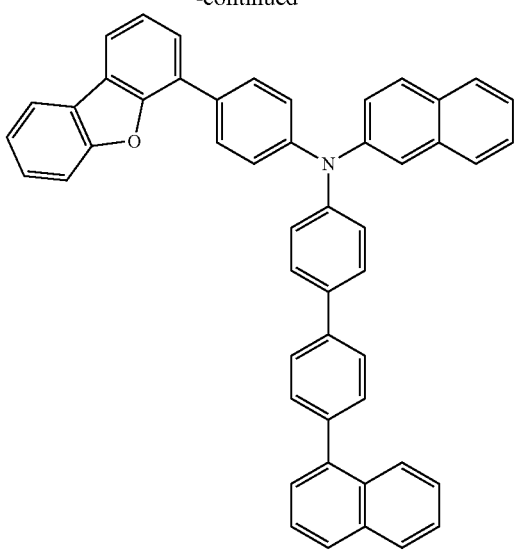
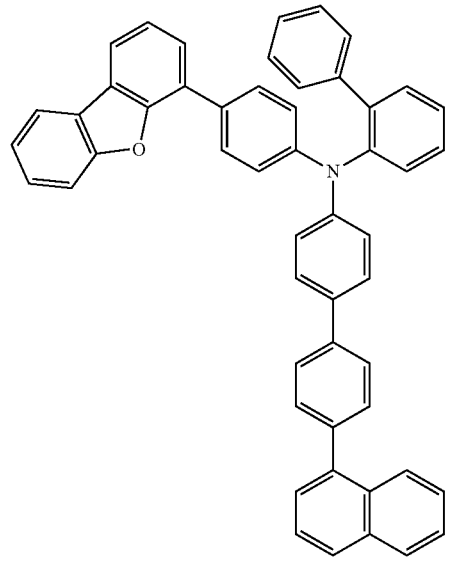
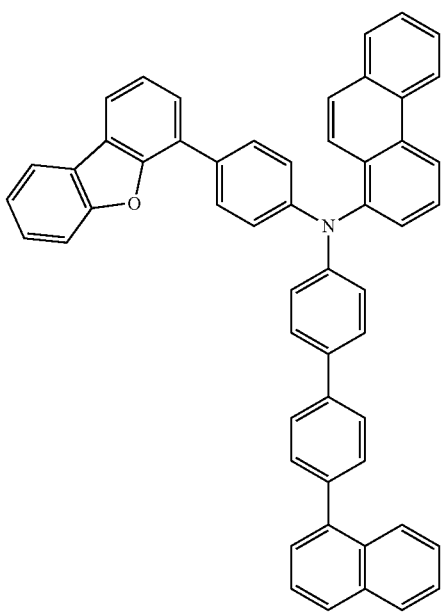
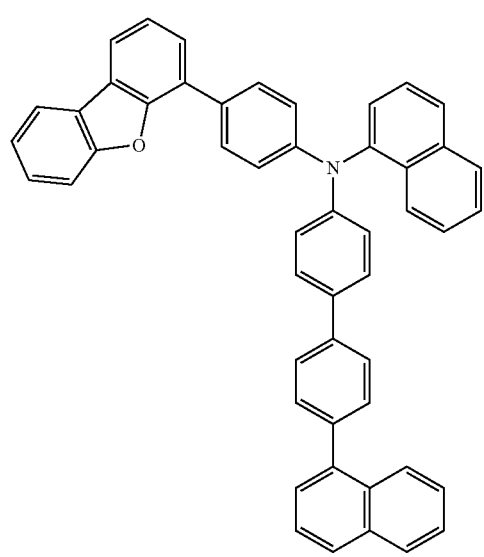
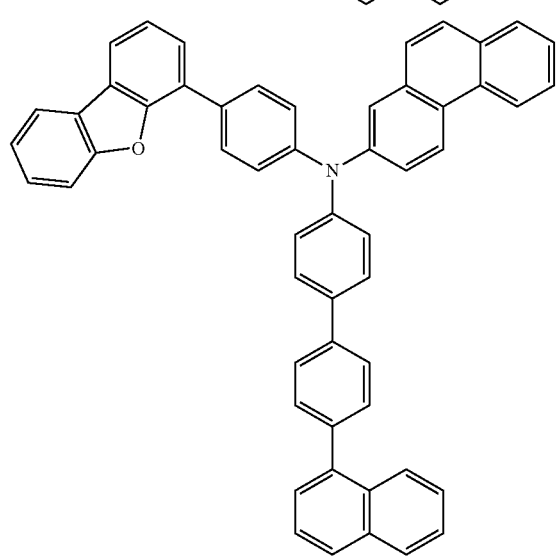

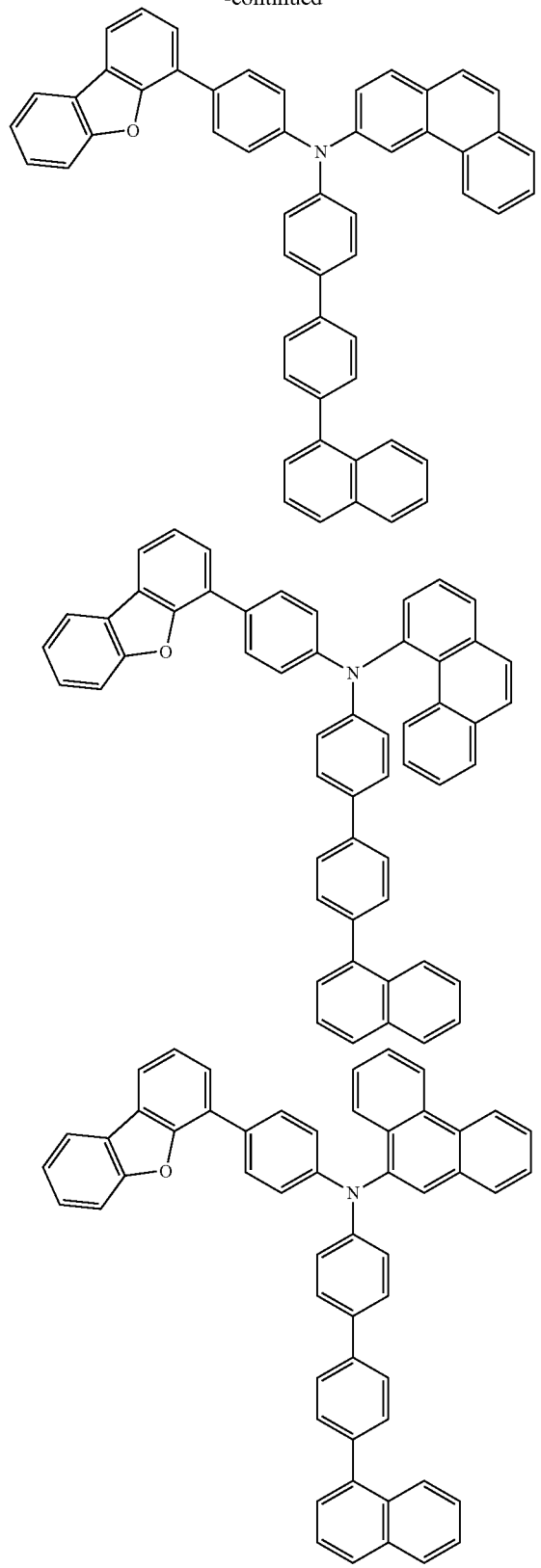
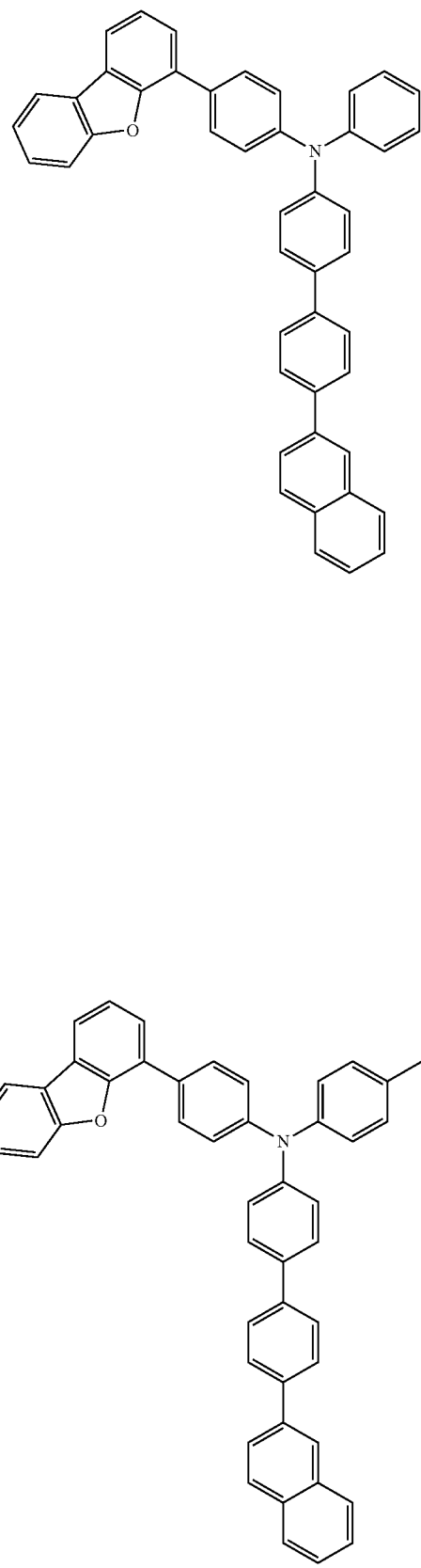
In an embodiment of the invention, the inventive compound is preferably represented by any of the following formulae:

31
-continued
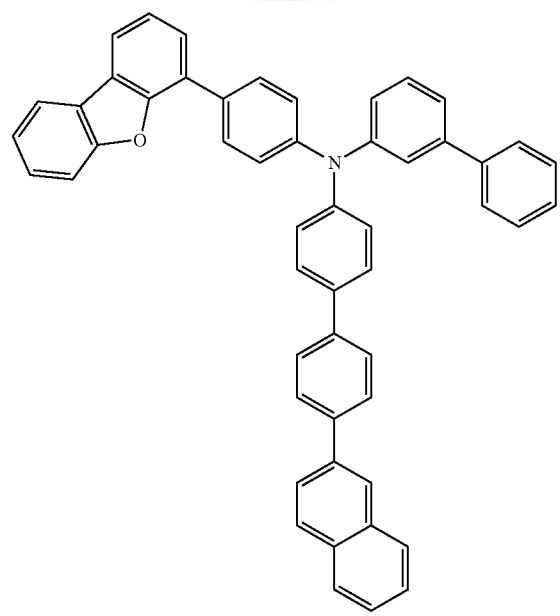
32
-continued
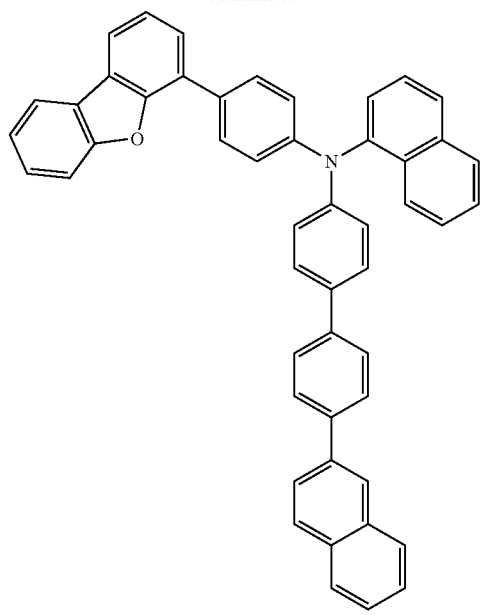
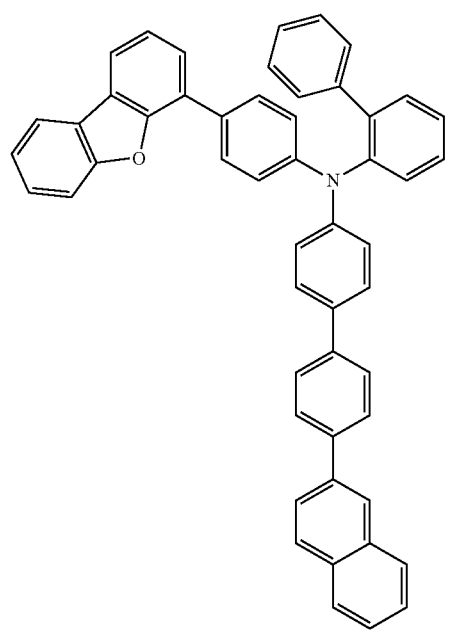
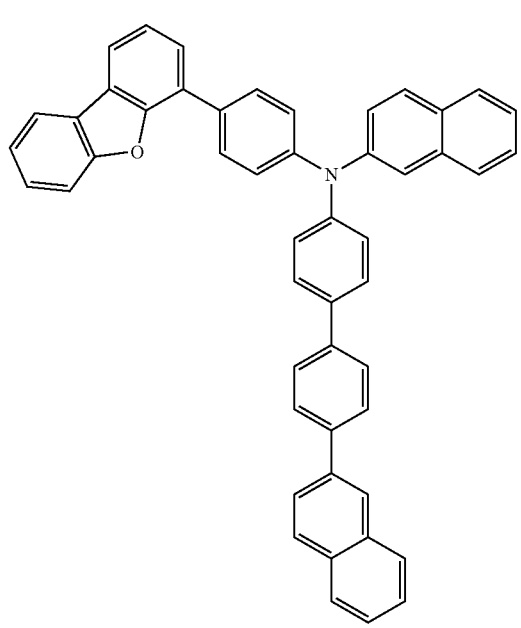 [SMILES: c1ccc2cc(-c3ccc(-c4ccc(N(c5ccc(-c6cccc7c6oc6ccccc67)cc5)c5cc6ccccc6c6ccccc56)cc4)cc3)ccc2c1]

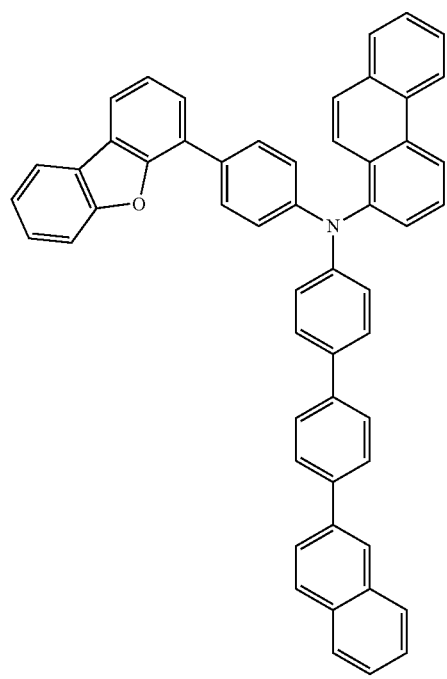
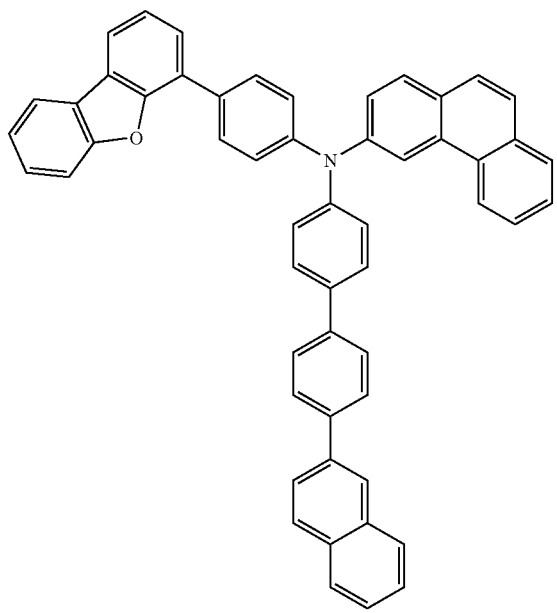
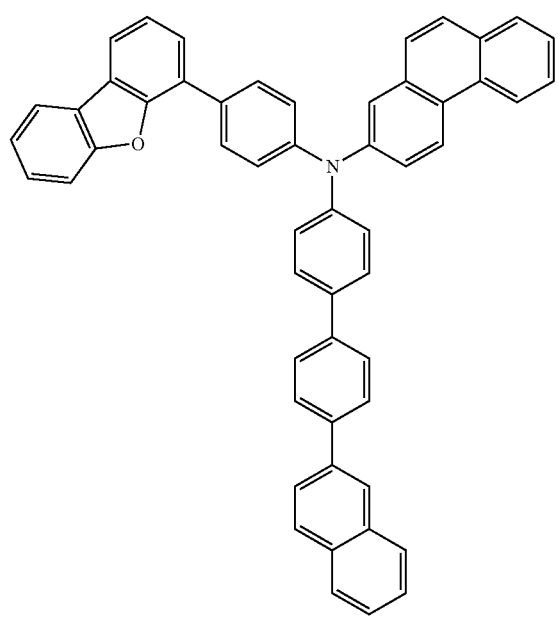
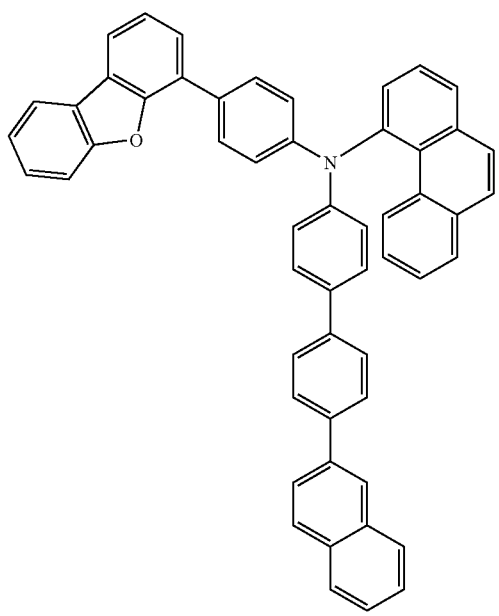

-continued

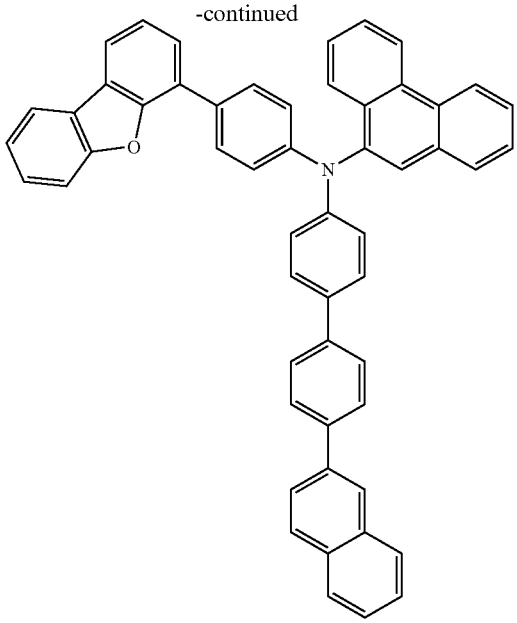

As noted above, the "hydrogen atom" referred herein includes a light hydrogen (protium), a heavy hydrogen (deuterium), and tritium. Therefore, the inventive compound may include a naturally occurring heavy hydrogen atom.

In addition, a heavy hydrogen atom may be intentionally introduced into the inventive compound by using a deuterated compound as a part or whole of the raw materials. Thus, in an embodiment of the invention, the inventive compound comprises at least one heavy hydrogen atom. Therefore, the inventive compound may be a compound that is represented by any of formula (A) and preferred formulae thereof, wherein at one of the hydrogen atoms included in the compound is a heavy hydrogen atom.

Namely, in formula (A), at least one hydrogen atom selected from the hydrogen atoms in the phenyl group, the biphenylyl group, the naphthyl group, or the phenanthryl group for Ar; the hydrogen atom(s) represented by any of $R^1$ to $R^7$; the hydrogen atom(s) represented by any of $R^{11}$ to $R^{14}$; the hydrogen atom(s) represented by any of $R^{21}$ to $R^{24}$; the hydrogen atom(s) represented by any of $R^{31}$ to $R^{34}$; and the hydrogen atom(s) represented by any of $R^{41}$ to $R^{48}$ not the single bond bonded to *1 may be a heavy hydrogen atom.

The deuteration rate of the deuterated compound (the ratio of the number of heavy hydrogen atoms to the total number of hydrogen atoms in the inventive compound) depends on the deuteration rate of the raw material to be used. It is generally difficult to use the raw materials each having a deuteration rate of 100%. Therefore, the deuteration rate of the inventive compound is less than 100% and 1% or more, preferably 3% or more, more preferably 5% or more, and still more preferably 10% or more.

The inventive compound may be a mixture of a deuterated compound and a non-deuterated compound or a mixture of two or more compounds having different deuteration rates. The deuteration rate of such a mixture (the ratio of the number of heavy hydrogen atoms to the total number of hydrogen atoms each in the mixture) is 1% or more, preferably 3% or more, more preferably 5% or more, and still more preferably 10% or more, and less than 100%.

In the inventive compound, at least one hydrogen atom selected from the hydrogen atoms in the phenyl group, the biphenylyl group, the naphthyl group, or the phenanthryl group for Ar may be a heavy hydrogen atom. The deuteration rate (the ratio of the number of heavy hydrogen atoms to the total number of hydrogen atoms each in Ar) is 1% or more, preferably 3% or more, more preferably 5% or more, and still more preferably 10% or more, and less than 100%.

In the inventive compound, at least one hydrogen atom selected from the hydrogen atom(s) represented by any of $R^1$ to $R^7$ may be a heavy hydrogen atom. The deuteration rate (the ratio of the number of heavy hydrogen atoms to the total number of hydrogen atoms each represented by $R^1$ to $R^7$) is 1% or more, preferably 3% or more, more preferably 5% or more, and still more preferably 10% or more, and less than 100%.

In the inventive compound, at least one hydrogen atom selected from the hydrogen atom(s) represented by any of $R^{11}$ to $R^{14}$ may be a heavy hydrogen atom. The deuteration rate (the ratio of the number of heavy hydrogen atoms to the total number of hydrogen atoms each represented by $R^{11}$ to $R^{14}$) is 1% or more, preferably 3% or more, more preferably 5% or more, and still more preferably 10% or more, and less than 100%.

In the inventive compound, at least one hydrogen atom selected from the hydrogen atom(s) represented by any of $R^{21}$ to $R^{24}$ may be a heavy hydrogen atom. The deuteration rate (the ratio of the number of heavy hydrogen atoms to the total number of hydrogen atoms each represented by $R^{21}$ to $R^{24}$) is 1% or more, preferably 3% or more, more preferably 5% or more, and still more preferably 10% or more, and less than 100%.

In the inventive compound, at least one hydrogen atom selected from the hydrogen atom(s) represented by any of $R^{31}$ to $R^{34}$ may be a heavy hydrogen atom. The deuteration rate (the ratio of the number of heavy hydrogen atoms to the total number of hydrogen atoms each represented by $R^{31}$ to $R^{34}$) is 1% or more, preferably 3% or more, more preferably 5% or more, and still more preferably 10% or more, and less than 100%.

In the inventive compound, at least one hydrogen atom selected from the hydrogen atom(s) represented by any of $R^{41}$ to $R^{48}$ not the single bond bonded to *1 may be a heavy hydrogen atom. The deuteration rate (the ratio of the number of heavy hydrogen atoms to the total number of hydrogen atoms each represented by $R^{41}$ to $R^{48}$ not the single bond bonded to *1) is 1% or more, preferably 3% or more, more preferably 5% or more, and still more preferably 10% or more, and less than 100%.

One of ordinary skill in the art could easily produce the inventive compound by referring to the Synthesis Examples mentioned below and known synthesis methods.

Examples of the inventive compound are shown below, although not limited thereto. D in the following examples means a heavy hydrogen atom.

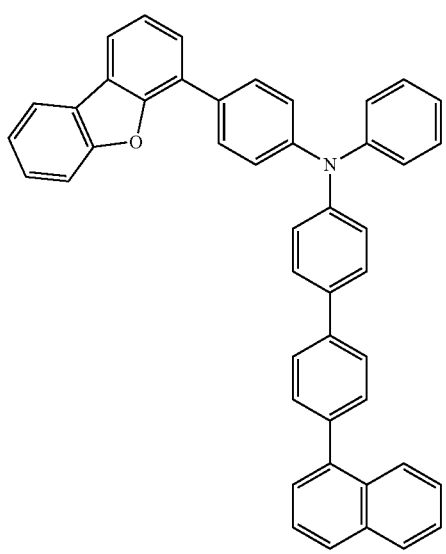
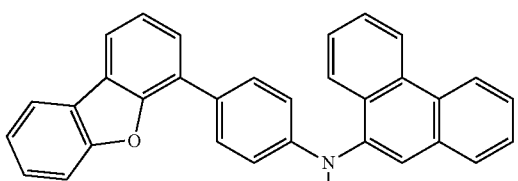
-continued
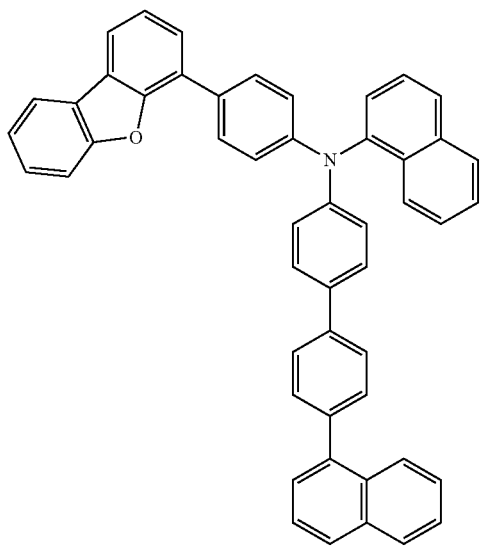
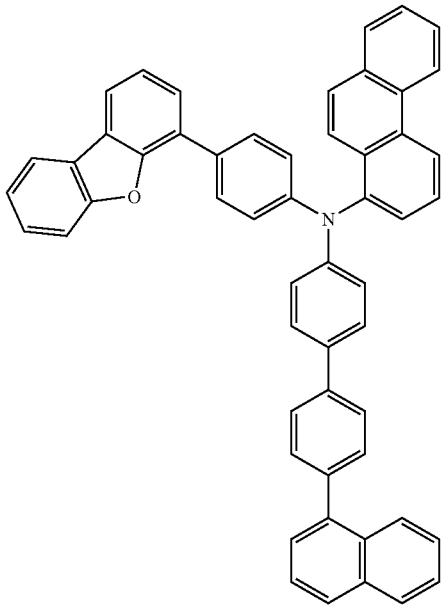
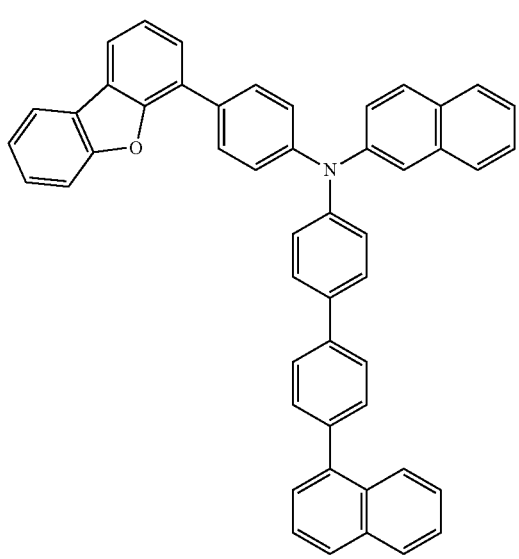
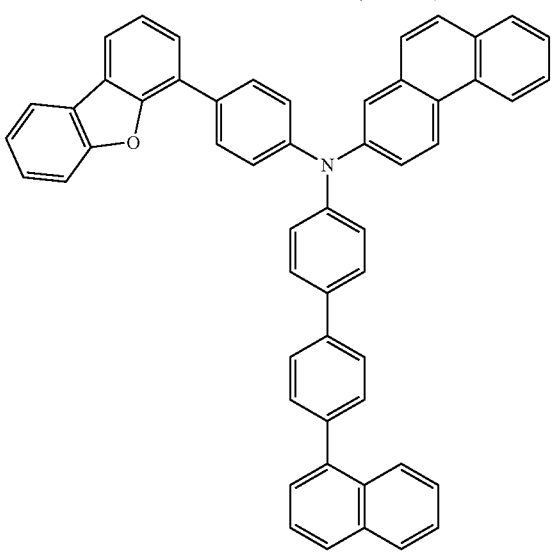

39
-continued
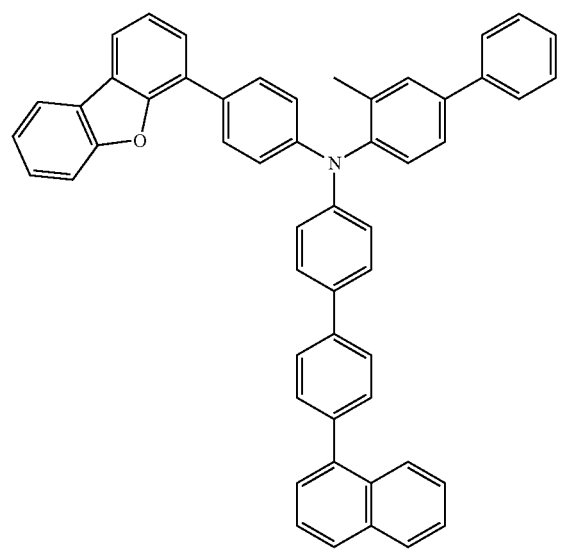
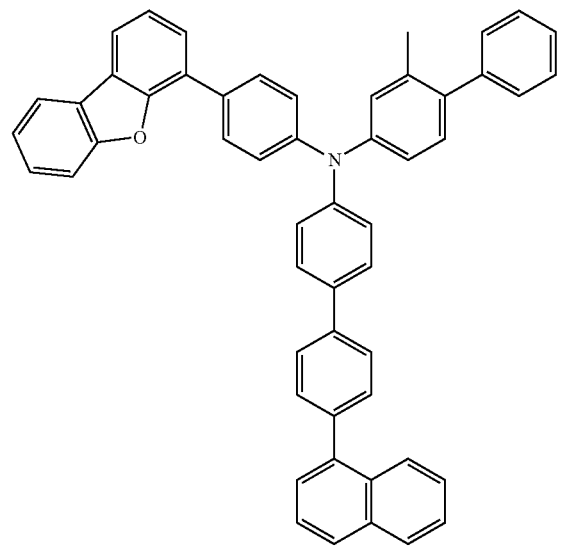
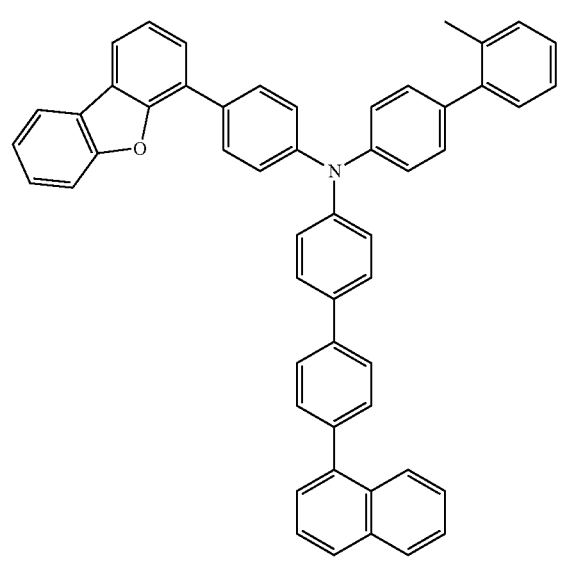
40
-continued
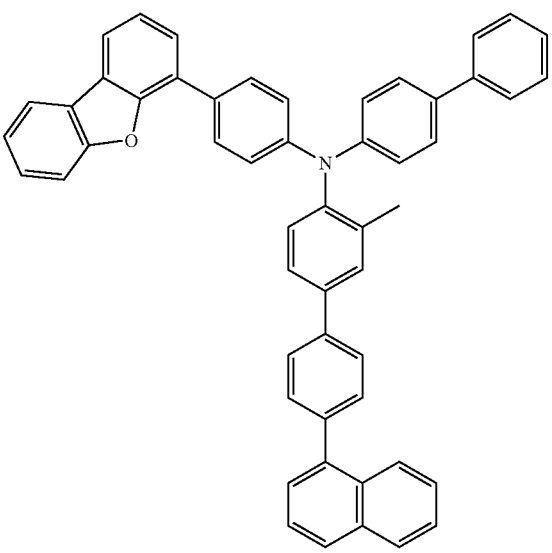
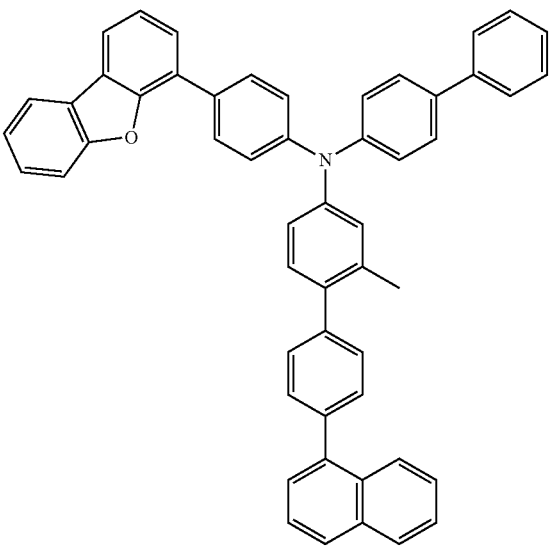

41
-continued
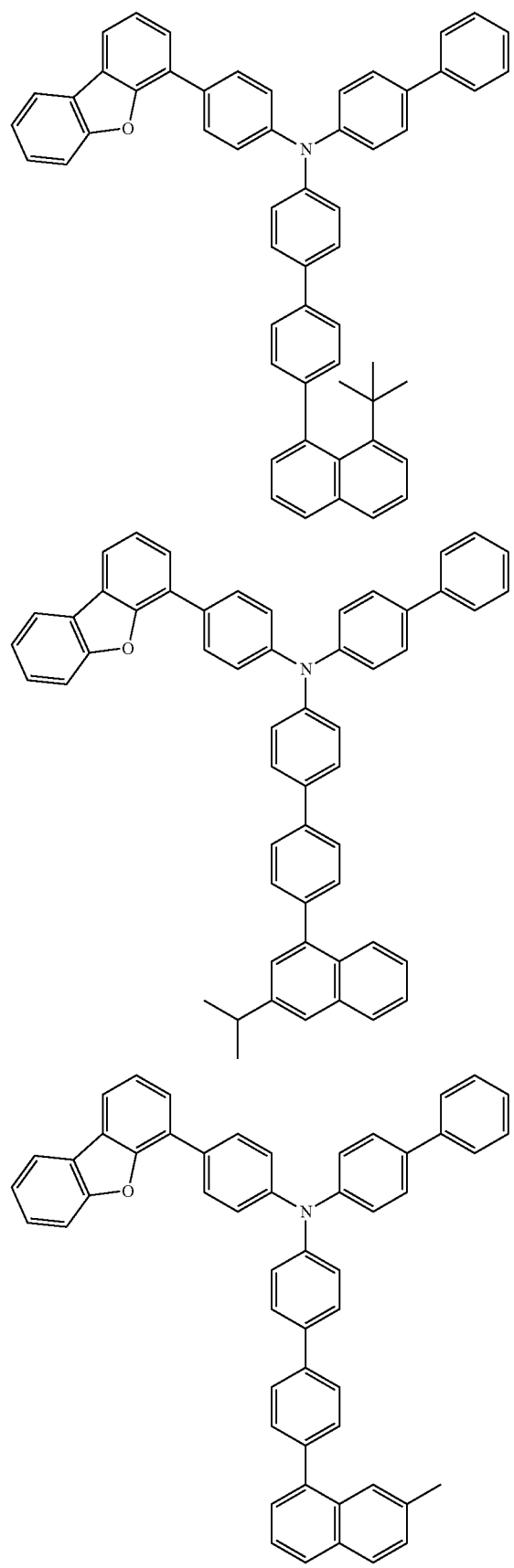
42
-continued
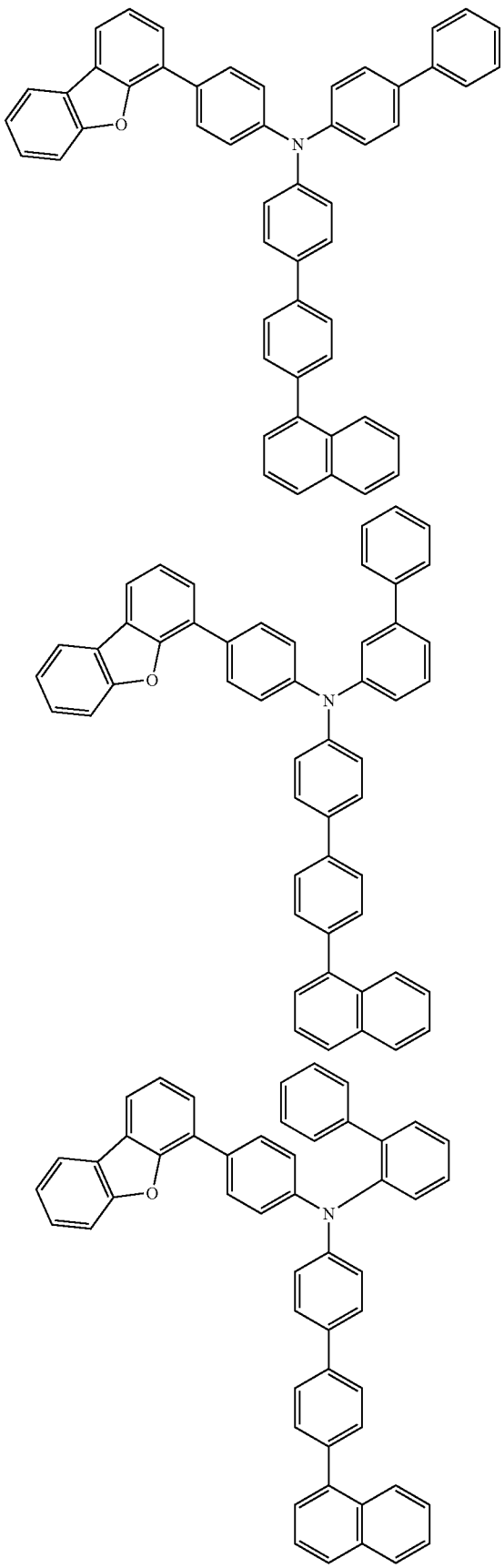

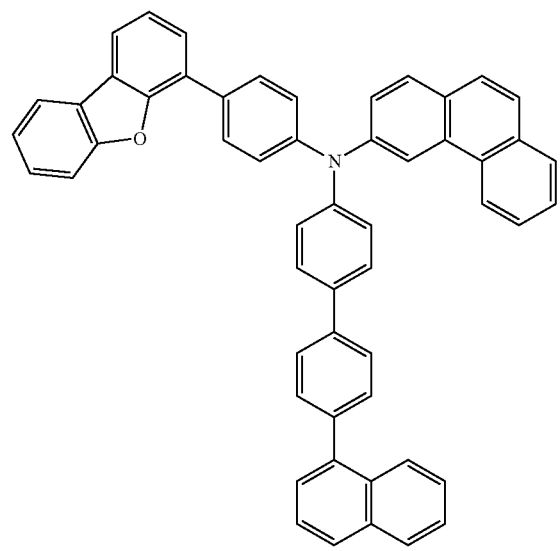
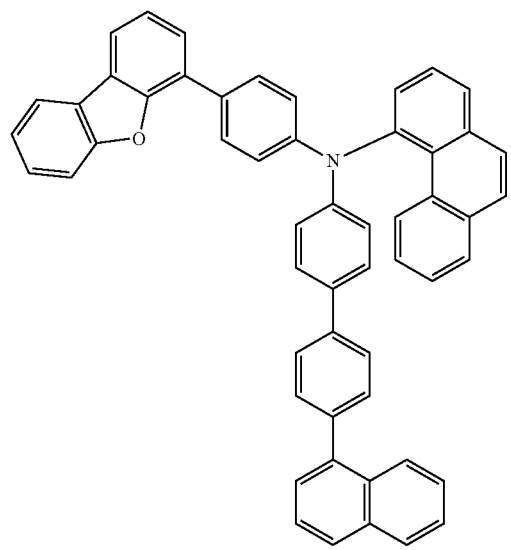
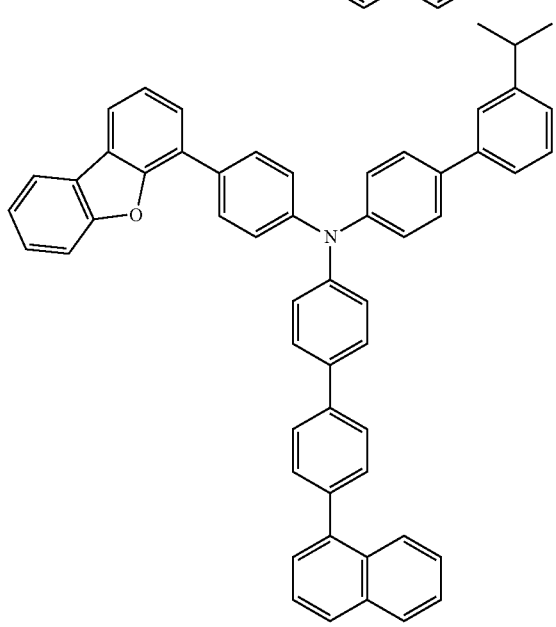
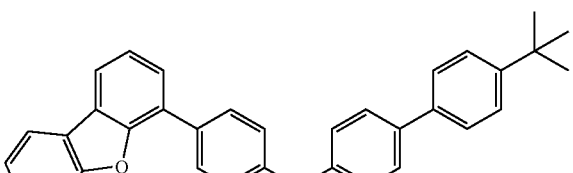
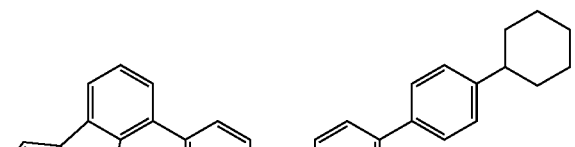
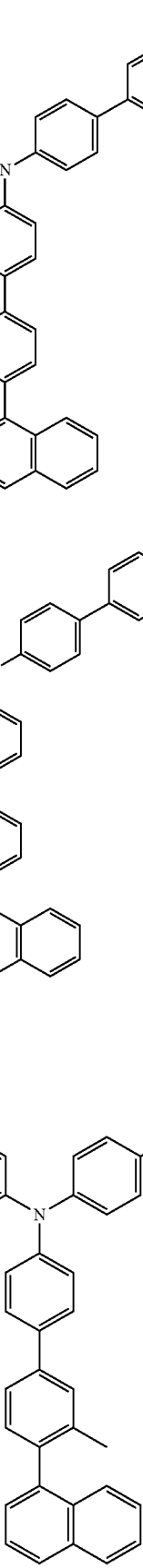

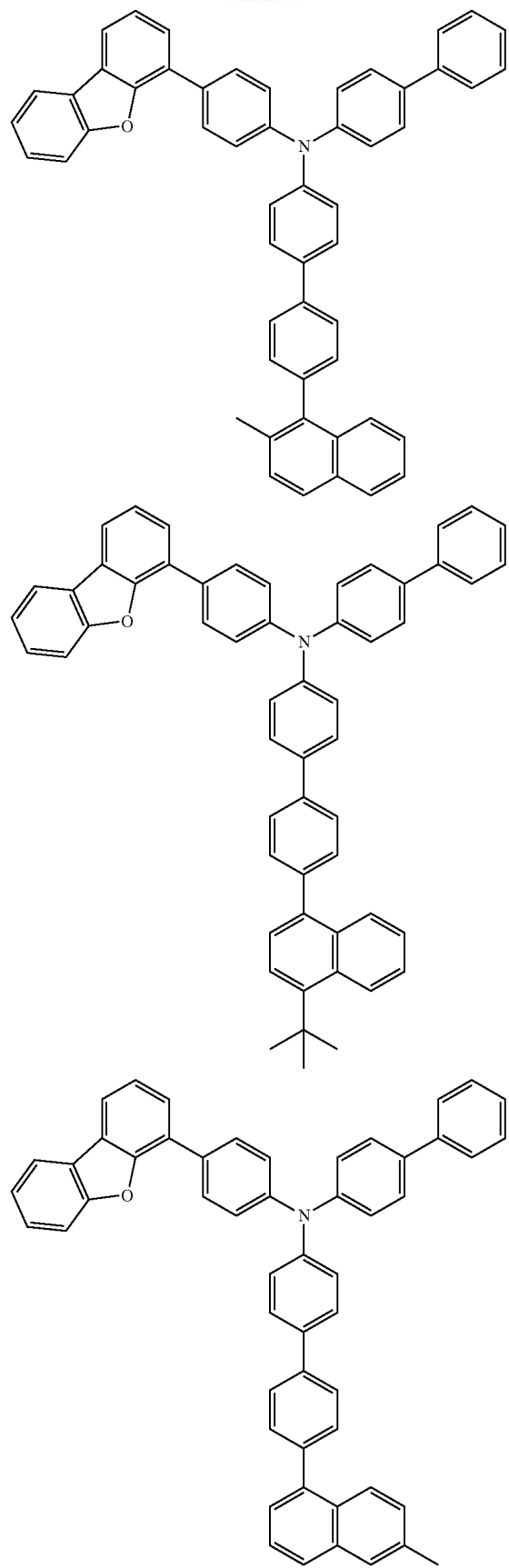
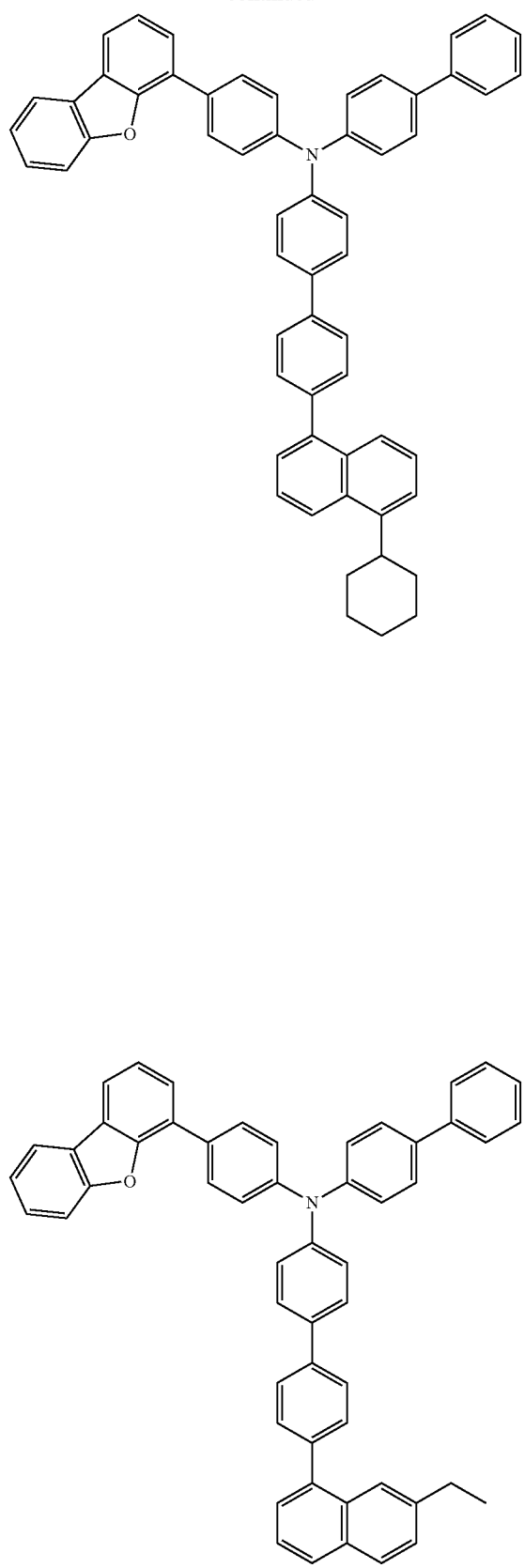

47
-continued
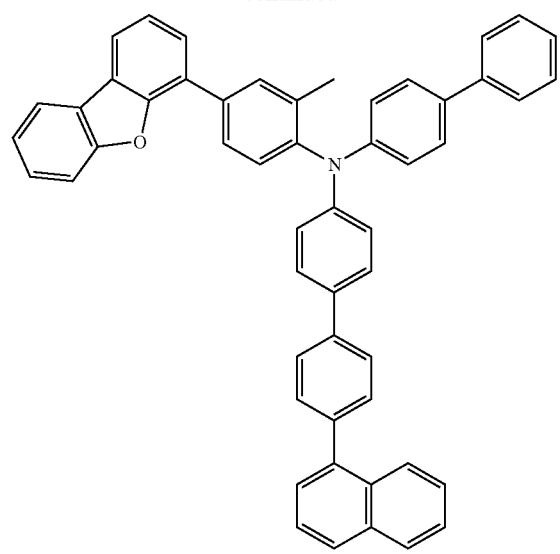
48
-continued
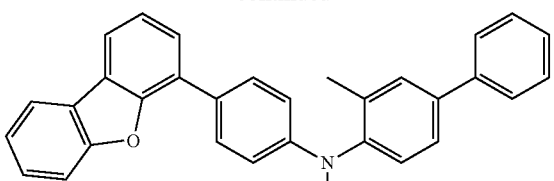
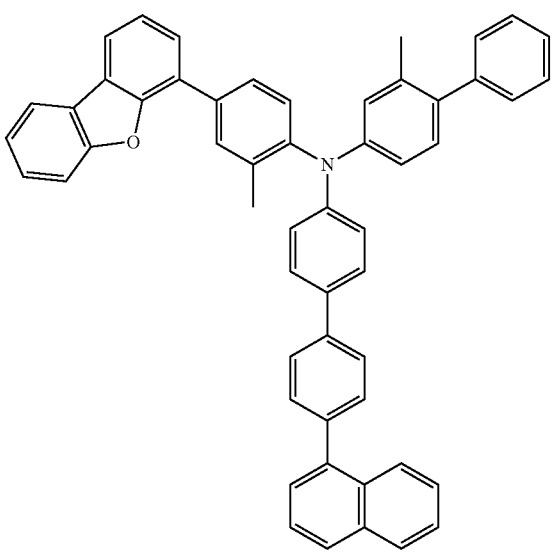
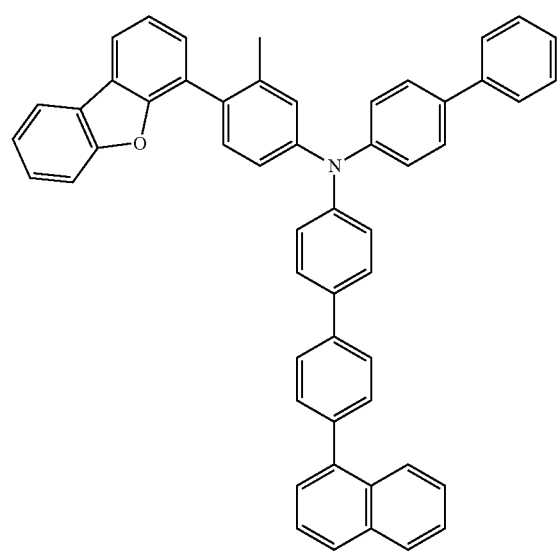
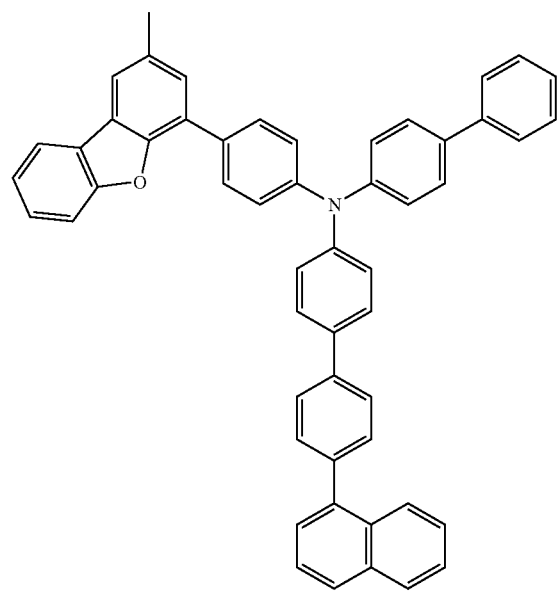
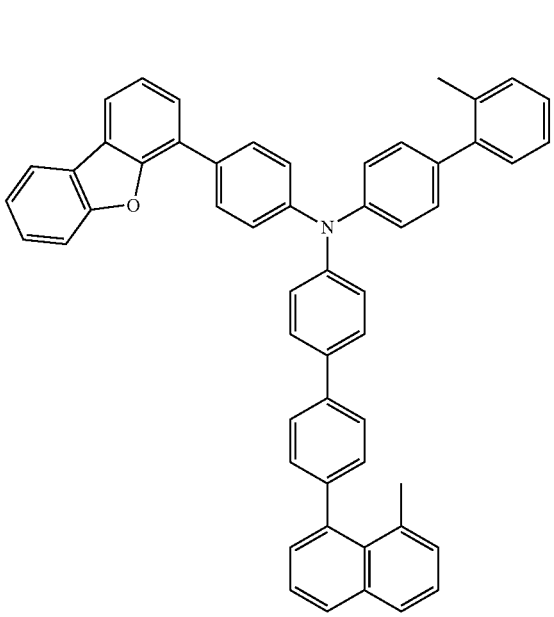

49
-continued
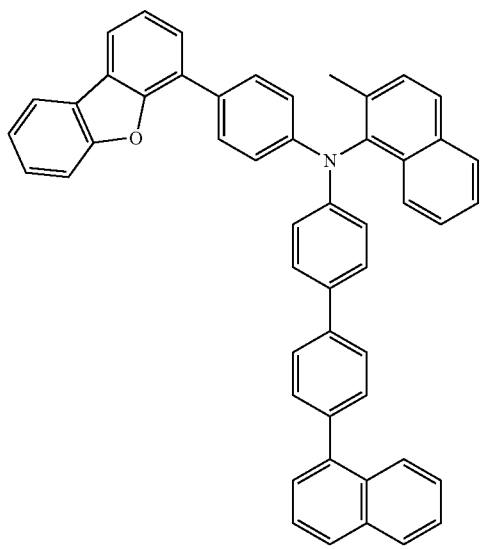
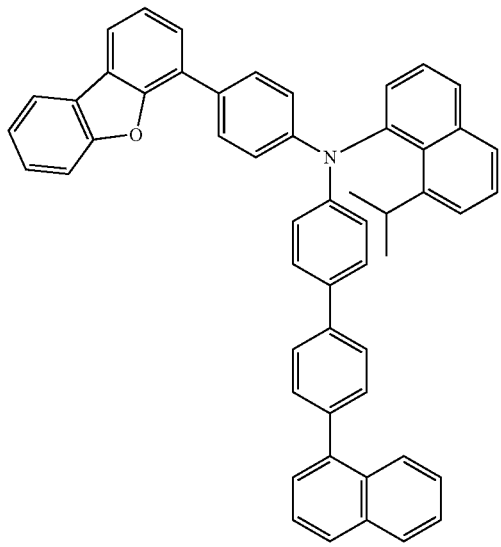
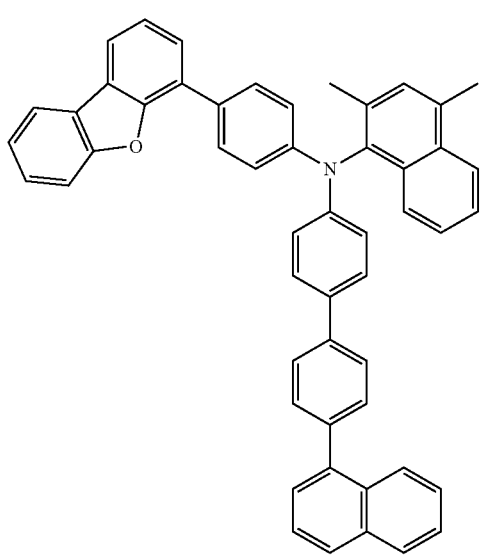
50
-continued
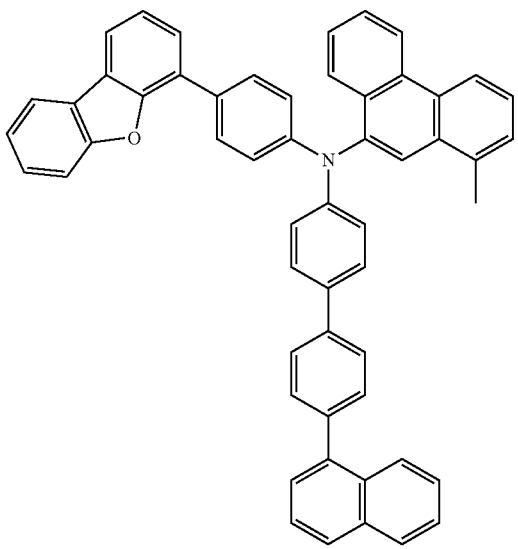
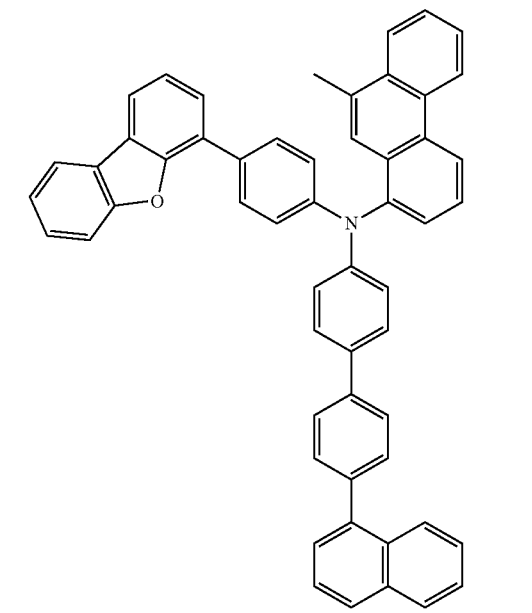
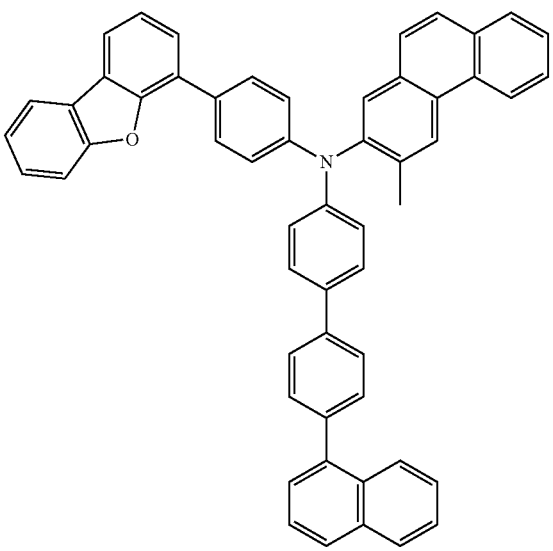

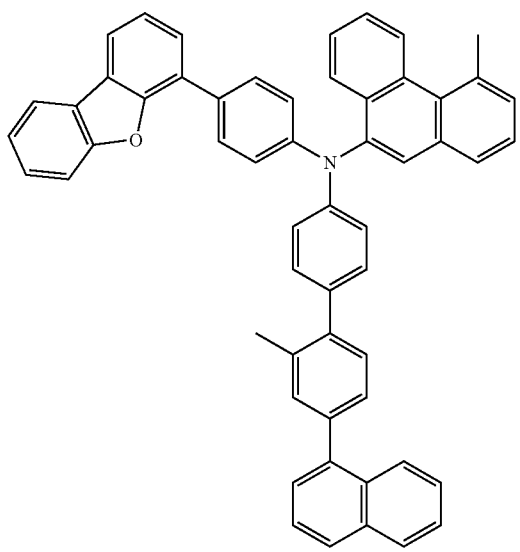
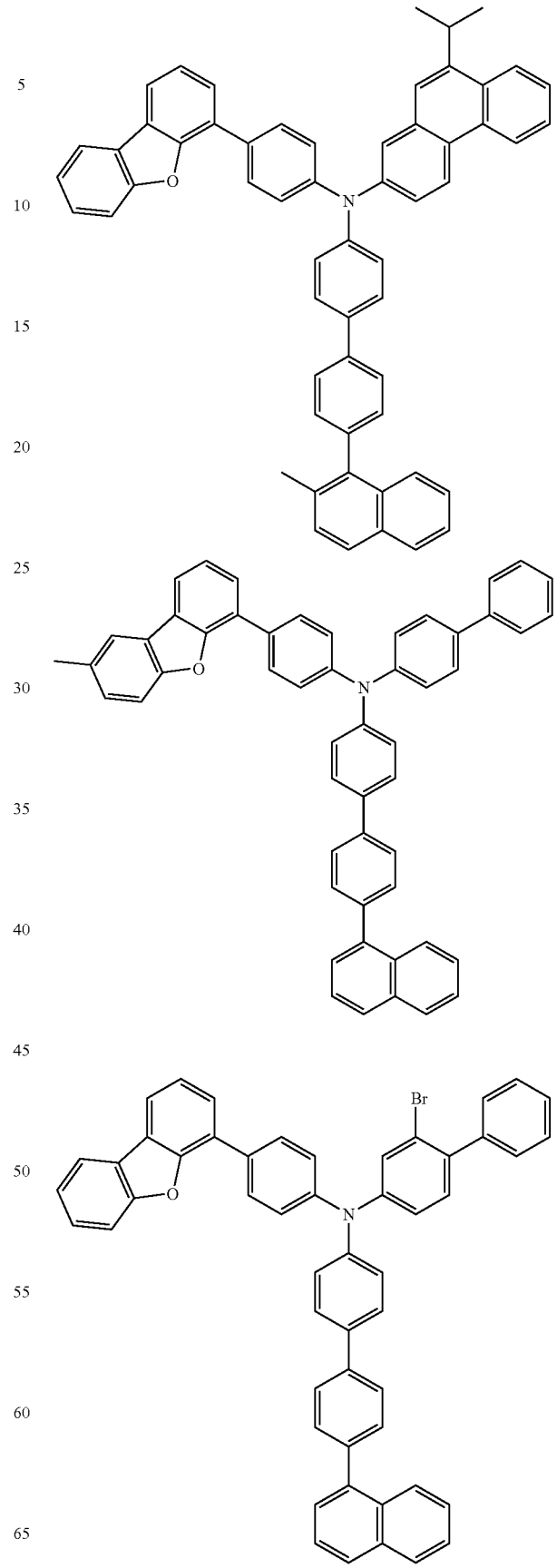

53
-continued
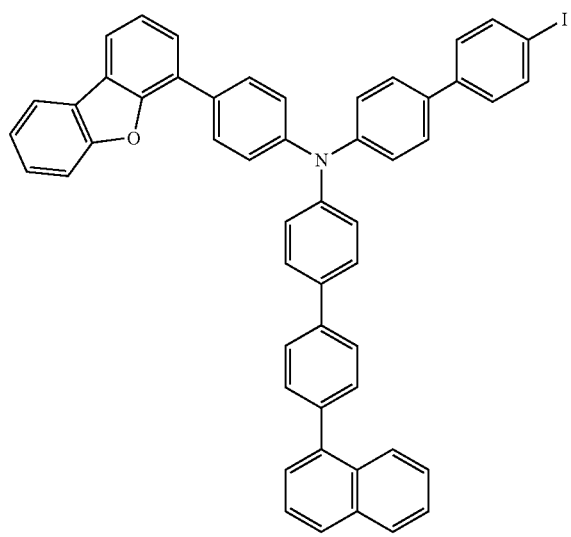
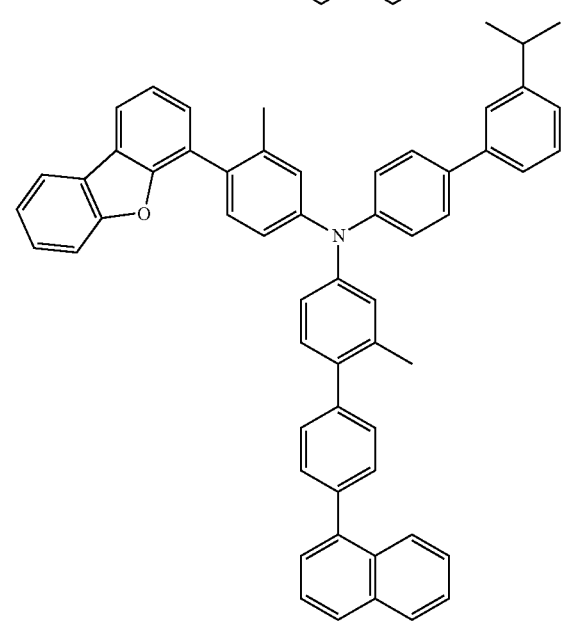
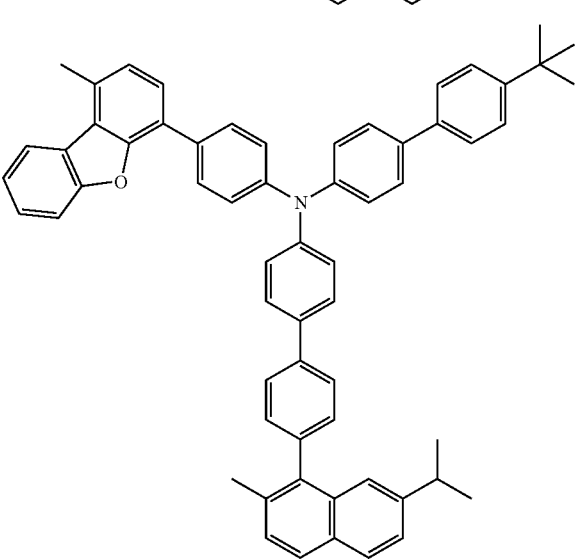
54
-continued
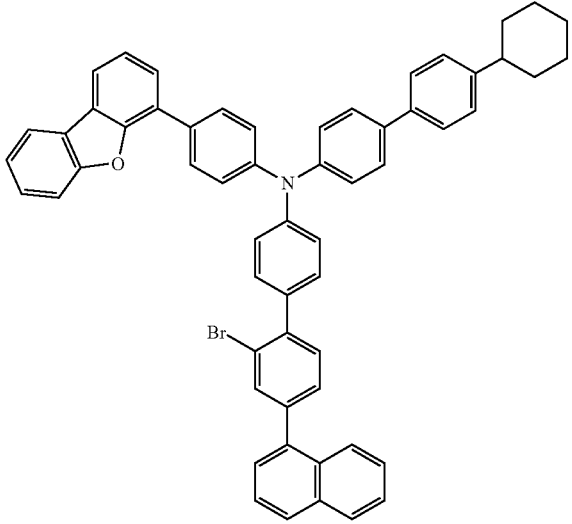
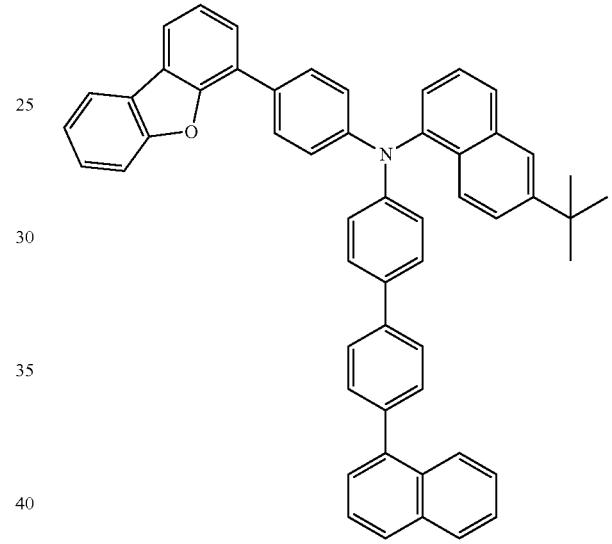
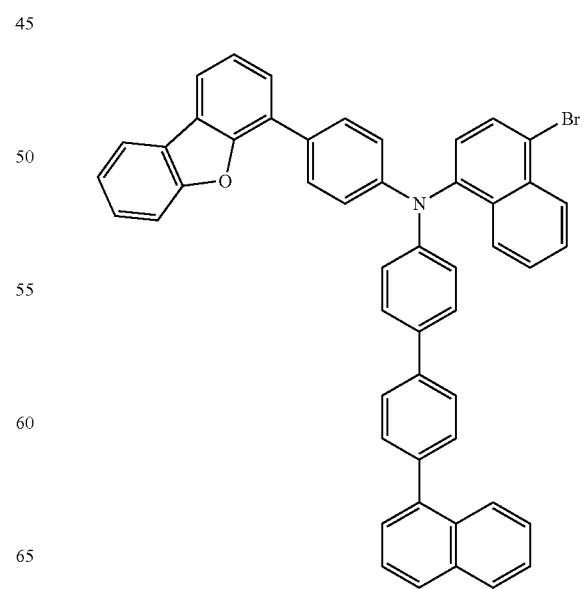

55
-continued
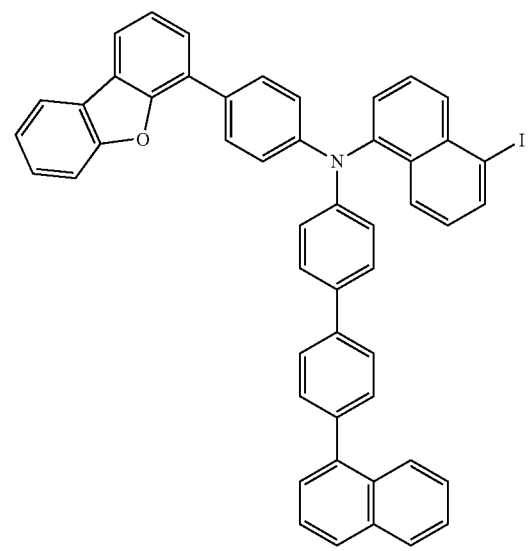
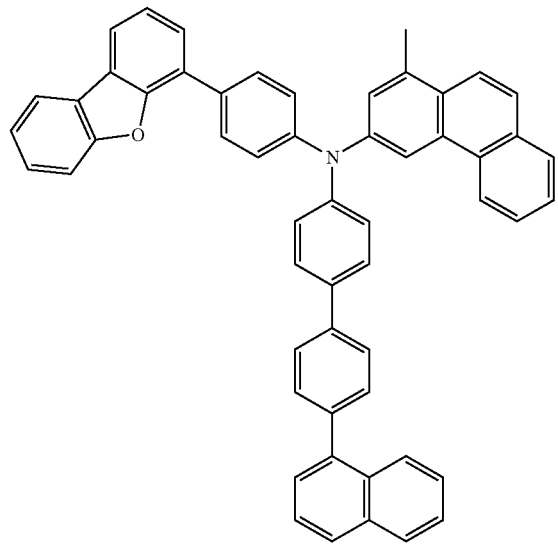
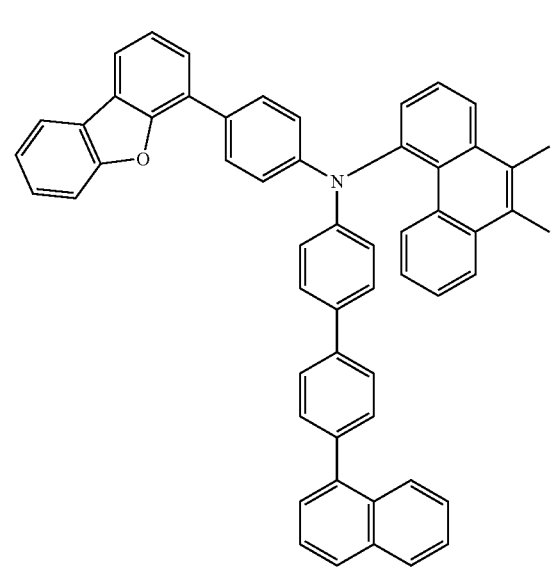
56
-continued
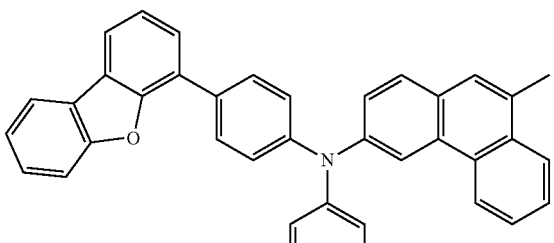
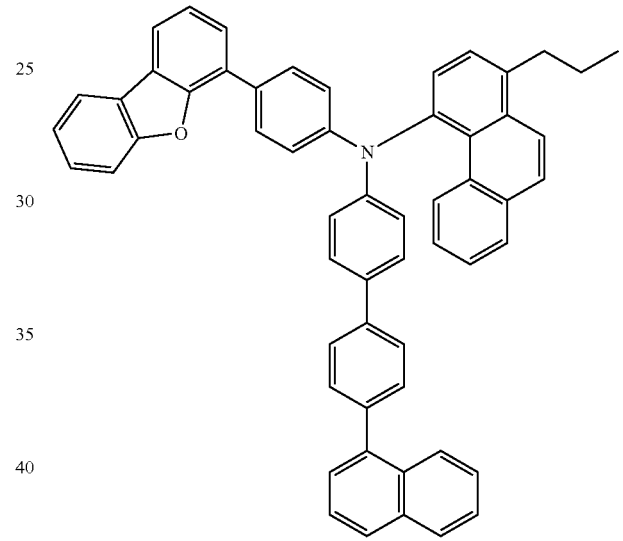
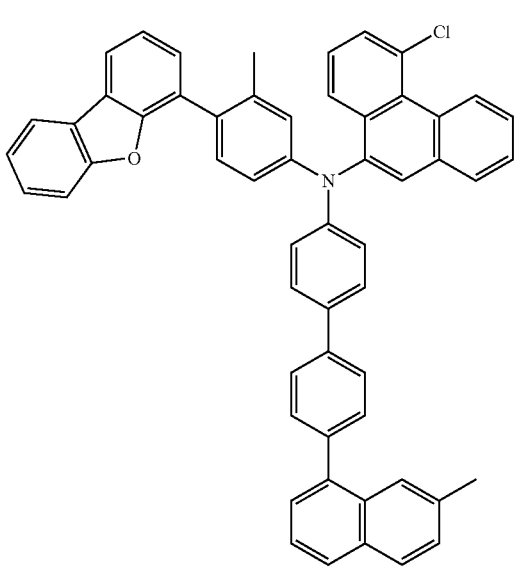

57
-continued
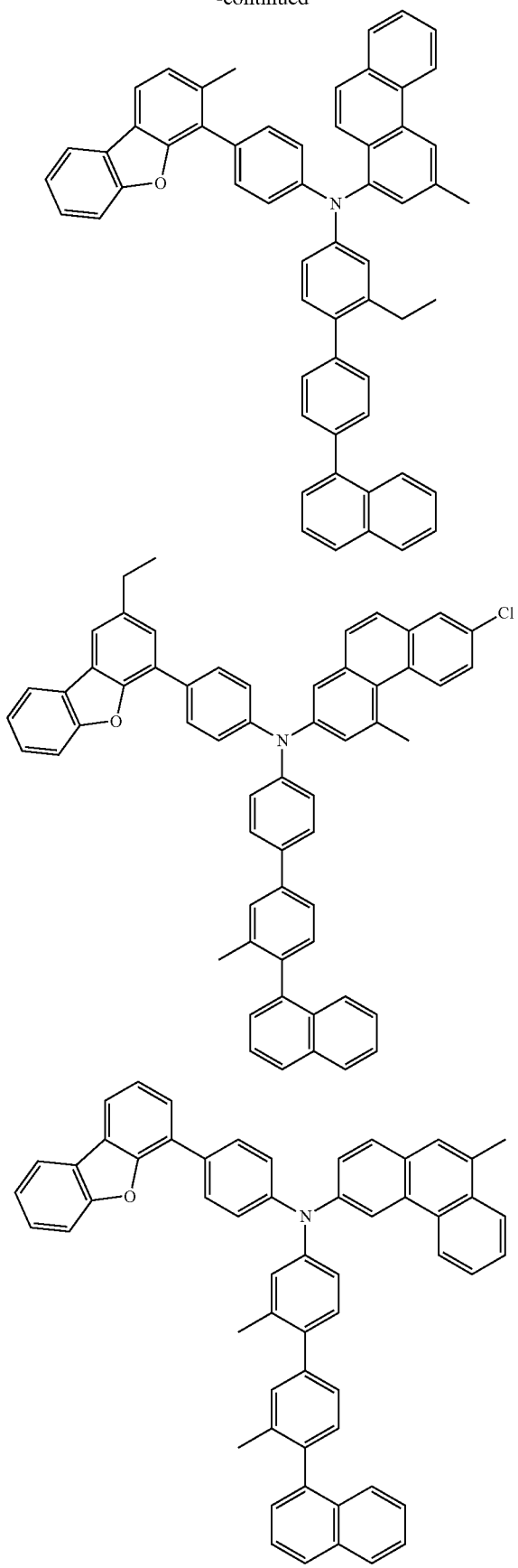
58
-continued
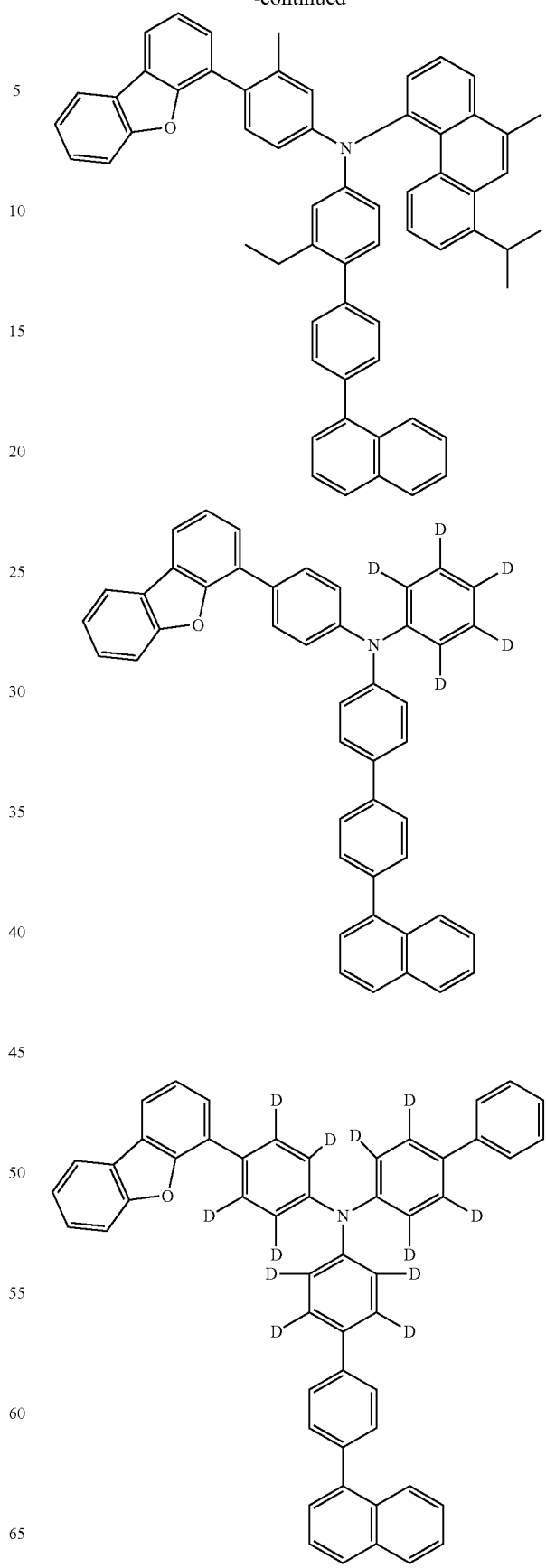

59
-continued
60
-continued
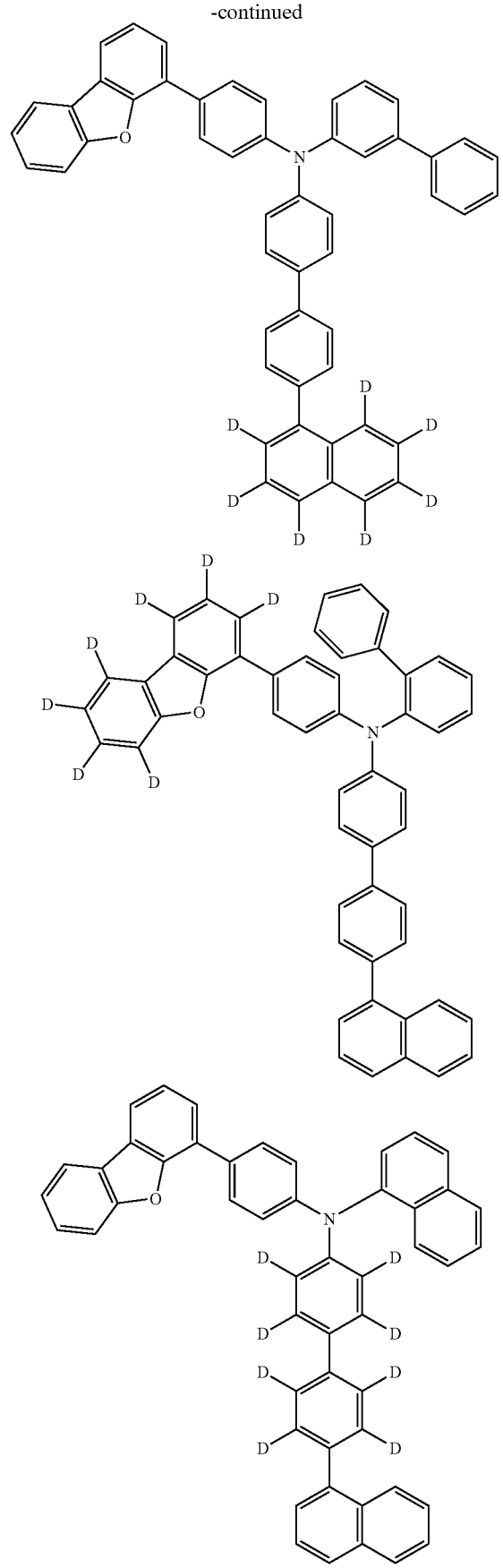
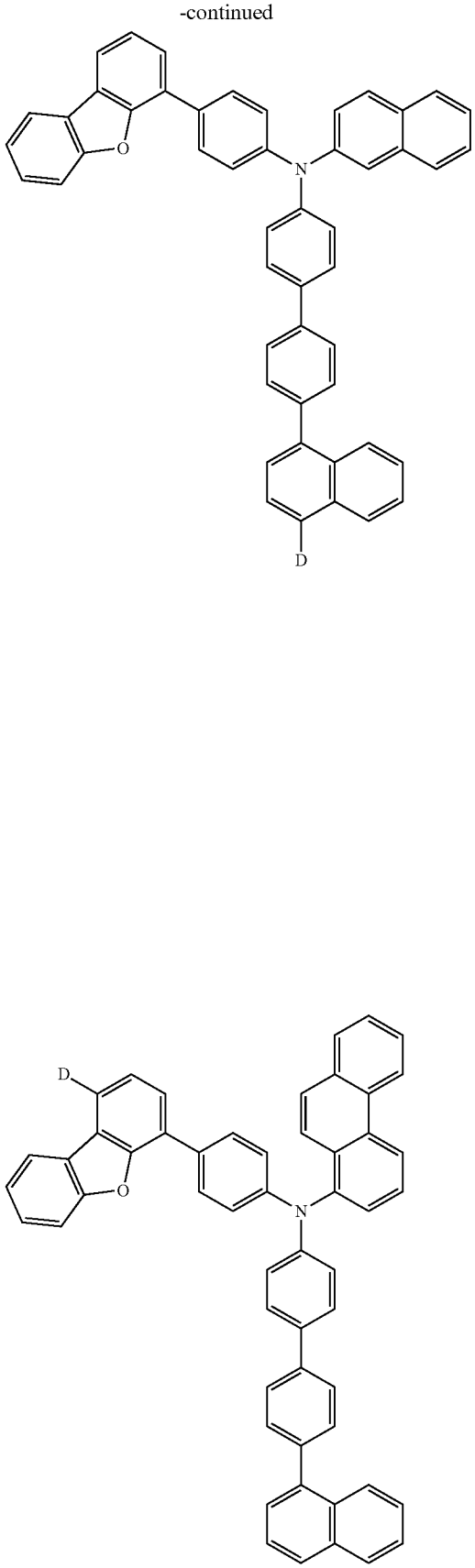

61
-continued
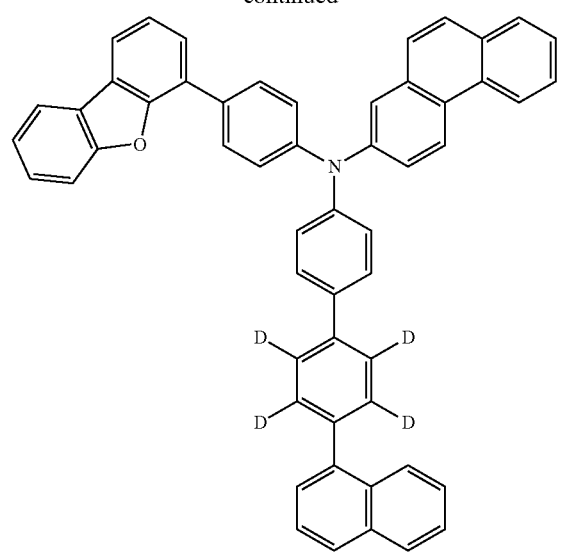
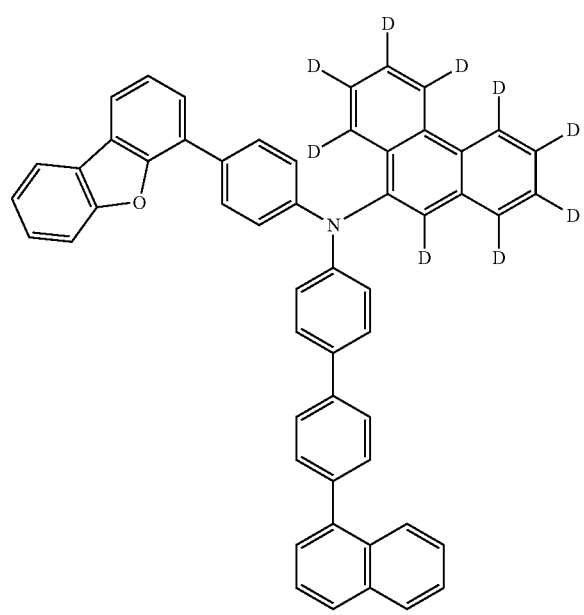
62
-continued
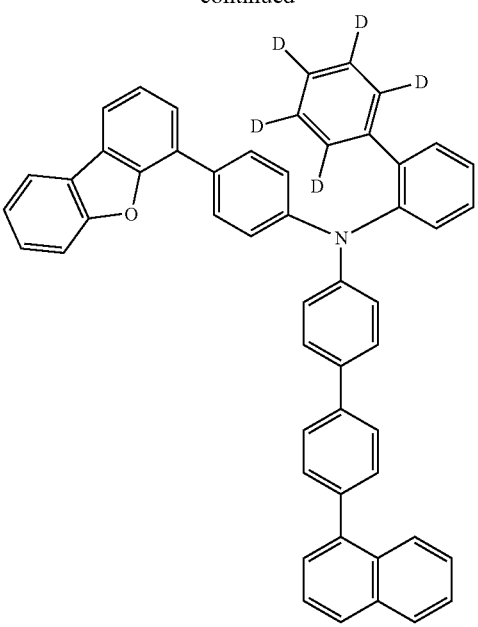
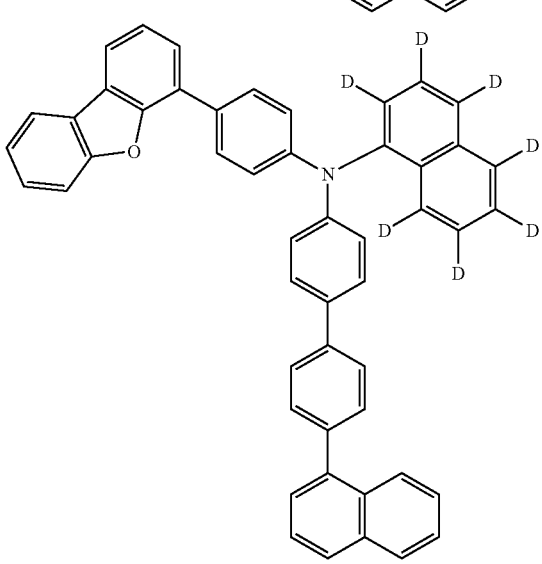

63
-continued
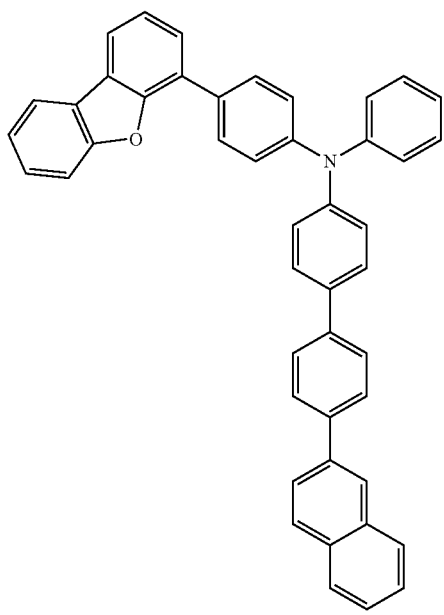
64
-continued
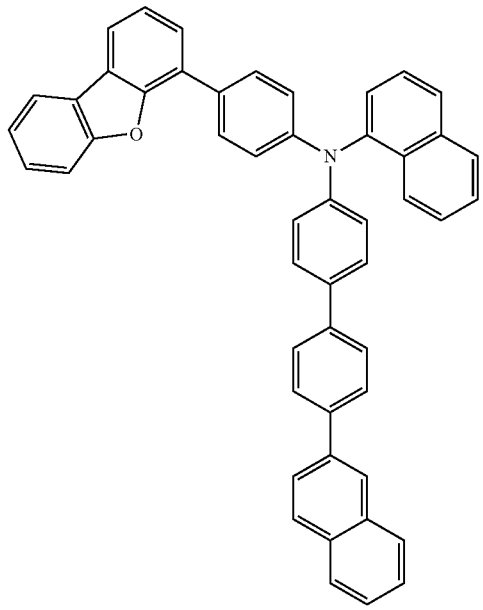
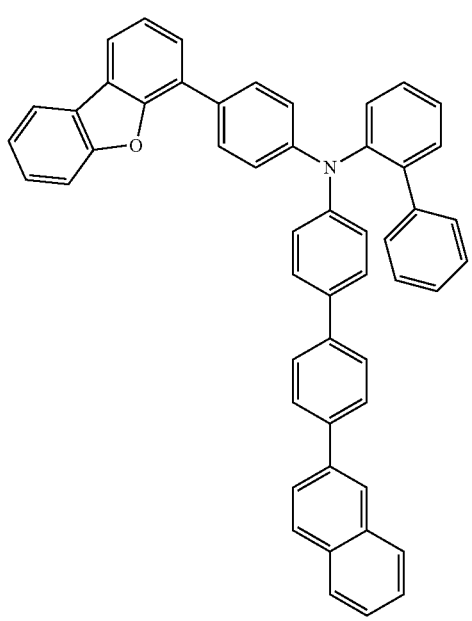
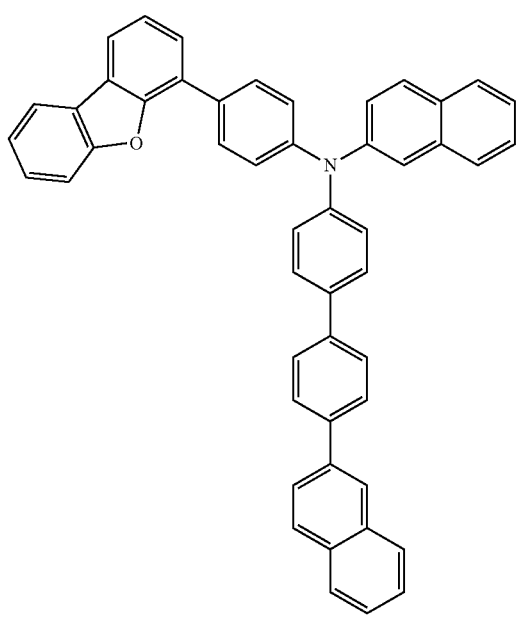

65
-continued
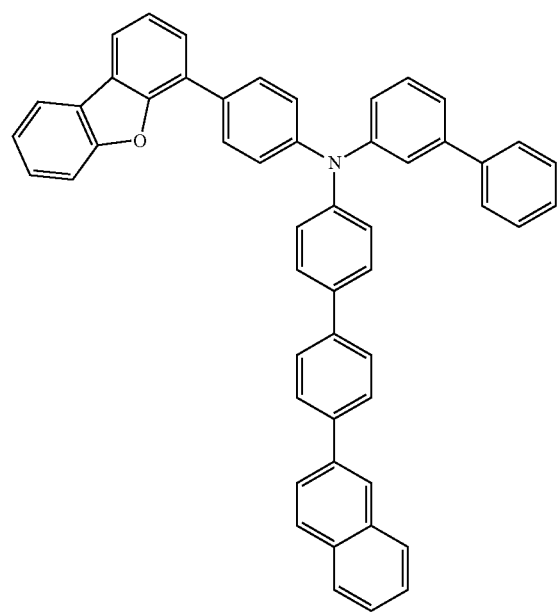
66
-continued
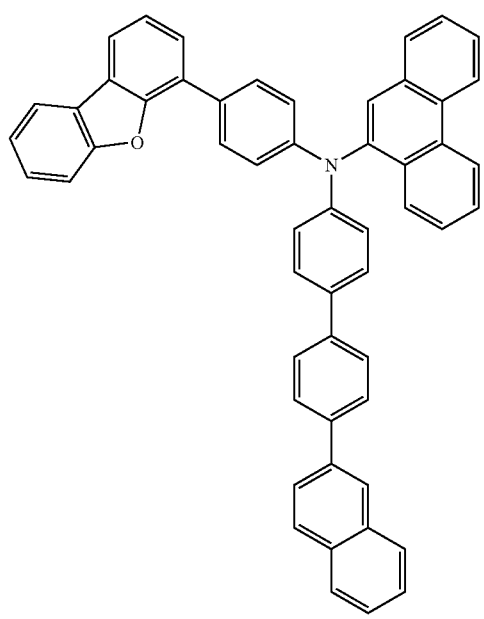
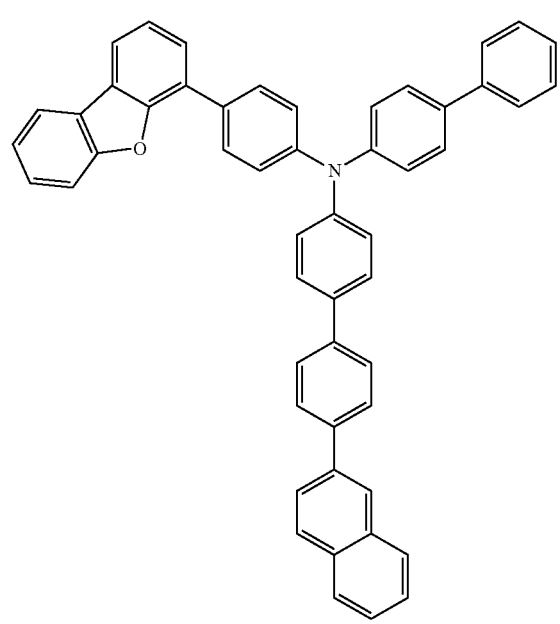
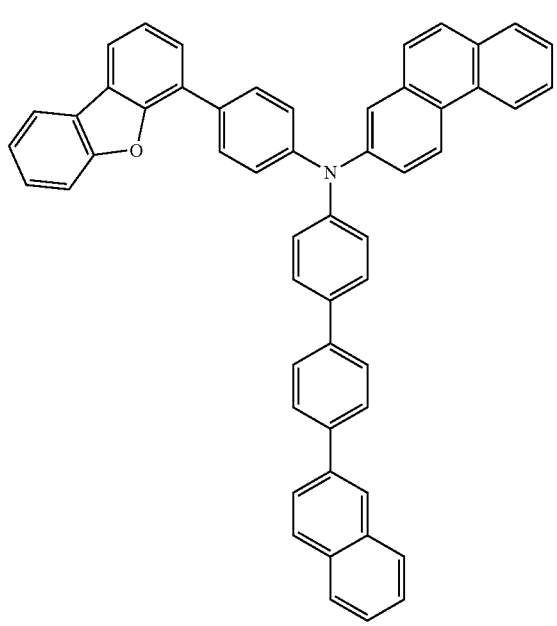

67
-continued
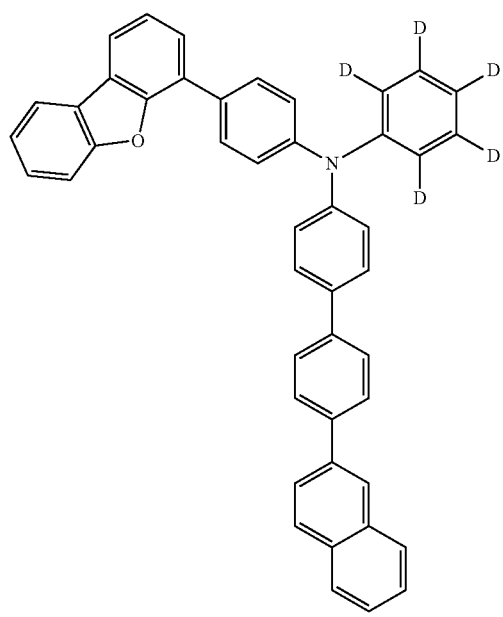
68
-continued
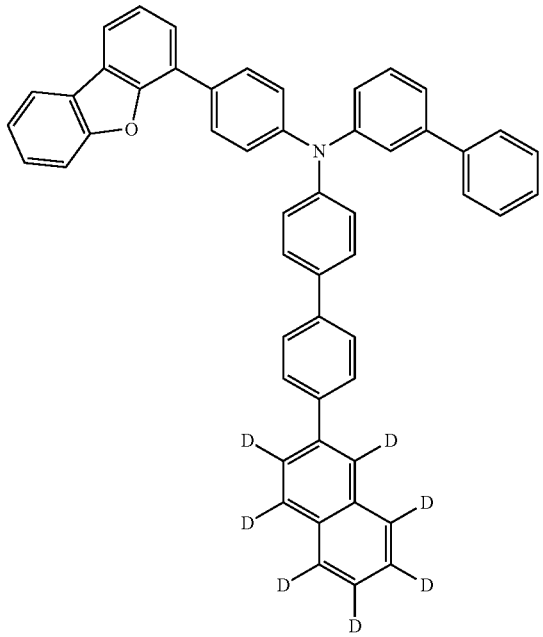
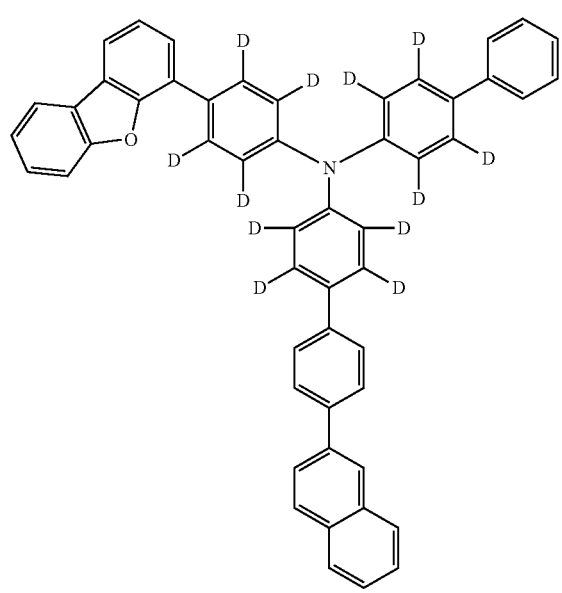
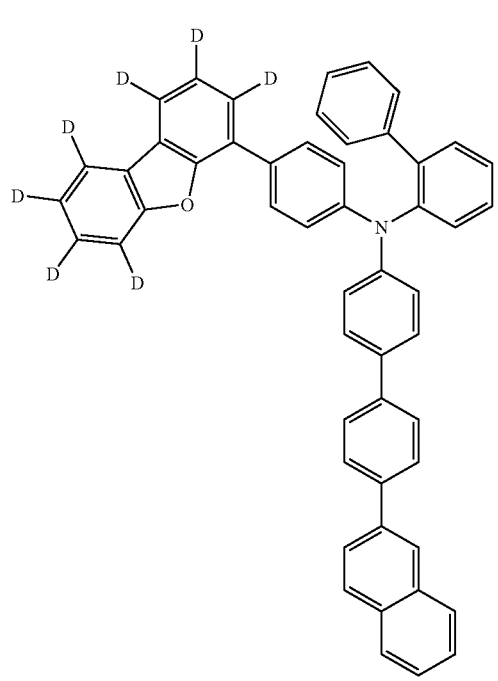

69
-continued
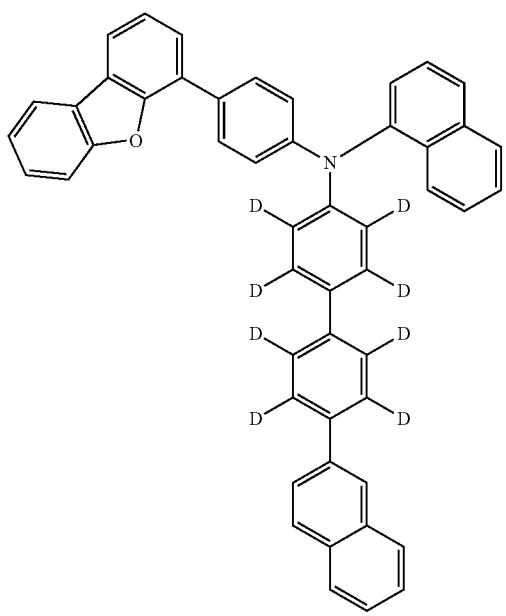
70
-continued
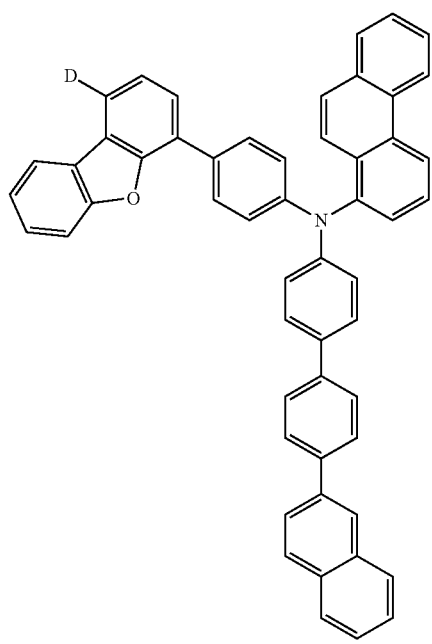
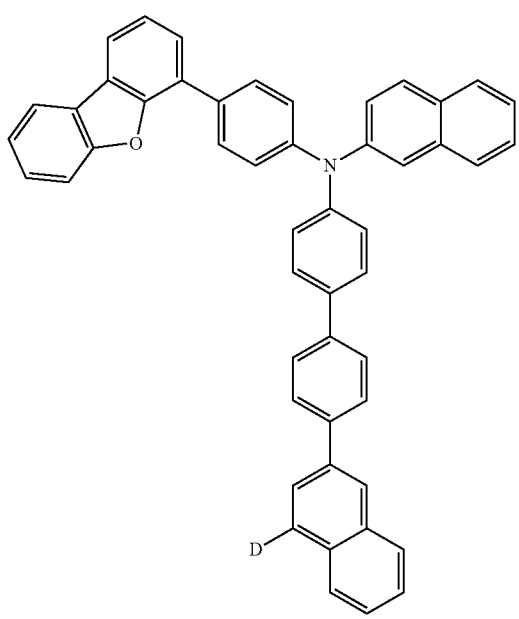
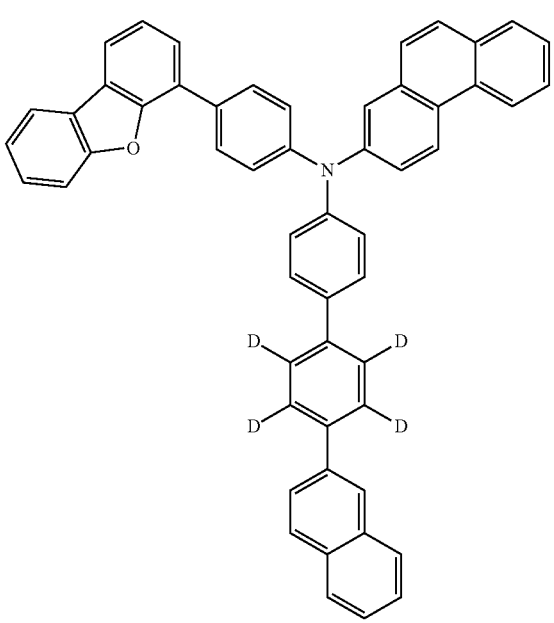

71
-continued

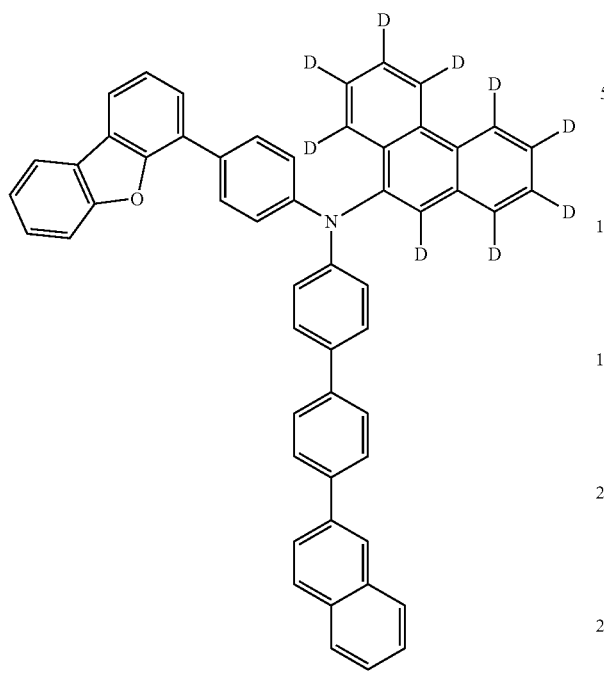

72
-continued

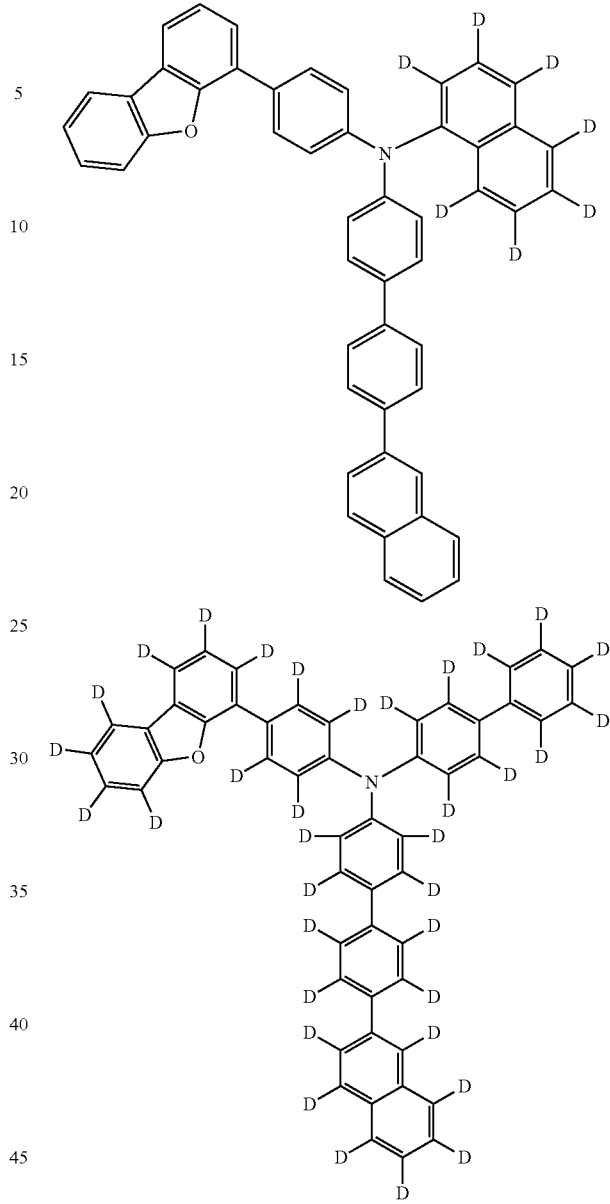

Material for Organic Electroluminescence Devices

The material for organic electroluminescence devices comprises the inventive compound. The content of the inventive compound in the material for organic electroluminescence devices is, for example, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%). The material for organic electroluminescence devices is useful for the production of an organic EL device.

Organic Electroluminescence Device

The organic electroluminescence device of the invention comprises an anode, a cathode, and an organic layer disposed between the anode and the cathode. The organic layer comprises a light emitting layer and at least one layer of the organic layer comprises the inventive compound.

Examples of the organic layer which comprises the inventive compound include a hole transporting region formed between an anode and a light emitting layer, such as a hole transporting layer, a hole injecting layer, an electron blocking layer, and an exciton blocking layer, a light emitting layer, a space layer, and an electron transporting region formed between a cathode and a light emitting layer, such as an electron transporting layer, an electron injecting layer, and a hole blocking layer, although not limited thereto. The inventive compound is used for the production of a fluorescent or phosphorescent EL device preferably as a material for a hole transporting region or a light emitting layer, more preferably as a material for a hole transporting region, still more preferably as a material for a hole transporting layer, an electron blocking layer or an exciton blocking layer, and particularly preferably an electron blocking layer or an exciton blocking layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a multi-layered structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer/Electron transporting layer(/Electron injecting layer);

(b) (Hole injecting layer/)Hole transporting layer/Phosphorescent emitting layer/Electron transporting layer(/Electron injecting layer);

(c) (Hole injecting layer/)Hole transporting layer/First fluorescent emitting layer/Second fluorescent emitting layer/Electron transporting layer(/Electron injecting layer);

(d) (Hole injecting layer/)Hole transporting layer/First phosphorescent emitting layer/Second phosphorescent emitting layer/Electron transporting layer(/Electron injecting layer);

(e) (Hole injecting layer/)Hole transporting layer/Phosphorescent emitting layer/Space layer/Fluorescent emitting layer/Electron transporting layer(/Electron injecting layer);

(f) (Hole injecting layer/)Hole transporting layer/First phosphorescent emitting layer/Second phosphorescent emitting layer/Space layer/Fluorescent emitting layer/Electron transporting layer(/Electron injecting layer);

(g) (Hole injecting layer/)Hole transporting layer/First phosphorescent emitting layer/Space layer/Second phosphorescent emitting layer/Space layer/Fluorescent emitting layer/Electron transporting layer(/Electron injecting layer);

(h) (Hole injecting layer/)Hole transporting layer/Phosphorescent emitting layer/Space layer/First fluorescent emitting layer/Second fluorescent emitting layer/Electron transporting layer(/Electron injecting layer);

(i) (Hole injecting layer/)Hole transporting layer/Electron blocking layer/Fluorescent emitting layer/Electron transporting layer(/Electron injecting layer);

(j) (Hole injecting layer/)Hole transporting layer/Electron blocking layer/Phosphorescent emitting layer/Electron transporting layer(/Electron injecting layer);

(k) (Hole injecting layer/)Hole transporting layer/Exciton blocking layer/Fluorescent emitting layer/Electron transporting layer(/Electron injecting layer);

(l) (Hole injecting layer/)Hole transporting layer/Exciton blocking layer/Phosphorescent emitting layer/Electron transporting layer(/Electron injecting layer);

(m) (Hole injecting layer/)First hole transporting layer/Second hole transporting layer/Fluorescent emitting layer/Electron transporting layer(/Electron injecting layer);

(n) (Hole injecting layer/)First hole transporting layer/Second hole transporting layer/Phosphorescent emitting layer/Electron transporting layer(/Electron injecting layer);

(o) (Hole injecting layer/)First hole transporting layer/Second hole transporting layer/Fluorescent emitting layer/First electron transporting layer/Second electron transporting layer(/Electron injecting layer);

(p) (Hole injecting layer/)First hole transporting layer/Second hole transporting layer/Phosphorescent emitting layer/First electron transporting layer/Second electron transporting layer(/Electron injecting layer);

(q) (Hole injecting layer/)Hole transporting layer/Fluorescent emitting layer/Hole blocking layer/Electron transporting layer(/Electron injecting layer/Electron injecting layer);

(r) (Hole injecting layer/)Hole transporting layer/Phosphorescent emitting layer/Hole blocking layer/Electron transporting layer(/Electron injecting layer);

(s) (Hole injecting layer/)Hole transporting layer/Fluorescent emitting layer/Exciton blocking layer/Electron transporting layer(/Electron injecting layer); and (t) (Hole injecting layer/)Hole transporting layer/Phosphorescent emitting layer/Exciton blocking layer/Electron transporting layer(/Electron injecting layer).

The emission colors of phosphorescent emitting layers or fluorescent emitting layers may be different. For example, the emission unit (f) may be (Hole injecting layer/)Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer supplies electrons to the first emission unit and holes to the second emission unit and may be formed by known materials.

FIG. 1 is a schematic illustration showing the structure of an example of the organic EL device of the invention, wherein the organic EL device 1 comprises a substrate 2, an anode 3, a cathode 4, and an emission unit 10 disposed between the anode 3 and the cathode 4. The emission unit 10 comprises a light emitting layer 5. A hole transporting region 6 (for example, a hole injecting layer or a hole transporting layer) is disposed between the light emitting layer 5 and the anode 3, and an electron transporting region 7 (for example, an electron injecting layer or an electron transporting layer) is disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

Figure 2:
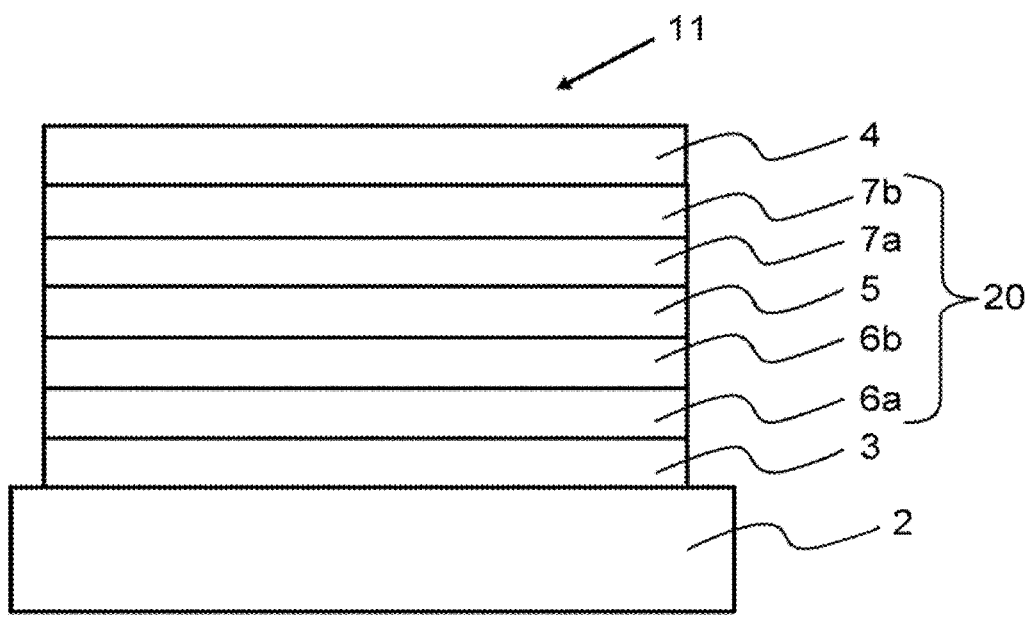
FIG. 2 is a schematic view showing the layered structure of an organic EL device in another embodiment of the invention.

FIG. 2 is a schematic illustration showing the structure of another example of the organic EL device, wherein the organic EL device 11 comprises a substrate 2, an anode 3, a cathode 4, and an emission unit 20 disposed between the anode 3 and the cathode 4. The emission unit 20 comprises a light emitting layer 4. The hole transporting region disposed between the anode 3 and the light emitting layer 5 is formed by a first hole transporting layer 6a and a second hole transporting layer 6b. The electron transporting region disposed between the light emitting layer 5 and the cathode 4 is formed by a first electron transporting layer 7a and a second electron transporting layer 7b.

In the present invention, a host is referred to as a fluorescent host when combinedly used with a fluorescent dopant (fluorescent emitting material) and as a phosphorescent host when combinedly used with a phosphorescent dopant (phosphorescent emitting material). Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium and ytterbium, and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material) and formed between an anode and a light emitting layer or between an anode and a hole transporting layer, if present.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting layer material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide](PTPDMA), and poly[N,N'-bis(4-butylphenyl)-N,N'-bis(phenyl)benzidine] (Poly-TPD). A macromolecular compound doped with an acid, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used:

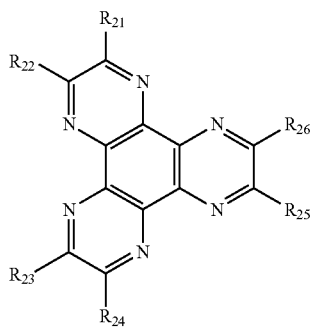

(K)

wherein:

$R_{21}$ to $R_{26}$ are each independently a cyano group, —$CONH_2$, a carboxyl group, or —$COOR_{27}$ wherein $R_{27}$ is an alkyl group having 1 to 20 carbon atoms or a cycloalkyl group having 3 to 20 ring carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material) and formed between an anode and a light emitting layer or between a hole injecting layer, if present, and a light emitting layer. The inventive compound is preferably used in a hole transporting layer alone or in combination with the compound described below.

The hole transporting layer may be a single layer or a multi-layer of two or more layers. For example, the hole transporting layer may be a two-layered structure comprising a first hole transporting layer (anode side) and a second hole transporting layer (cathode side). In an embodiment of the invention, a hole transporting layer of a single-layered structure is preferably in contact with a light emitting layer and a hole transporting layer in a multi-layered structure which is closest to a cathode, for example, the second hole transporting layer in the two-layered structure mentioned above, is preferably in contact with a light emitting layer. In another embodiment of the invention, an electron blocking layer may be disposed between the light emitting layer and the hole transporting layer of the single-layered structure or between the light emitting layer and the hole transporting layer in the multi-layered structure which is closest to the light emitting layer.

In the two-layered structure of the hole transporting layer, the inventive compound may be included in one or both of the first hole transporting layer and the second hole transporting layer. In an embodiment of the invention, the inventive compound is preferably used in the first hole transporting layer. In another embodiment, the inventive compound is preferably used in the second hole transporting layer. In still another embodiment, the inventive compound is preferably used in both the first hole transporting layer and the second hole transporting layer.

In an embodiment of the invention, the inventive compound used in one or both of the first hole transporting layer and the second hole transporting layer is preferably a light-hydrogen analogue in view of production cost.

The light-hydrogen analogue means the inventive compound wherein all the hydrogen atoms are light hydrogen atoms.

Thus, the present invention includes an organic EL device comprising the inventive compound in one or both of the first hole transporting layer and the second hole transporting layer, wherein the inventive compound is substantially a light-hydrogen analogue. The words "the inventive compound is substantially a light-hydrogen analogue" used herein means that the content of the light-hydrogen analogue in the total amount of the inventive compound is 90 mol % or more, preferably 95 mol % or more, and still more preferably 99 mol % or, each inclusive of 100%.

Examples of the hole transporting material other than the inventive compound includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ $cm^2/Vs$ or more.

Examples of the carbazole derivative include 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA).

Examples of the anthracene derivative include 2-t-butyl-9,10-di(2-naphthyl)anthracene (t-BuDNA), 9,10-di(2-naphthyl)anthracene (DNA), and 9,10-diphenylanthracene (DPAnth).

In addition, a macromolecular compound, such as poly(N-vinylcarbazole) (PVK) and poly(4-vinyltriphenylamine) (PVTPA) are usable.

Compounds other than those mentioned above are also usable, if their hole transporting ability is higher than their electron transporting ability.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carb azole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)s(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The host material preferably has a lowest unoccupied molecular orbital level (LUMO level) higher than that of the dopant material and a highest occupied molecular orbital level (HOMO level) lower than that of the dopant material.

The host material other the compound (1) may include, for example, (1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and
(4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato)aluminum(III) (BAlq), bis(8-quinolinolato)zinc(II) (Znq), bis[2-(2-benzoxazolyl)pheno]atolzinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

In particular, as a host material for a blue fluorescent device, the following anthracene compound is preferably used.

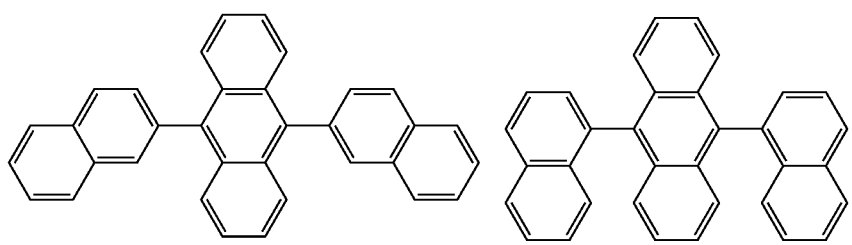

-continued
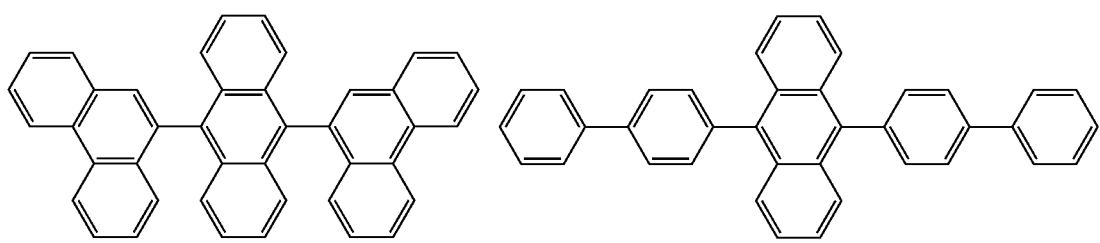
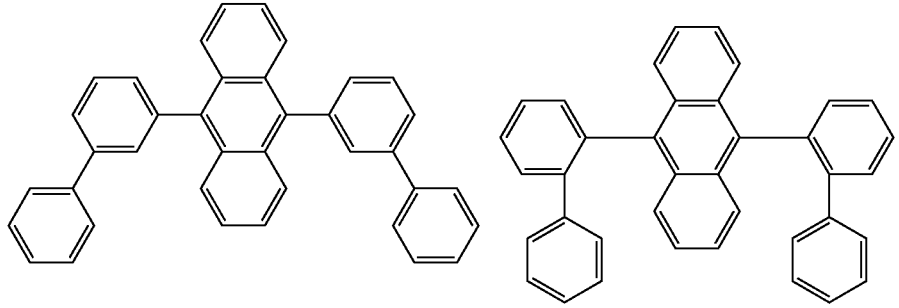
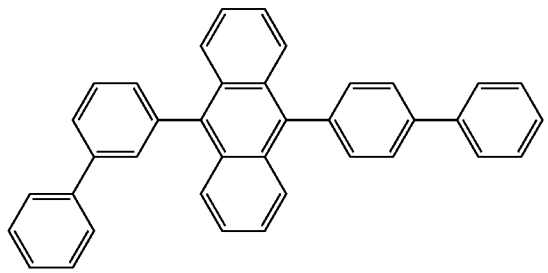
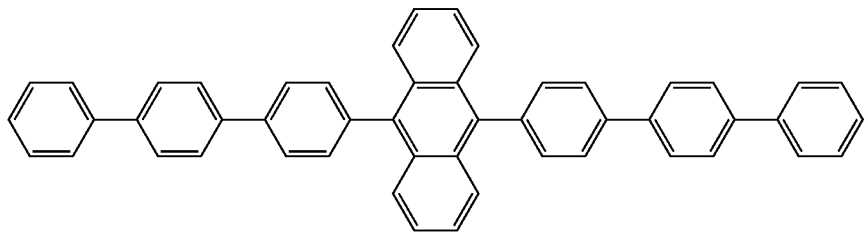
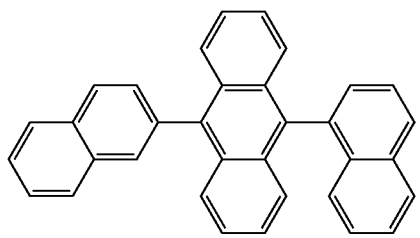
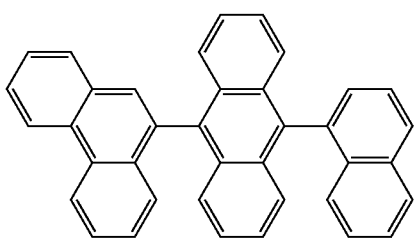
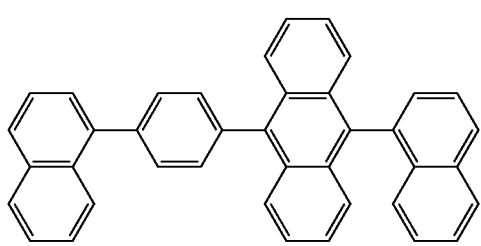
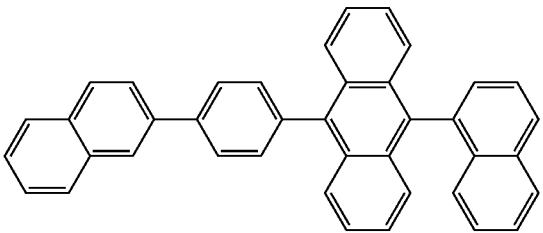

-continued
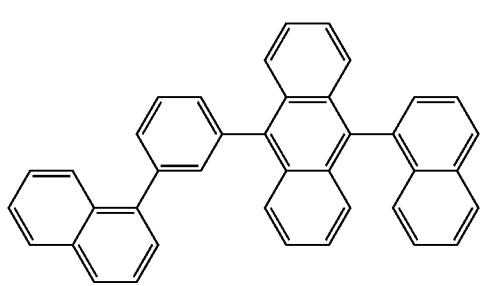
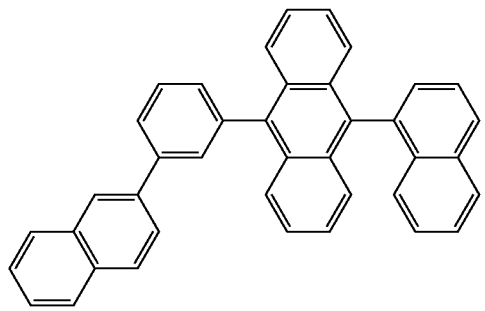
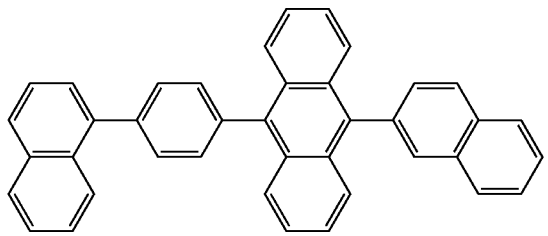
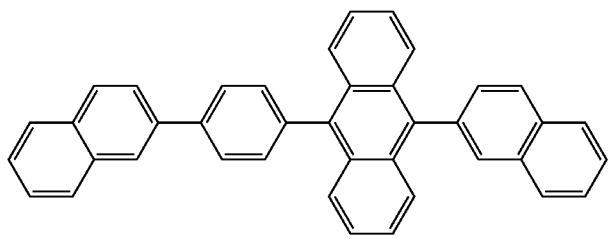
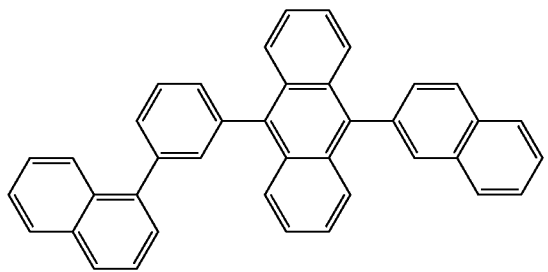
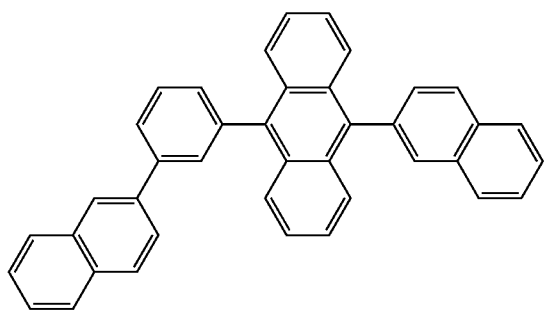
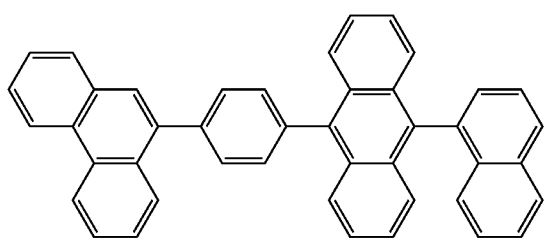
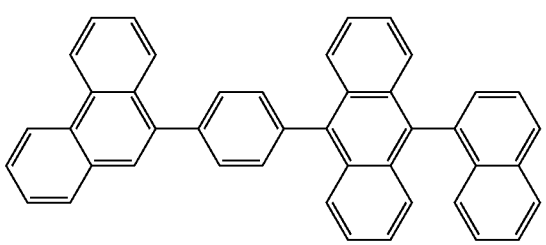
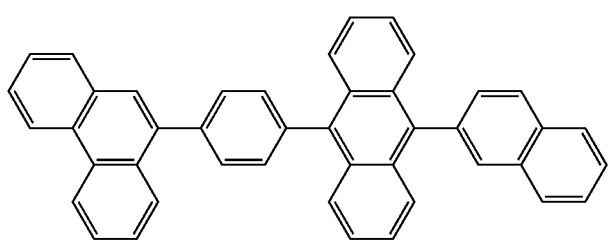

-continued
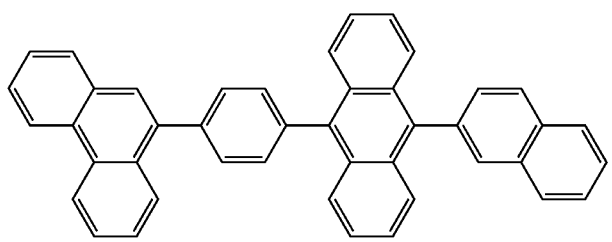
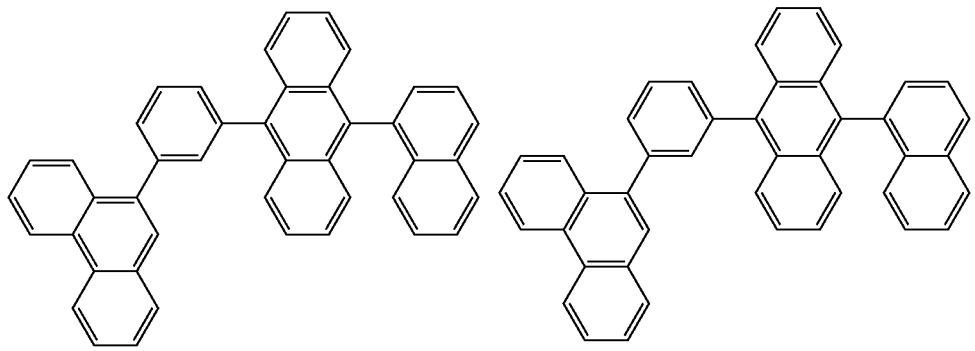
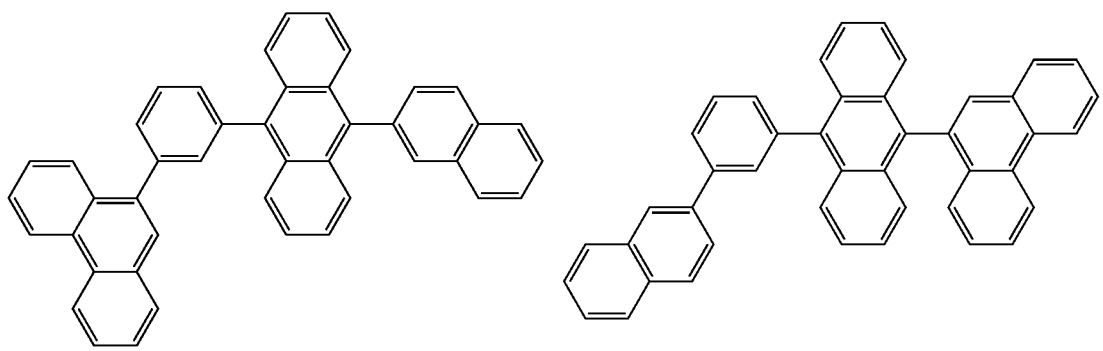
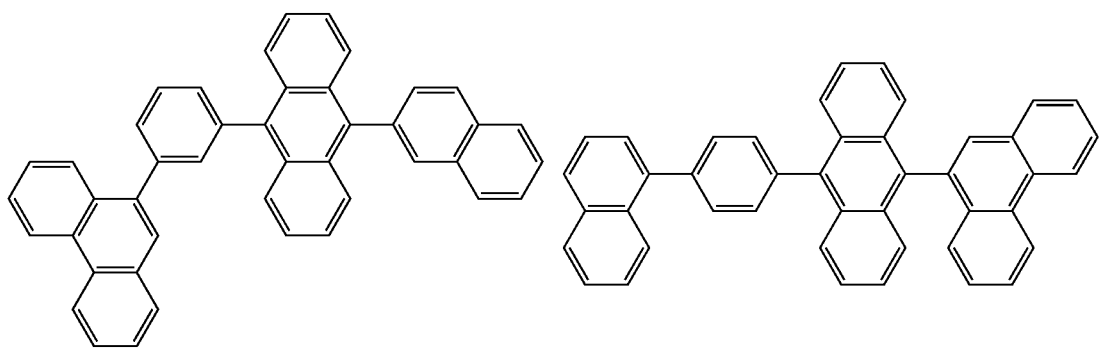
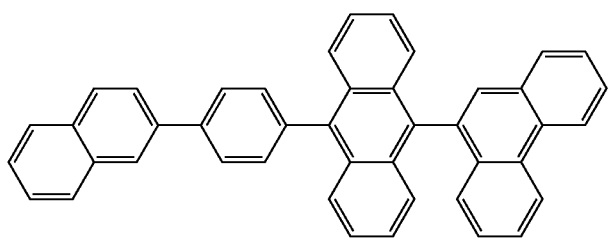

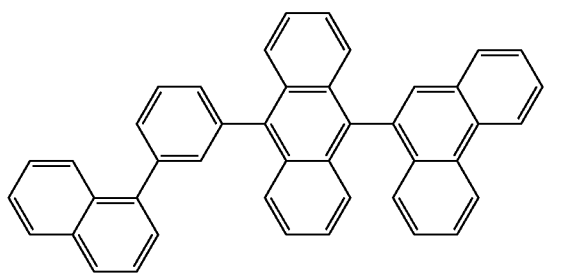
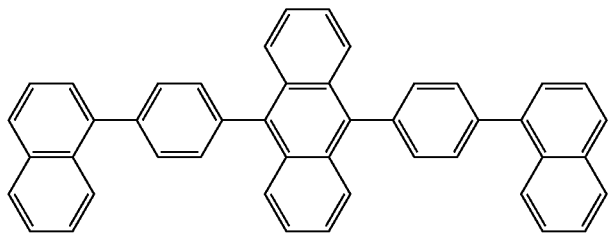
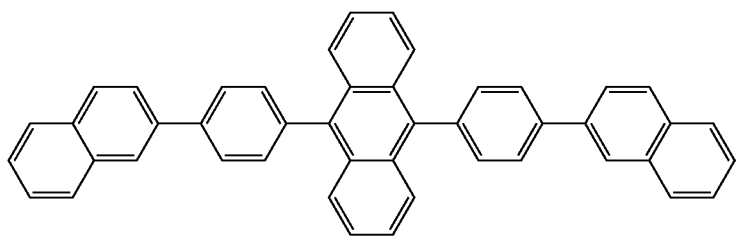
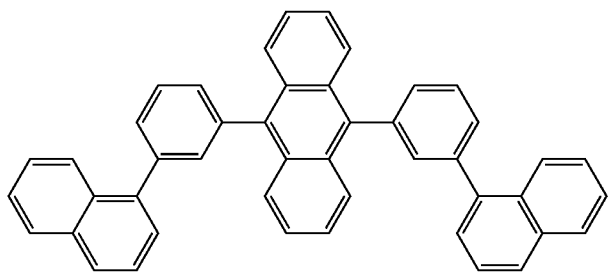
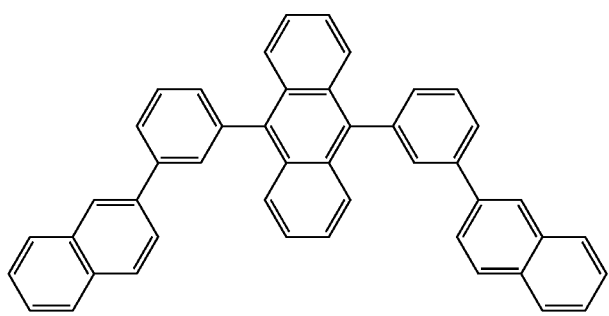
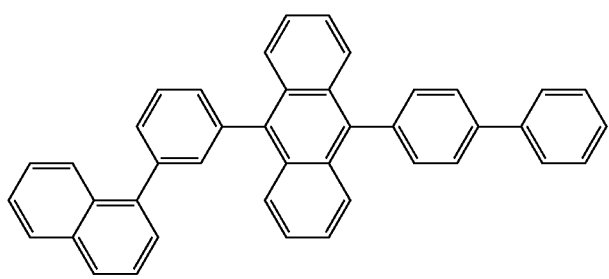

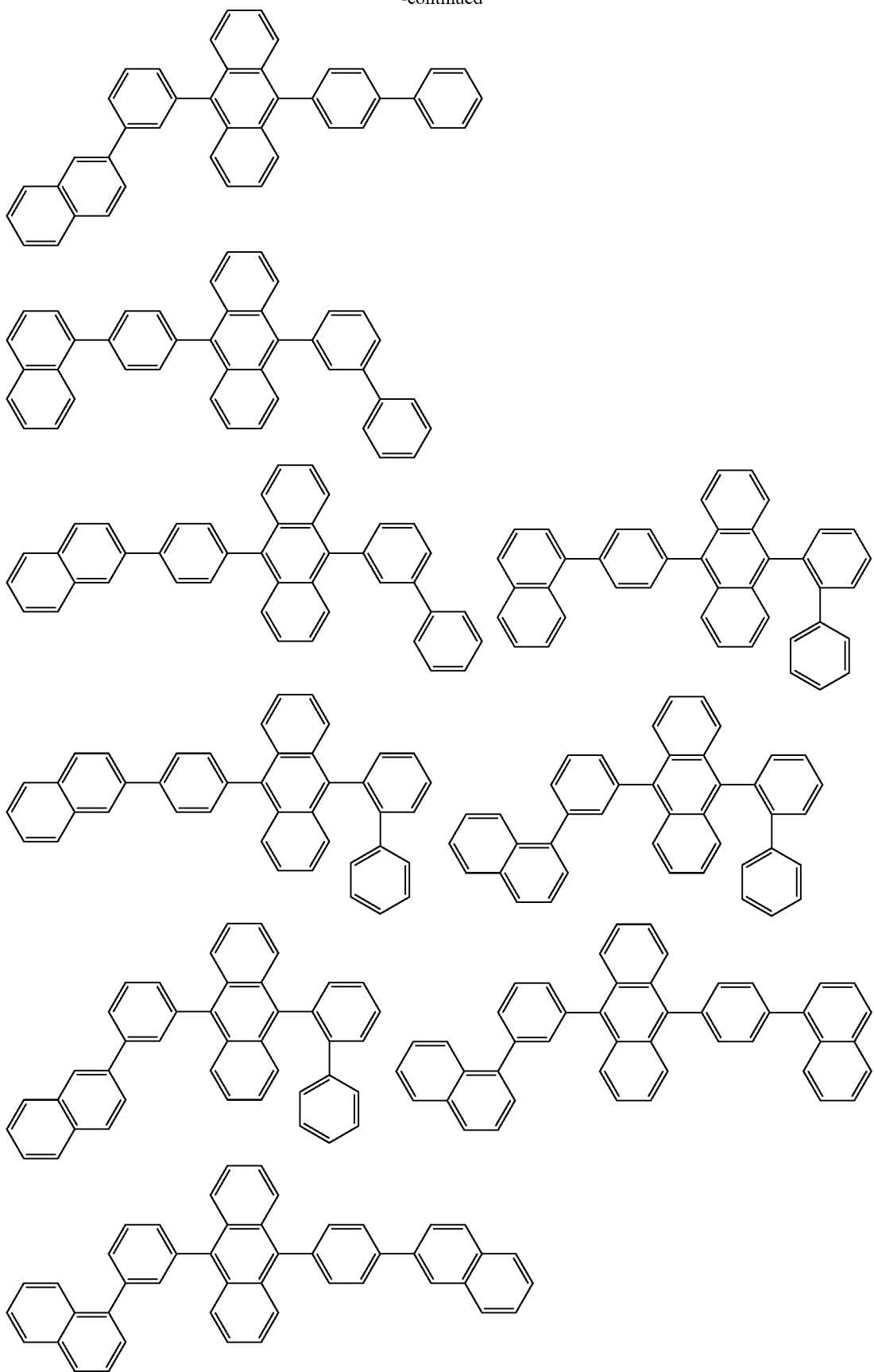

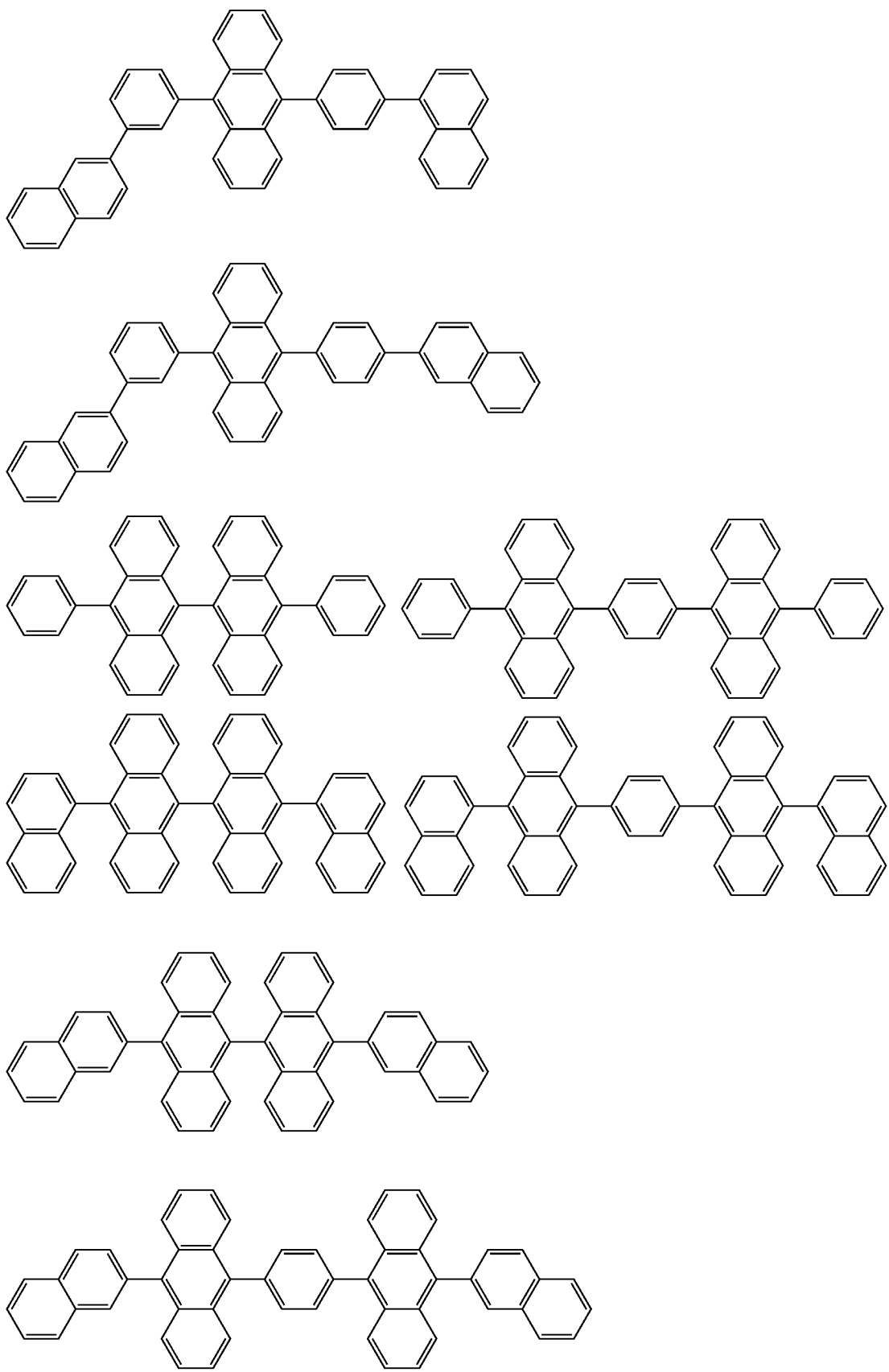

-continued
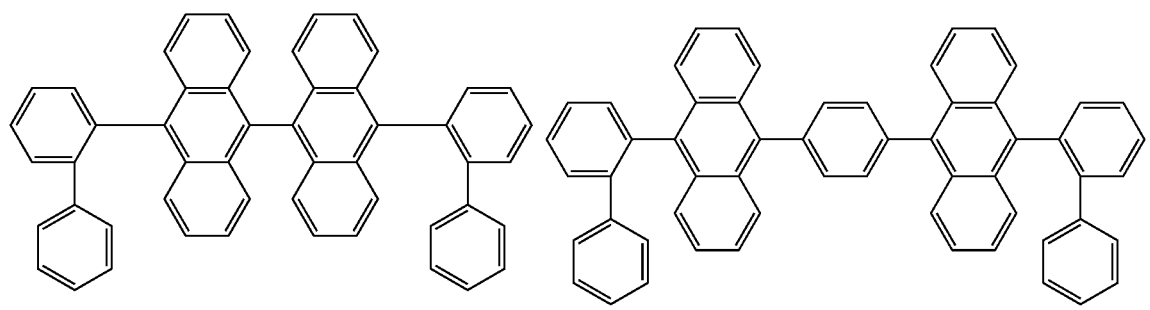
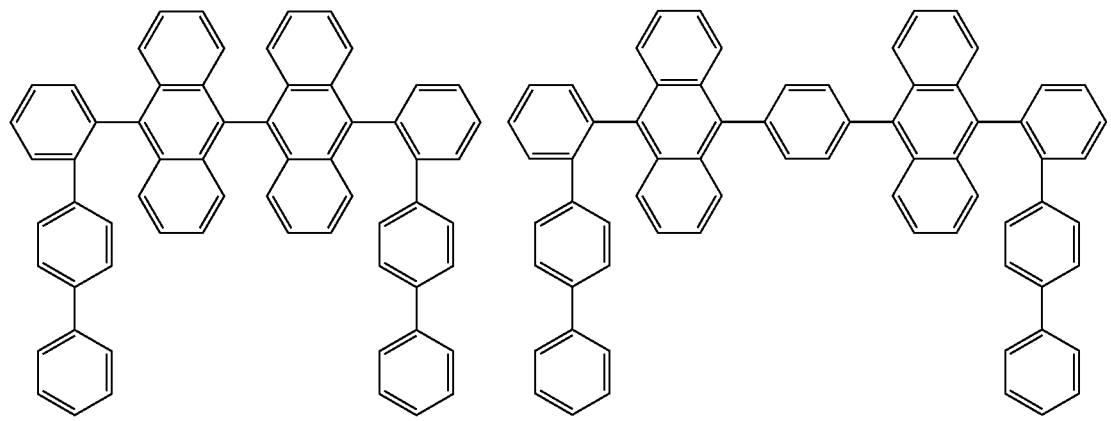
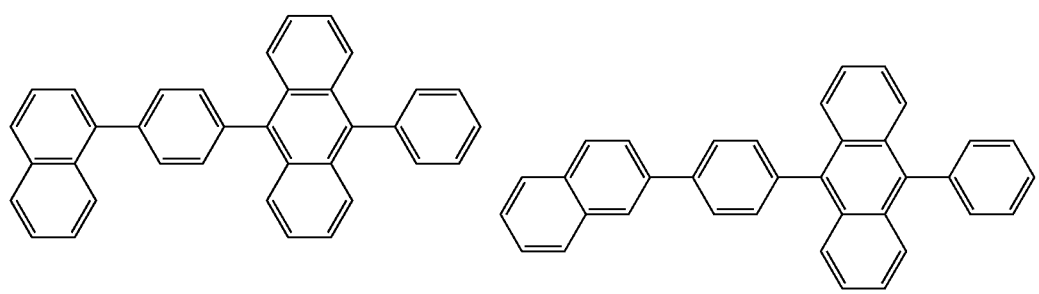
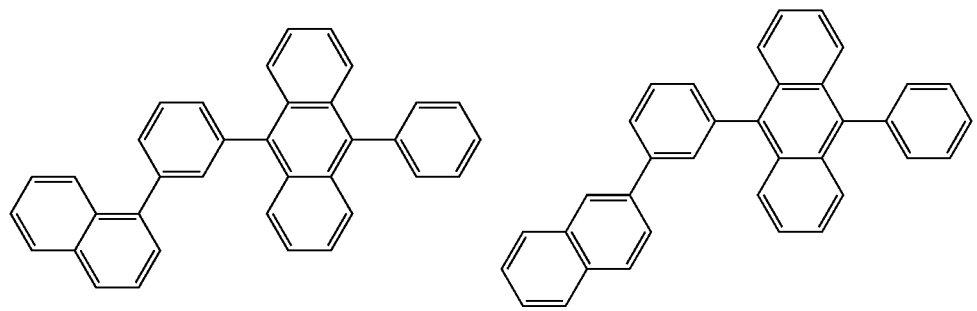
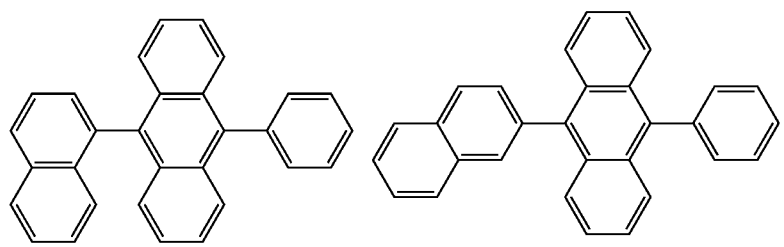

95 96
-continued
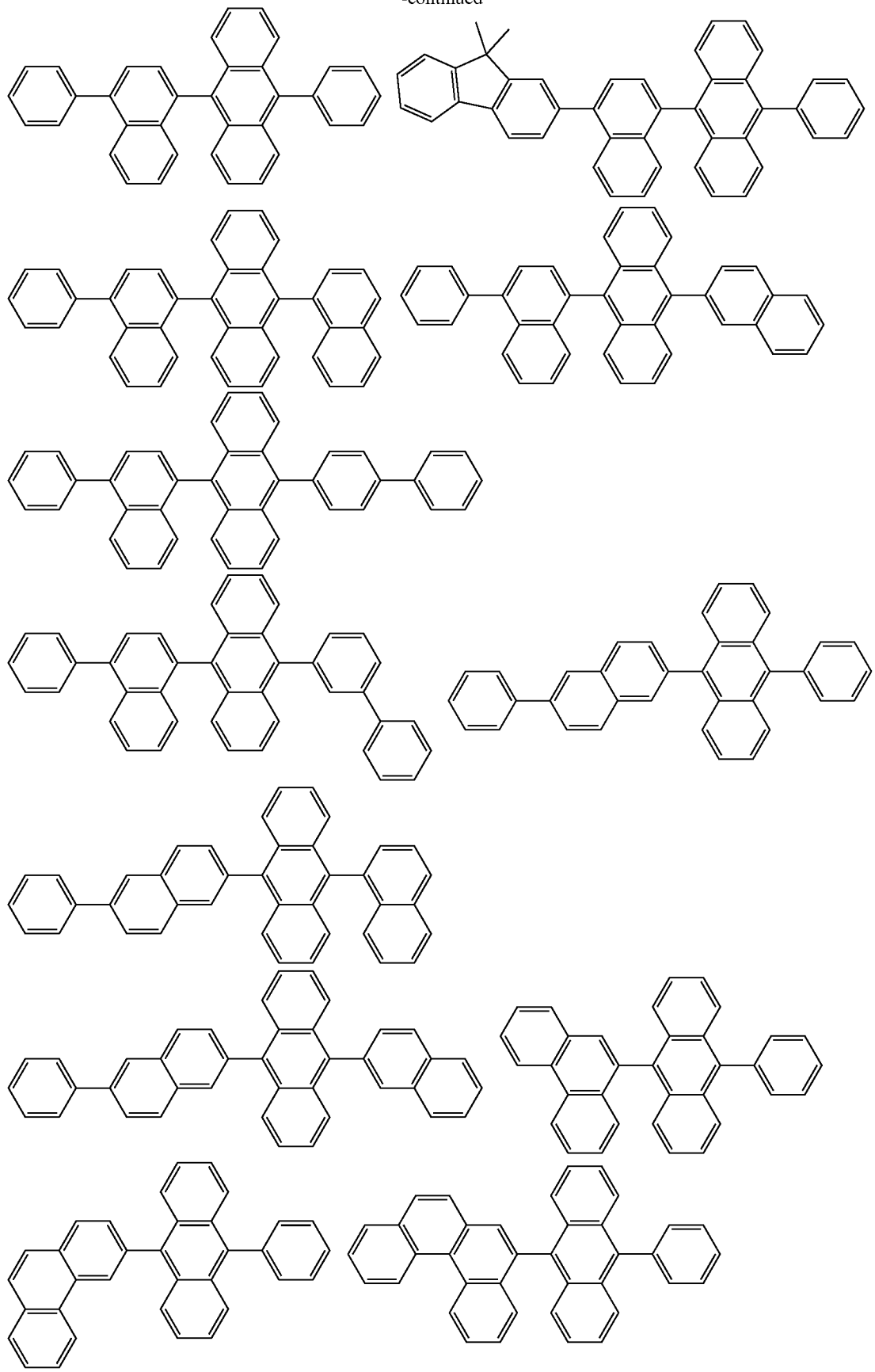

-continued
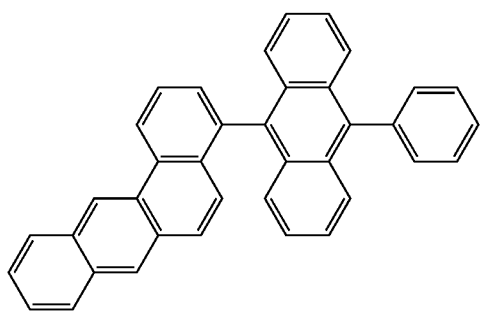

-continued
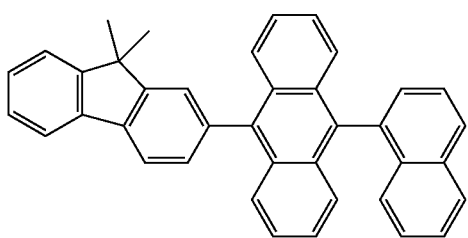
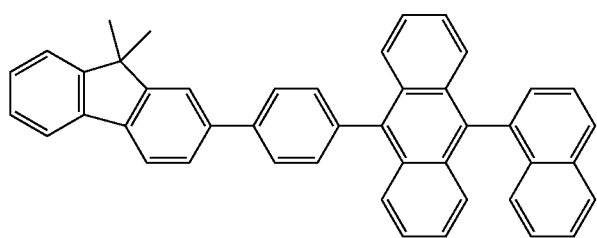
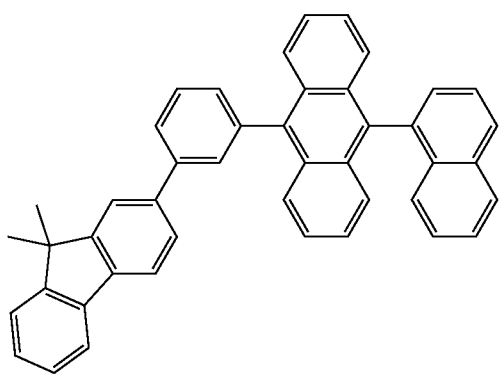
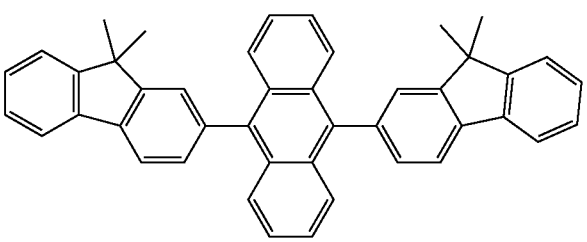
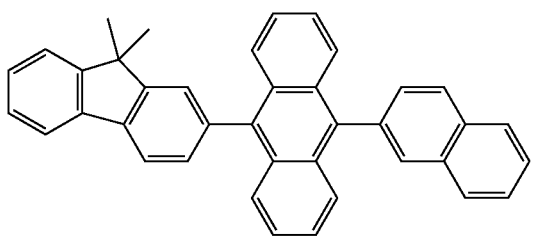
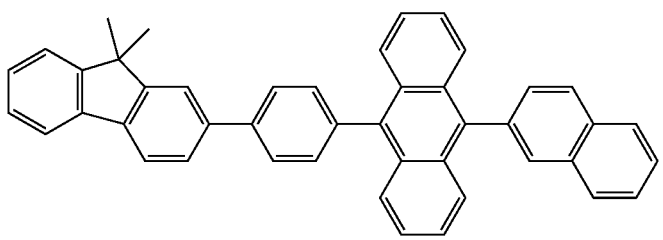
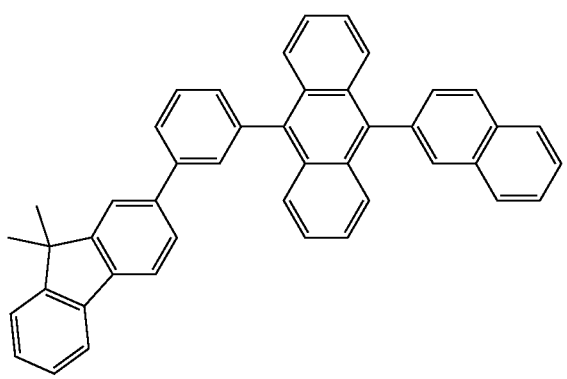

101 102
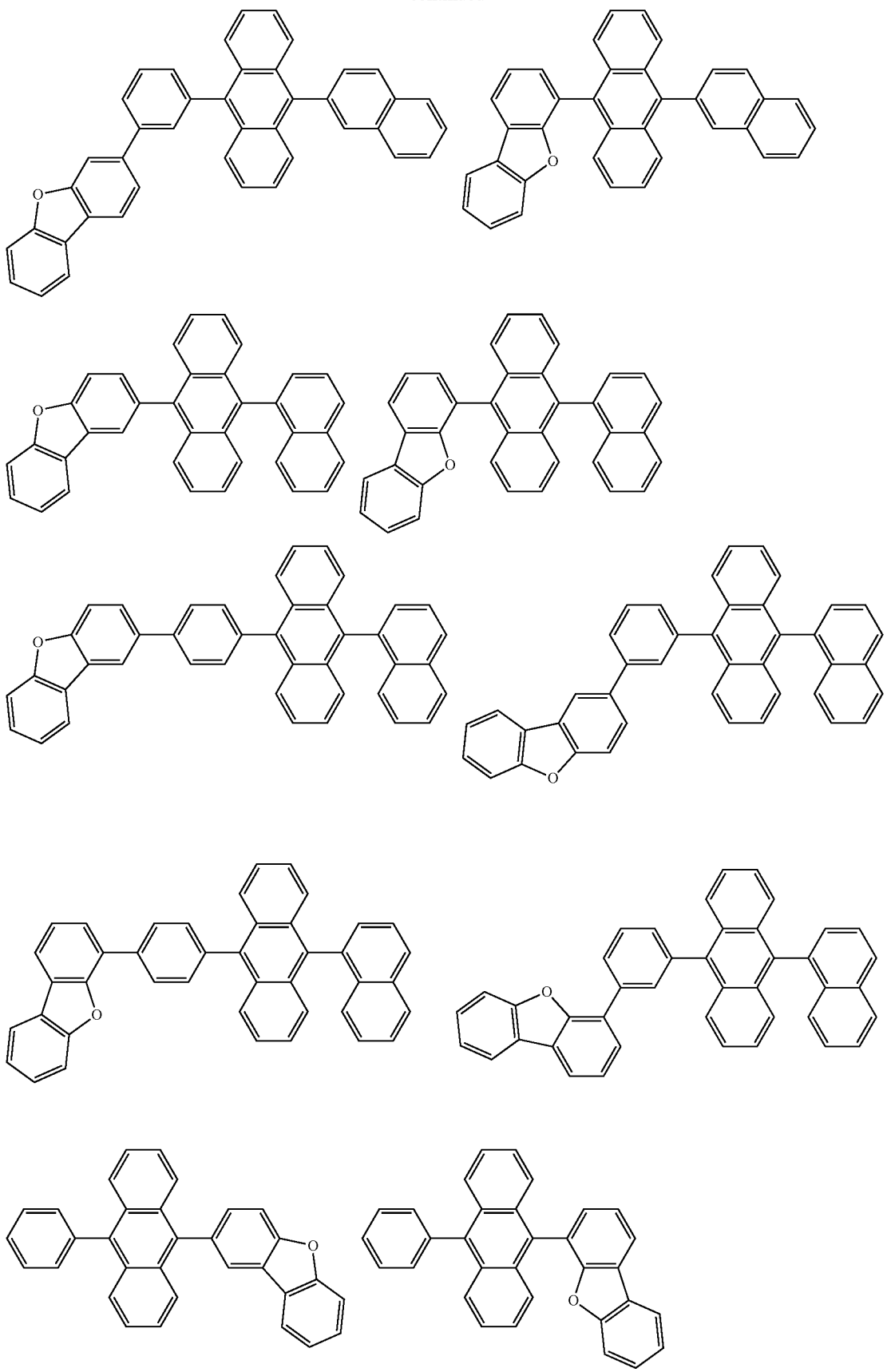
-continued 103 104
-continued
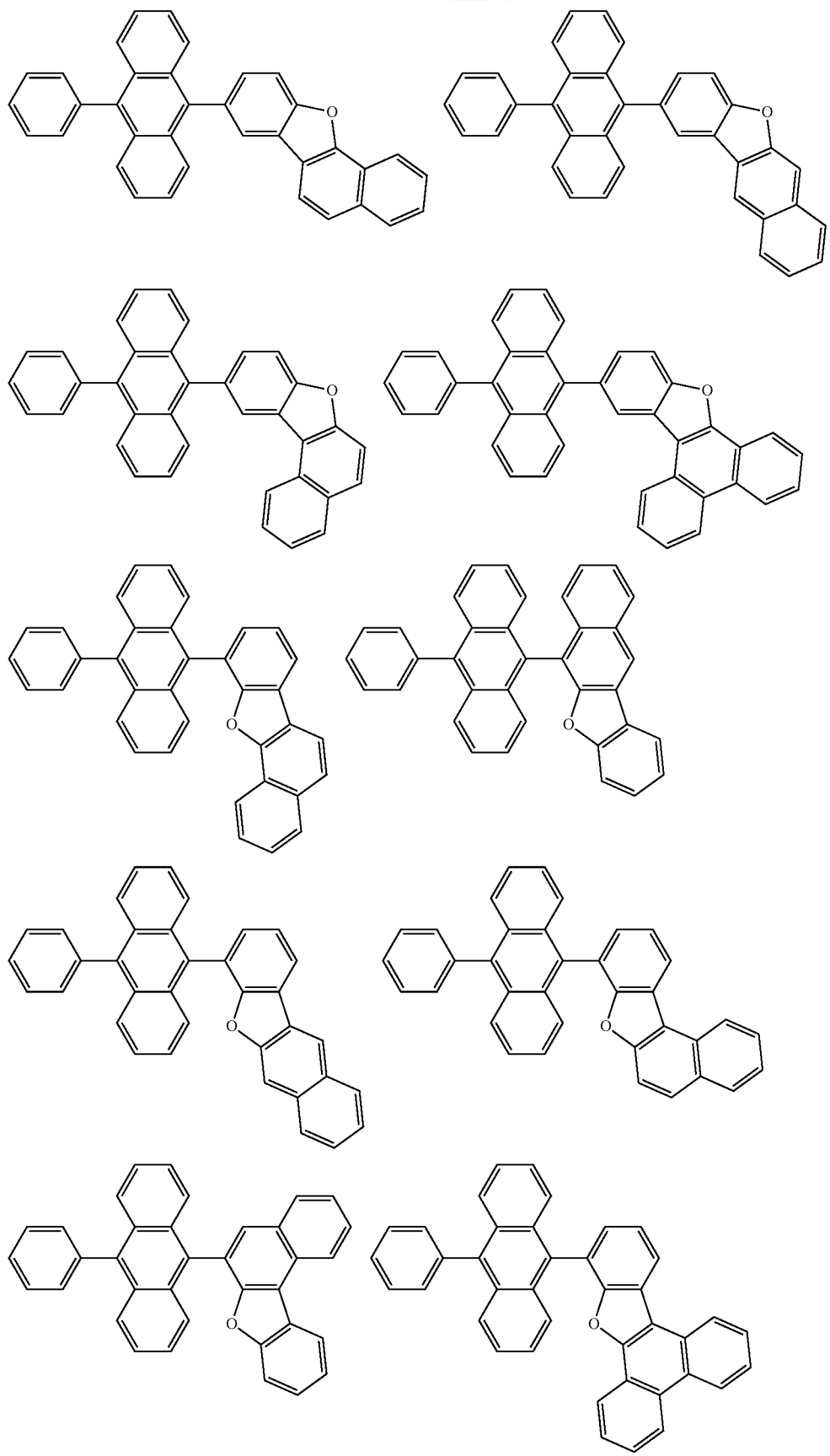

-continued
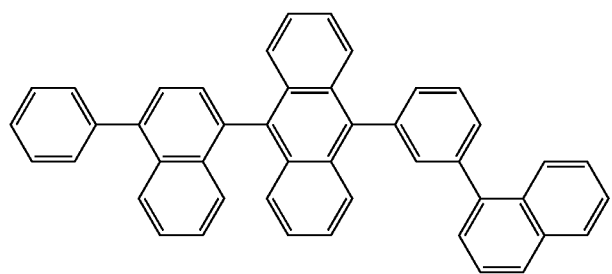
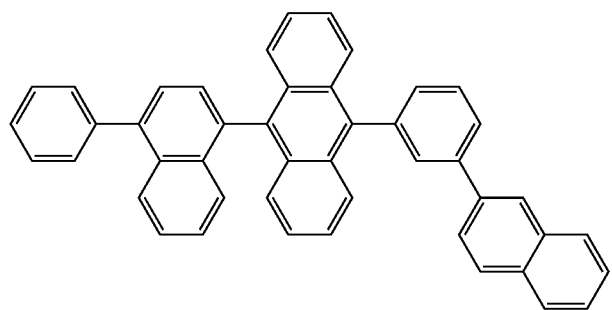
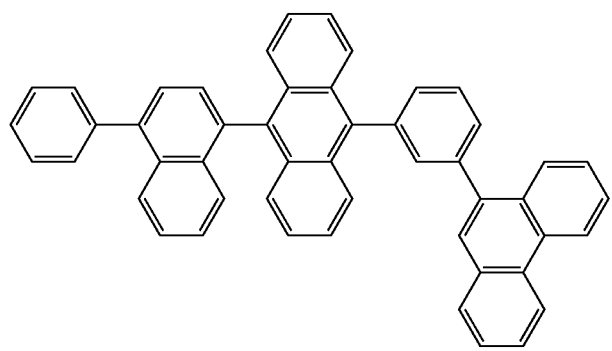
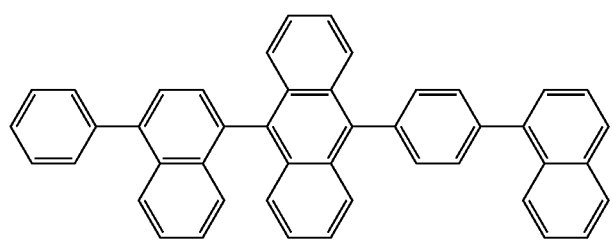
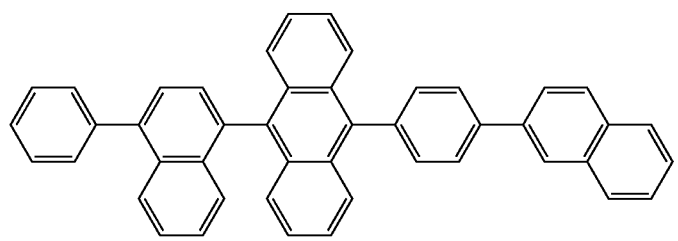
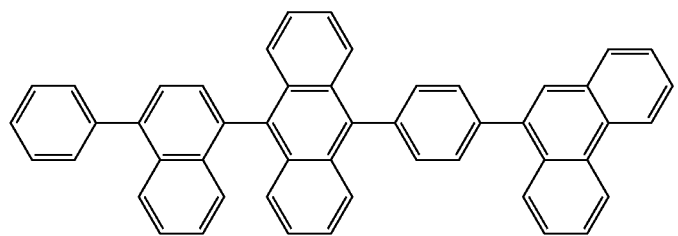

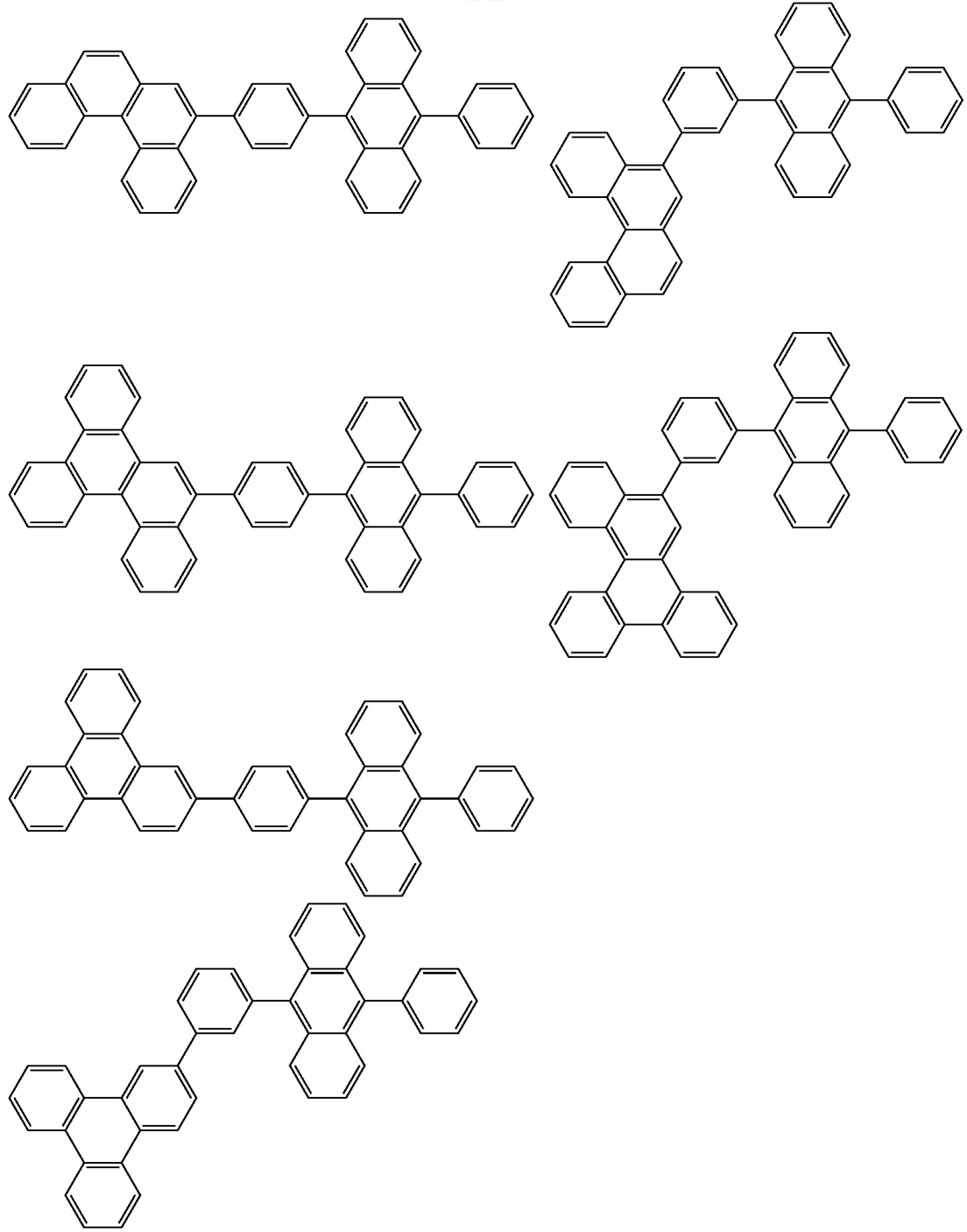

Electron Transporting Layer

The electron transporting layer comprises a material having a high electron transporting ability (electron transporting material) and formed between a light emitting layer and a cathode or between a light emitting layer and an electron injecting layer, if present.

The electron transporting layer may be a single layer or a multi-layer of two or more layers. For example, the electron transporting layer may be a two-layered structure comprising a first electron transporting layer (anode side) and a second electron transporting layer (cathode side). In an embodiment of the invention, an electron transporting layer of a single-layered structure is preferably in contact with a light emitting layer and an electron transporting layer in a multi-layered structure which is closest to an anode, for example, the first electron transporting layer in the two-layered structure mentioned above, is preferably in contact with a light emitting layer. In another embodiment of the invention, an hole blocking layer mentioned below may be disposed between the light emitting layer and the electron transporting layer of the single-layered structure or between the light emitting layer and the electron transporting layer in the multi-layered structure which is closest to the light emitting layer.

The electron transporting layer may be formed, for example, by
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato) aluminum (Almq$_3$), bis(10-hydroxybenzo[h]quinolinato)beryllium (BeBq$_2$), bis(2-methyl-8-quinolinato)(4-phenylphenolato)aluminum (III) (BAlq), bis(8-quinolinato) zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly [(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of $10^{-6}$ cm$^2$/Vs or more. Materials other than those mentioned above are also usable in the electron transporting layer if their electron transporting ability is higher than their hole transporting ability.

Electron Injecting Layer

The electron injecting layer is a layer comprising a material having a high electron injecting ability, for example, an alkali metal, such as lithium (Li), cesium (Cs), an alkaline earth metal, such as magnesium (Mg), calcium (Ca), and strontium (Sr), a rare earth metal, such as europium (Eu) and ytterbium (Yb), and a compound of these metals, such as an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare metal-containing organic complex. These compounds may be used in combination of two or more.

In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the aromatic heterocyclic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of stacked layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier (charge) balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and an exciton blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The exciton blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Compounds Used in the Production of Organic EL Devices of Examples 1 to 6

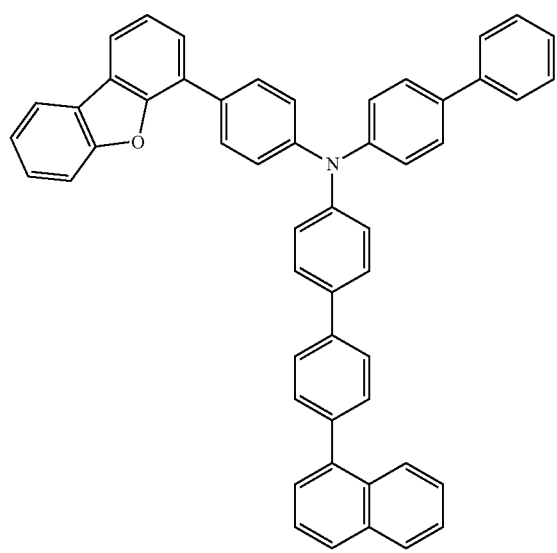

Compound Inv-1

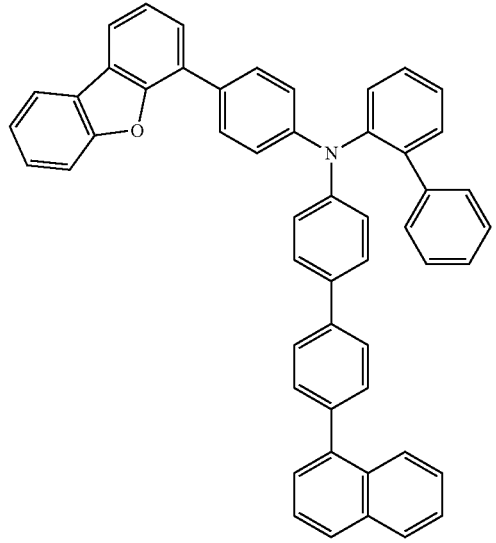

Compound Inv-2

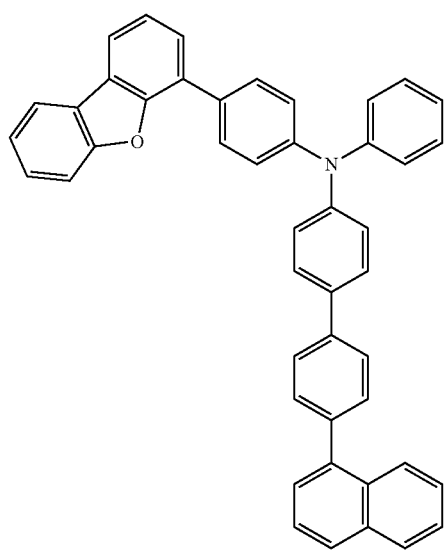

Compound Inv-3

Compound Inv-4
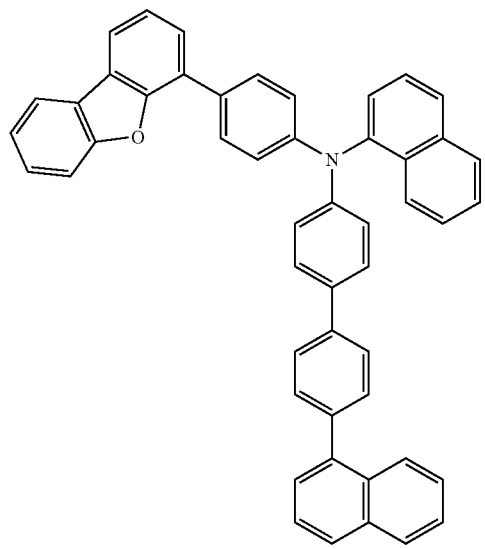
Compound Inv-12
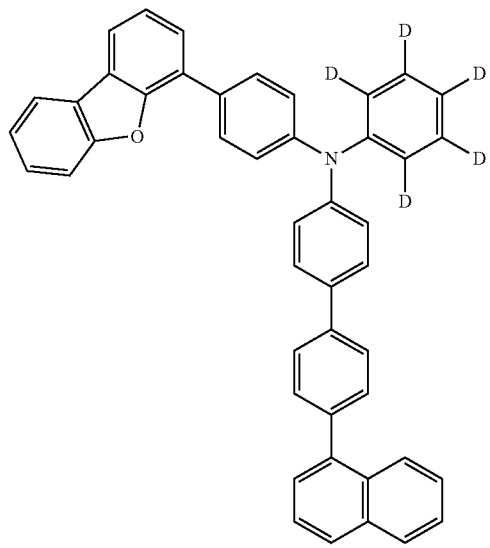
Compound Inv-5
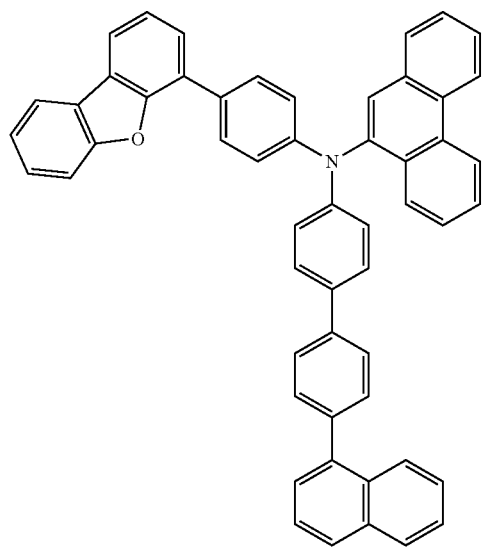
Comparative Compounds Used in the Production of Organic EL Devices of Comparative Examples 1 to 4
Compound Ref-1
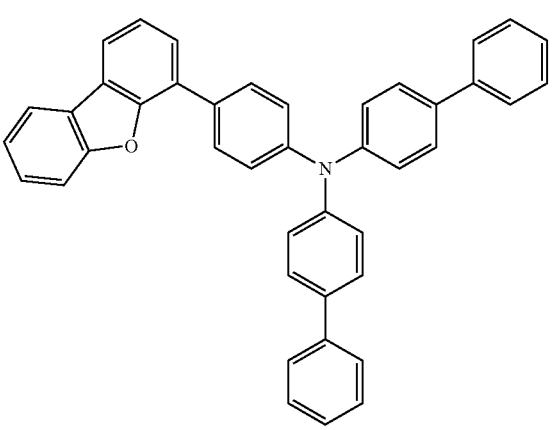

-continued
Compound Ref-2
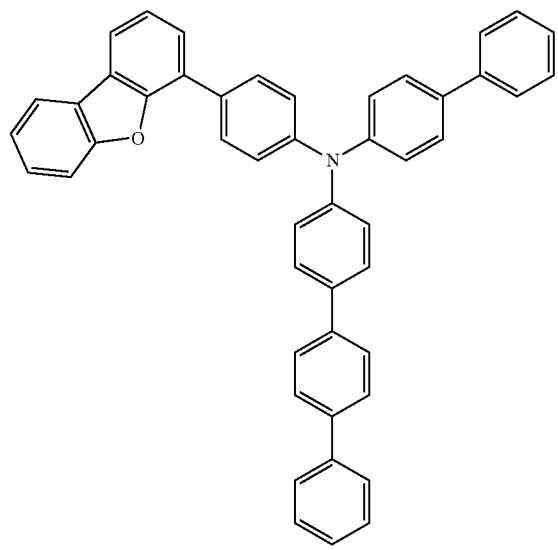
The comparative compound Ref-1 is described in Patent Literature 2 and the comparative compounds Ref-2, Ref-3, and Ref-4 are described in Patent Literature 1.
Other Compounds Used in the Production of Organic EL Devices of Examples 1 to 6 and Comparative Examples 1 to 4
HI-1
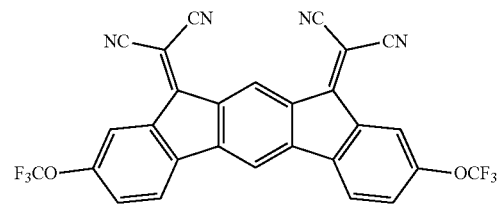
HT-1
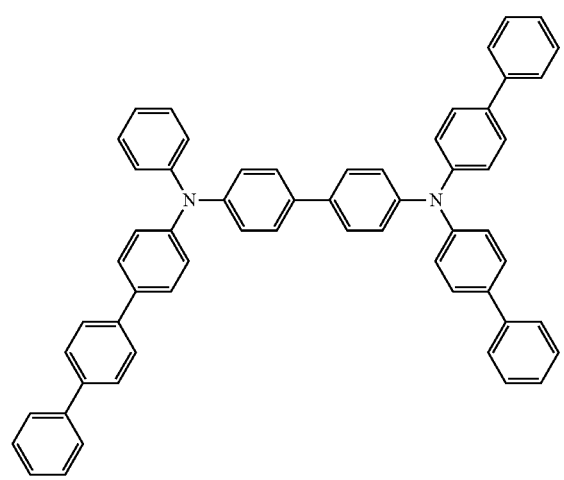
BH-1
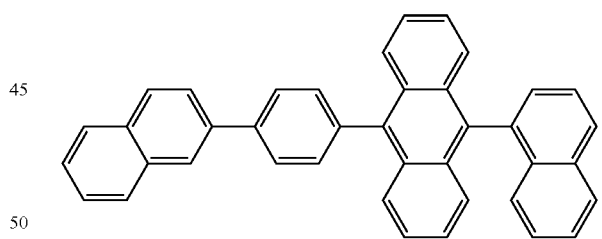
Compound Ref-3
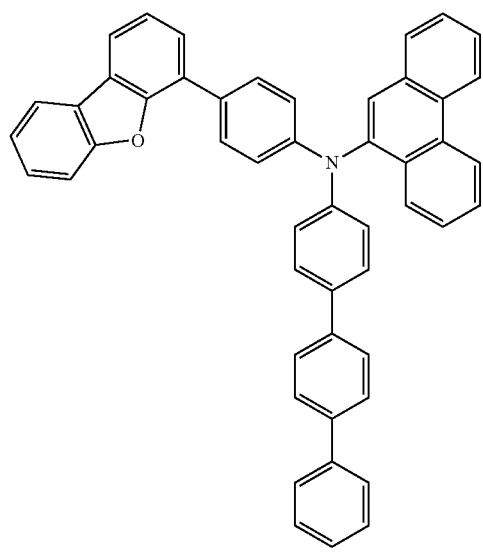
Compound Ref-4
BD-1
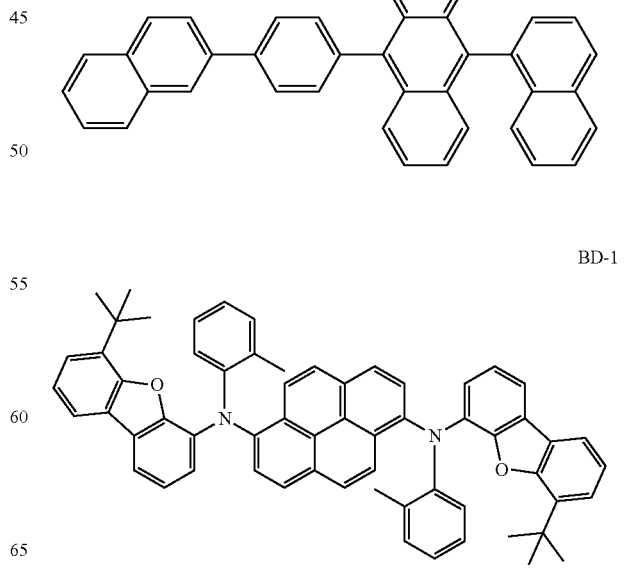

-continued

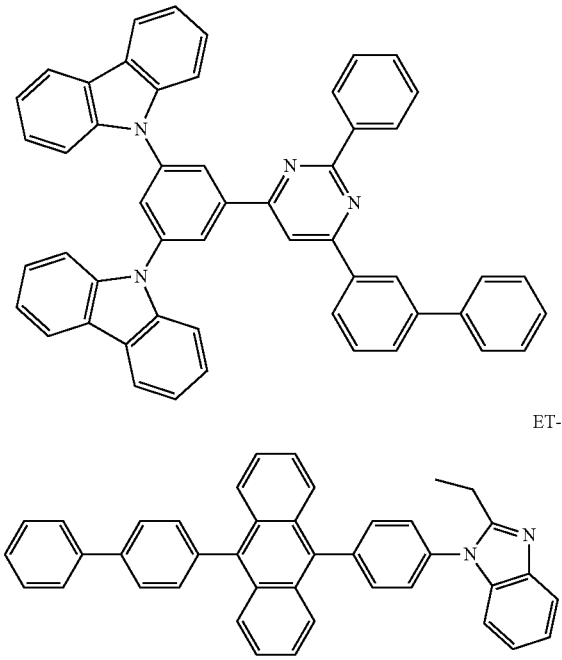

ET-1

ET-2

Each organic EL device was produced in the following manner and evaluated for EL device performance.

Production of Organic EL Device

Example 1

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode line was mounted to a substrate holder of a vacuum vapor deposition apparatus. First, the compound HI-1 was vapor-deposited on the surface having the transparent electrode line so as to cover the transparent electrode to form a hole injecting layer with a thickness of 5 nm.

On the hole injecting layer, the compound HT-1 was vapor-deposited to form a first hole transporting layer with a thickness of 80 nm.

On the first hole transporting layer, the compound Inv-1 was vapor-deposited to form a second hole transporting layer with a thickness of 10 nm.

Then, on the second hole transporting layer, the compound BH-1 (host material) and the compound BD-1 (dopant material) were vapor co-deposited to form a light emitting layer with a thickness of 25 nm. The concentration of the compound BD-1 in the light emitting layer was 4.0% by mass.

Then, on the light emitting layer, the compound ET-1 was vapor-deposited to form a first electron transporting layer with a thickness of 10 nm.

On the first electron transporting layer, the compound ET-2 was vapor-deposited to form a second electron transporting layer with a thickness of 15 nm, thereby forming a second electron transporting layer.

On the second electron transporting layer, LiF was vapor-deposited to form an electron injecting electrode (cathode) with a thickness of 1 nm.

Then, metallic Al was vapor-deposited on the electron injecting electrode to form a metallic cathode with a thickness of 80 nm.

The layered structure of the organic EL device of Example 1 is shown below:

ITO(130)/HI-1(5)/HT-1(80)/Compound Inv-1(10)/
   BH-1:BD-1=96:4(25)/ET-1(10)/ET-2(15)/LiF(1)/
   Al(80)

wherein the numerals in parenthesis is the thickness (nm) and the ratio of BH-1 and BD-1 is based on mass.

Examples 2 to 6

Each organic EL device was produced in the same manner as in Example 1 except for using each compound described in Table 1 as the second hole transporting layer material in place of the compound Inv-1.

Comparative Examples 1 to 4

Each organic EL device was produced in the same manner as in Example 1 except for using each compound described in Table 1 as the second hole transporting layer material in place of compound Inv-1.

Evaluation of Organic EL Device

Each of the organic EL devices produced above was measured for external quantum efficiency. The results are shown in Table 1.

Measurement of External Quantum Efficiency (EQE)

The organic EL device thus produced was operated by a constant direct current at room temperature at a current density of 10 mA/cm$^2$ to measure the luminance by a luminance meter (spectroradiometer CS-1000 manufactured by Minolta). The external quantum efficiency (%) was determined by the results.

TABLE 1

| | Second hole transporting layer material | External quantum efficiency (%) @10 mA/cm$^2$ |
|---|---|---|
| Example 1 | Compound Inv-1 | 9.6 |
| Example 2 | Compound Inv-2 | 9.9 |
| Example 3 | Compound Inv-3 | 10.0 |
| Example 4 | Compound Inv-4 | 9.9 |
| Example 5 | Compound Inv-5 | 9.6 |
| Example 6 | Compound Inv-12 | 9.9 |
| Comparative Example 1 | Compound Ref-1 | 8.7 |
| Comparative Example 2 | Compound Ref-2 | 9.2 |
| Comparative Example 3 | Compound Ref-3 | 9.1 |
| Comparative Example 4 | Compound Ref-4 | 8.6 |

As seen from the results of Table 1, the organic EL device comprising any of the compounds Inv-1 to Inv-5 and Inv-12 of formula (1) of the invention showed a high efficiency (high external quantum efficiency).

In contrast, the organic EL device comprising any of the compound Ref-1 described in Patent Literature 2 and any of the compounds Ref-2, Ref-3, and Ref-4 each described in Patent Literature 1 showed a poor efficiency (external quantum efficiency).

Upon comparing Examples 1 and 5 with Comparative Examples 1, 2, and 4, it can be found that a high efficiency is obtained when a 1-naphthyl group is bonded to the central nitrogen group via a p-biphenylylene linker.

Upon comparing Examples 1 to 6 with Comparative Example 3, it can be found that a high efficiency is obtained when Ar defined in formula (1) is present on the central nitrogen atom.
Compounds Synthesized in Synthesis Examples
Compound Inv-1
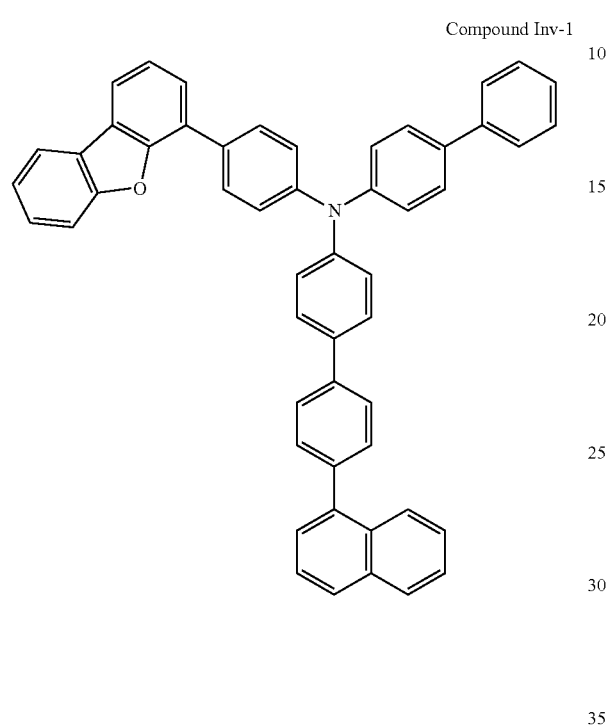
Compound Inv-2
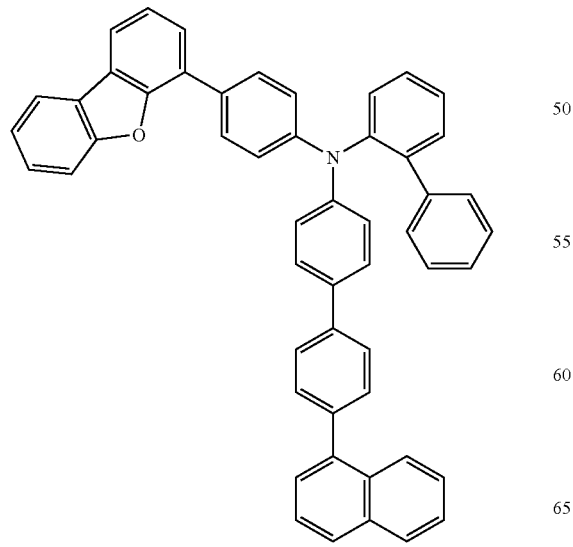
Compound Inv-3
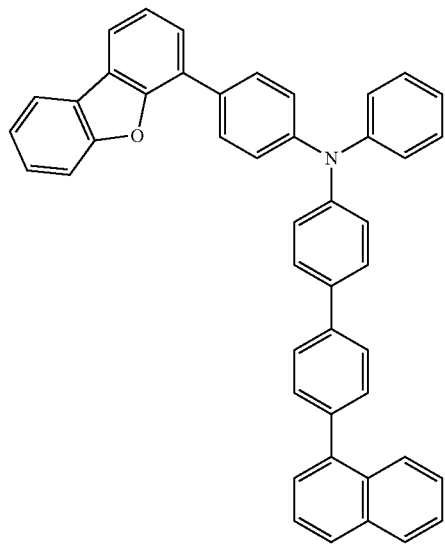
Compound Inv-4
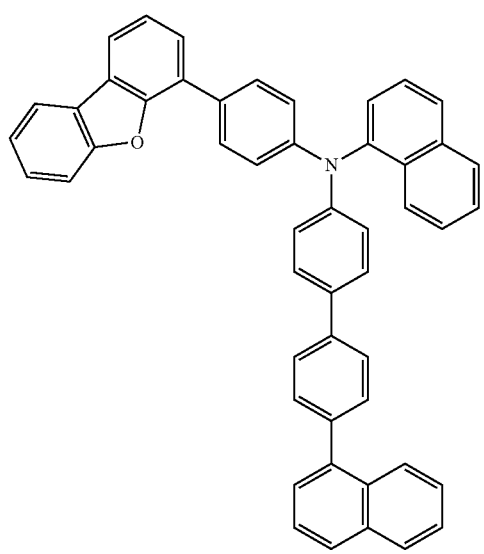

Compound Inv-5
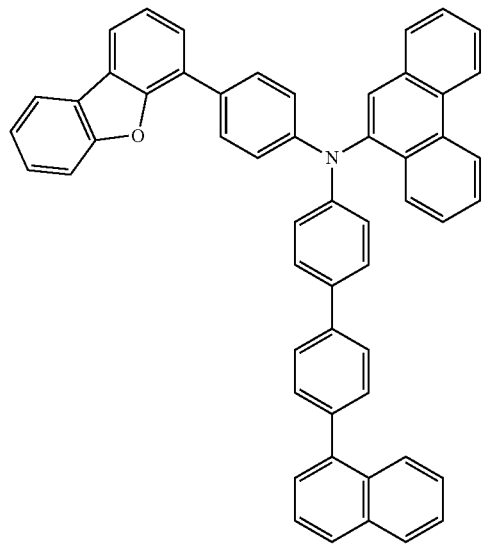
Compound Inv-7
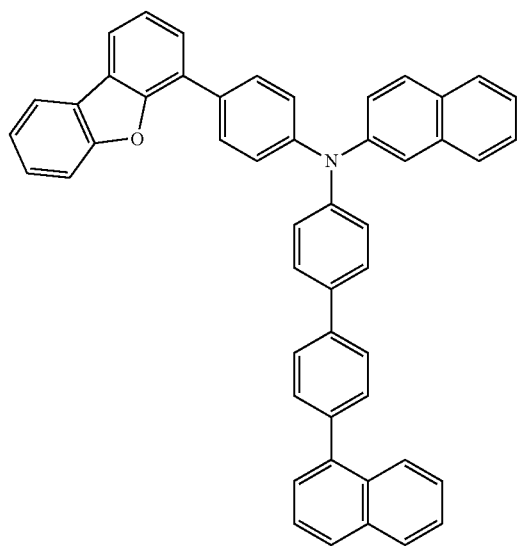
Compound Inv-6
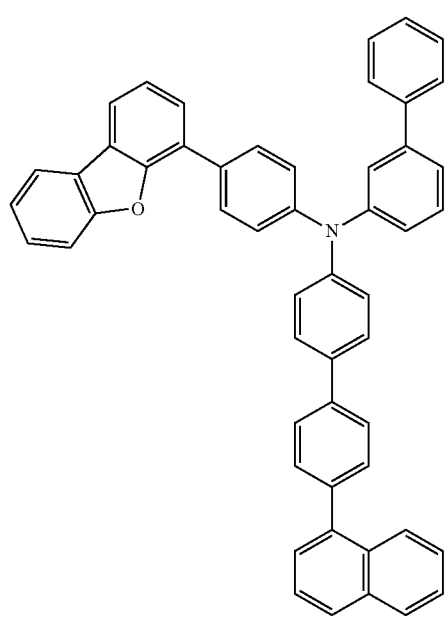
Compound Inv-8
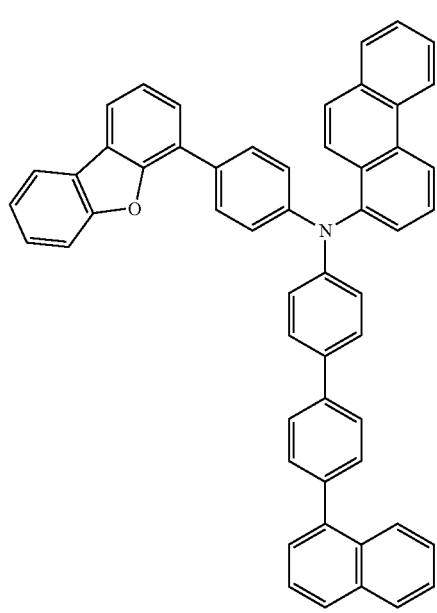

Compound Inv-9
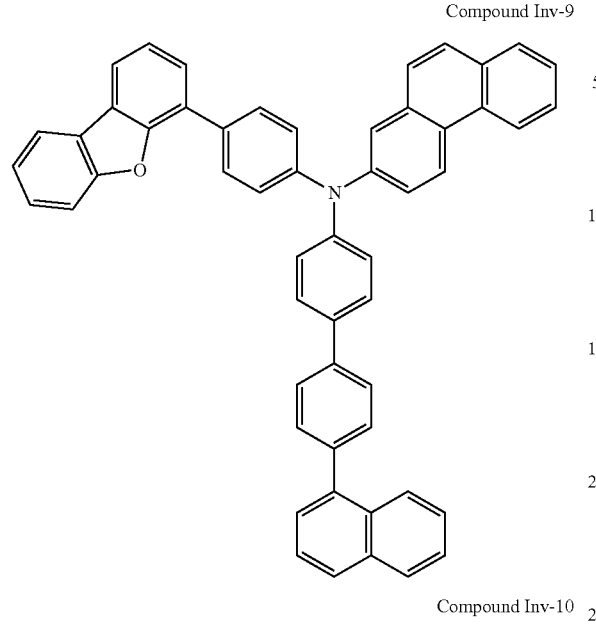
Compound Inv-11
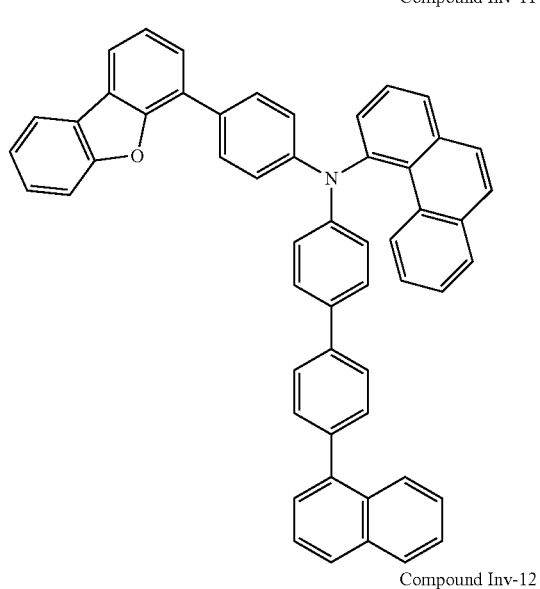
Compound Inv-10
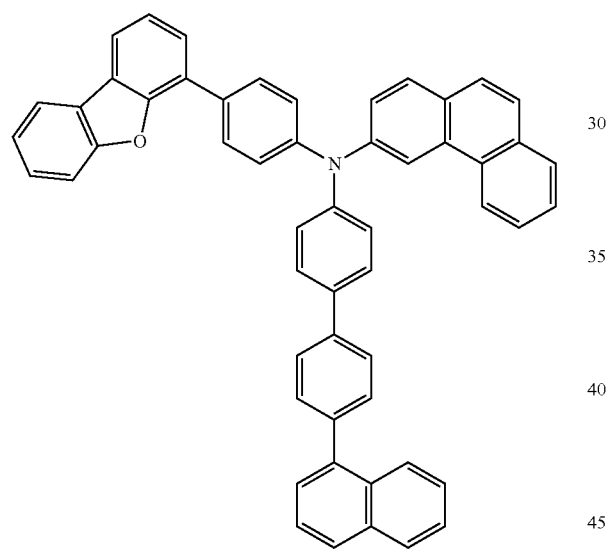
Compound Inv-12
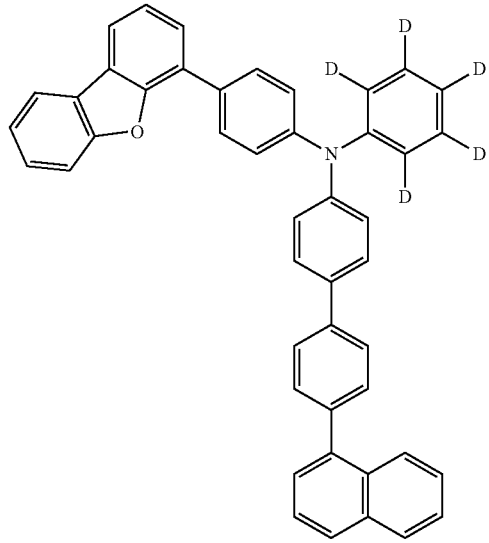
Synthesis Example 1: Synthesis of Compound Inv-1
Synthesis of Intermediate 1
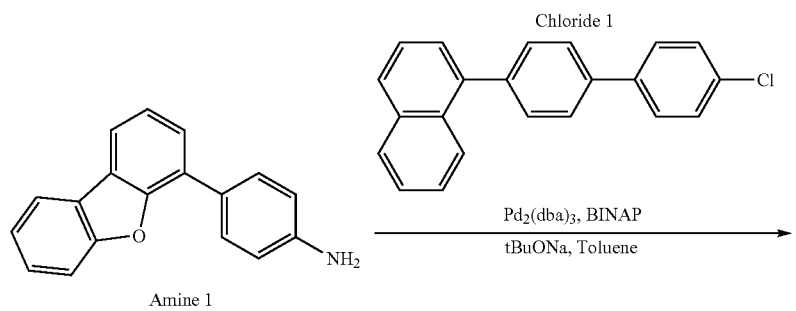

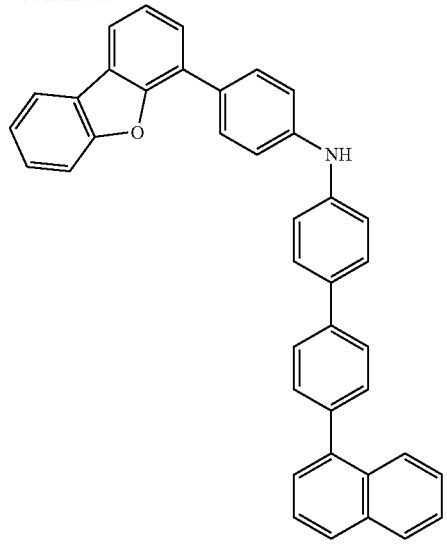

Intermediate 1

In an argon atmosphere, Amine 1 (20 mmol, 5.2 g), Chloride 1 (20 mmol, 6.3 g), tris(dibenzylideneacetone)dipalladium(0) (0.4 mmol, 366 mg), 2,2'-bis(diphenylphosphino)-1,1'-binaphthyl (0.4 mmol, 249 mg), sodium tert-butoxide (28 mmol, 2.7 g), and toluene (100 mL) were charged in a flask and stirred at 80° C. for 5 h under heating.

After cooling to room temperature (25° C.), the reaction solution was concentrated and the obtained residue was purified by a silica gel column chromatography to obtain a white solid (8.28 g, yield of 77%), which was identified as the intermediate 1 by LC-MS analysis.

Synthesis of Compound Inv-1

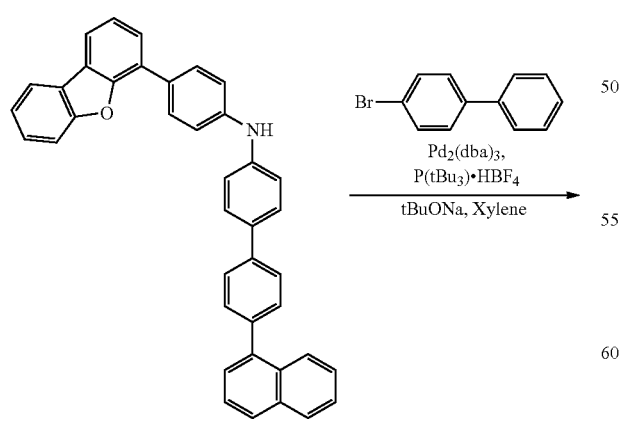

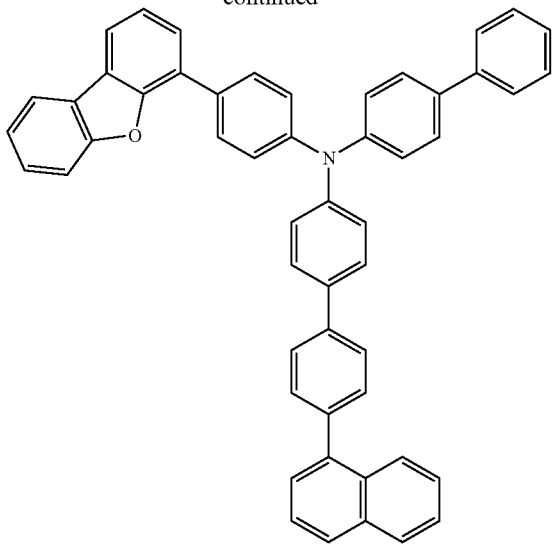

Compound Inv-1

In an argon atmosphere, the intermediate 1 (7 mmol, 3.8 g), 4-bromobiphenyl (7 mmol, 1.6 g), tris(dibenzylideneacetone)dipalladium(0) (0.14 mmol, 128 mg), tri-tert-butylphosphonium tetrafluoroborate (0.56 mmol, 162 mg), sodium tert-butoxide (9.8 mmol, 942 mg), and xylene (35 mL) were charged in a flask and refluxed for 4 h by stirring under heating.

After cooling to room temperature (25° C.), the reaction solution was concentrated and the obtained residue was purified by a silica gel column chromatography to obtain a white solid (4.0 g, yield of 83%), which was identified as the compound Inv-1 by LC-MS analysis.

Synthesis Example 2: Synthesis of Compound Inv-2

Synthesis Example 3: Synthesis of Compound Inv-3

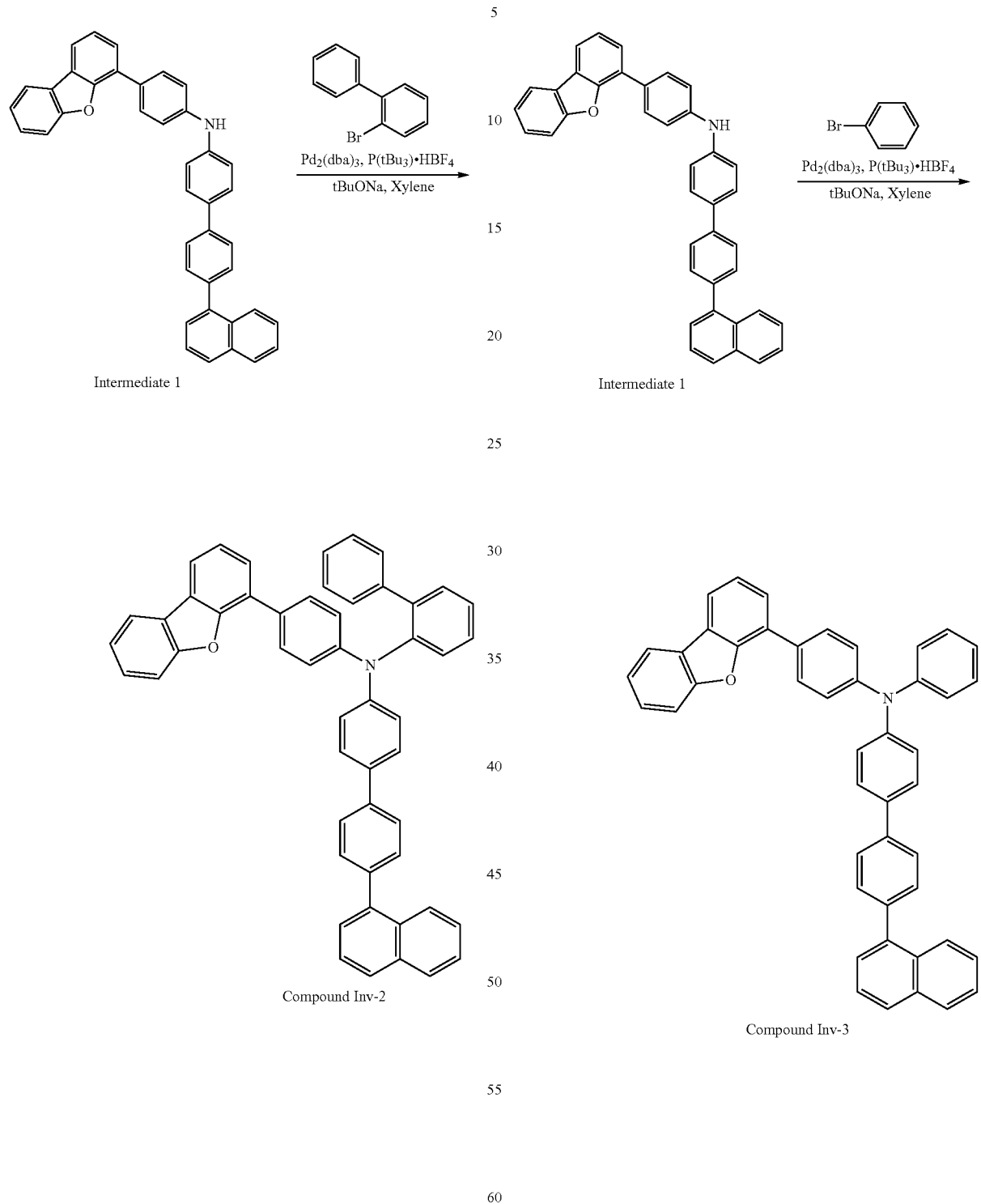

In the same manner as in Synthesis Example 1 except for using 2-bromobiphenyl in place of 4-bromobiphenyl, a white powder (3.8 g, yield of 78%) was obtained, which was identified as the compound Inv-2 by LC-MS analysis.

In the same manner as in Synthesis Example 1 except for using bromobenzene in place of 4-bromobiphenyl, a white powder (3.0 g, yield of 69%) was obtained, which was identified as the compound Inv-3 by LC-MS analysis.

Synthesis Example 4: Synthesis of Compound Inv-4

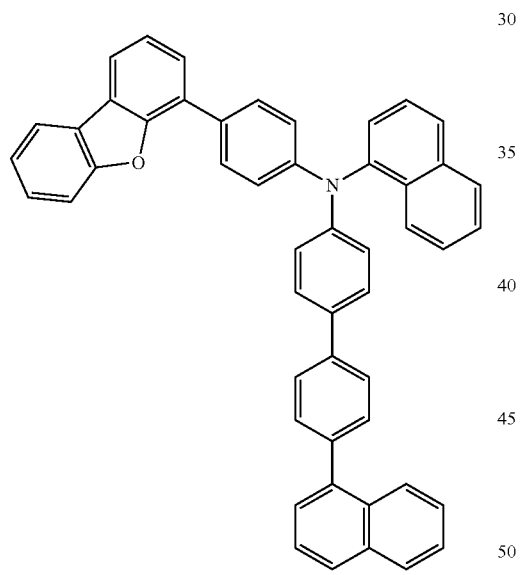

Compound Inv-4

Synthesis Example 5: Synthesis of Compound Inv-5

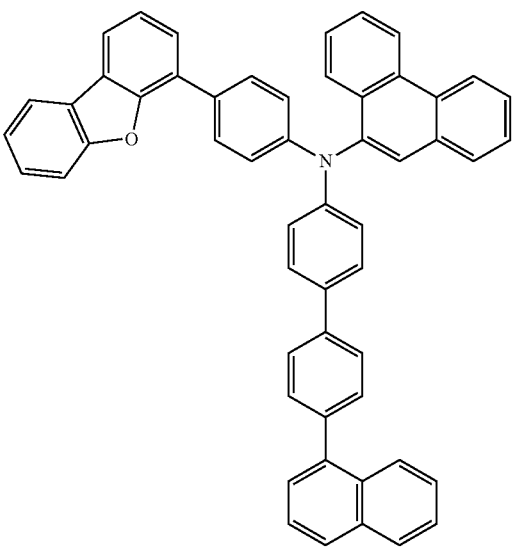

Compound Inv-5

In the same manner as in Synthesis Example 1 except for using 1-iodonaphthalene in place of 4-bromobiphenyl, a white powder (2.7 g, yield of 58%) was obtained, which was identified as the compound Inv-4 by LC-MS analysis.

In the same manner as in Synthesis Example 1 except for using 9-bromophenanthlene in place of 4-bromobiphenyl, a white powder (2.9 g, yield of 58%) was obtained, which was identified as the compound Inv-5 by LC-MS analysis.

Synthesis Example 6: Synthesis of Compound Inv-6

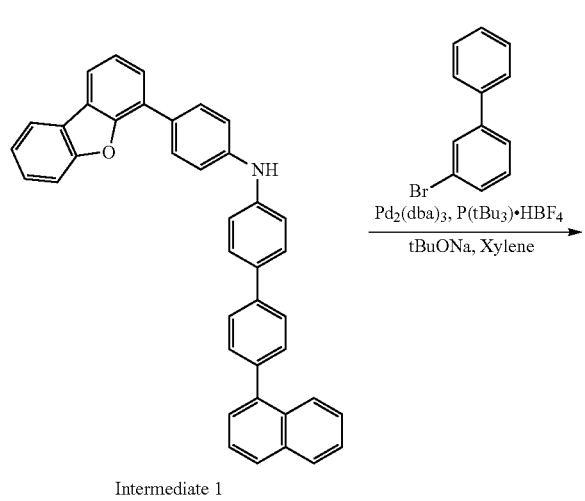

Intermediate 1

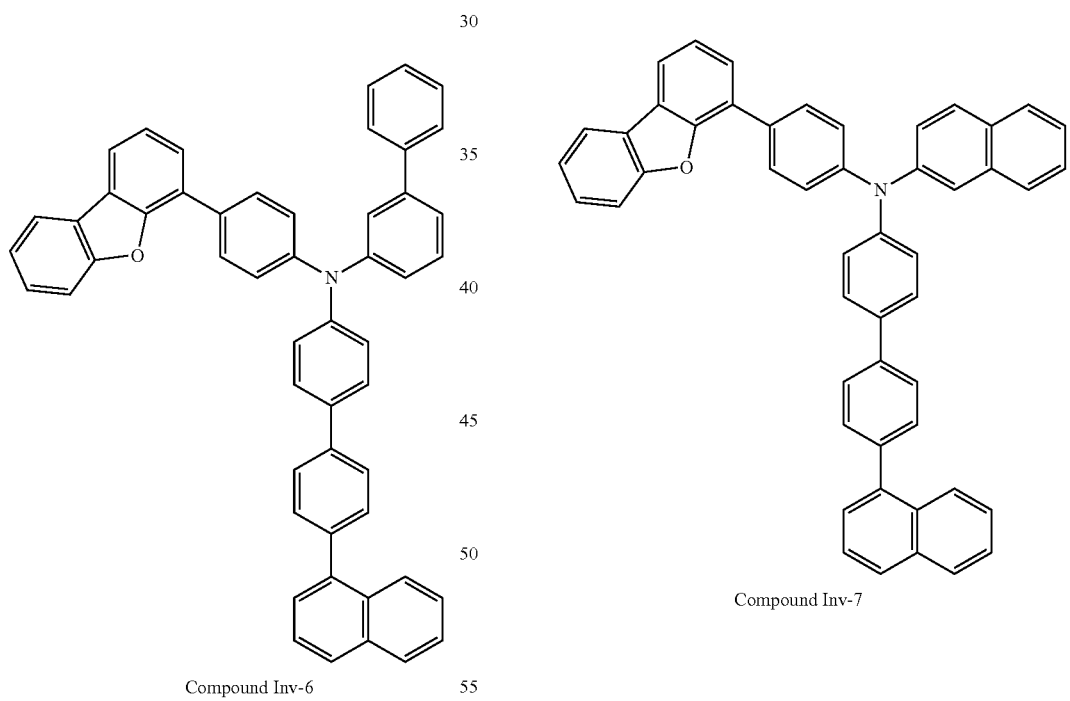

Compound Inv-6

Synthesis Example 7: Synthesis of Compound Inv-7

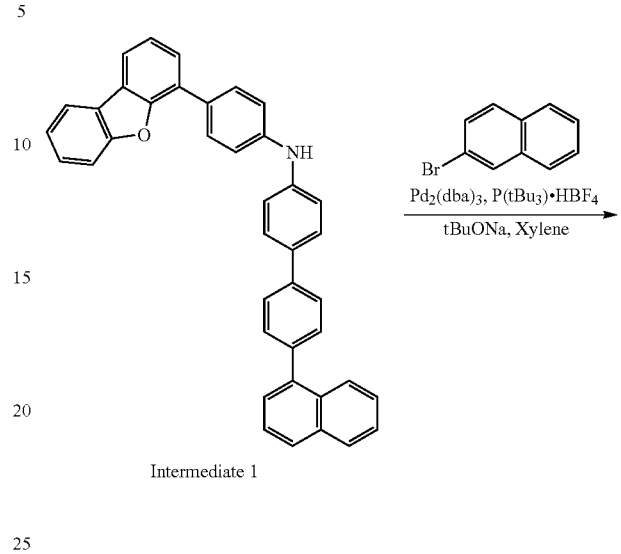

Intermediate 1

Compound Inv-7

In the same manner as in Synthesis Example 1 except for using 3-bromobiphenyl in place of 4-bromobiphenyl, a white powder (4.1 g, yield of 85%) was obtained, which was identified as the compound Inv-6 by LC-MS analysis.

In the same manner as in Synthesis Example 1 except for using 2-bromonaphthalene in place of 4-bromobiphenyl, a white powder (3.3 g, yield of 72%) was obtained, which was identified as the compound Inv-7 by LC-MS analysis.

Synthesis Example 8: Synthesis of Compound Inv-8

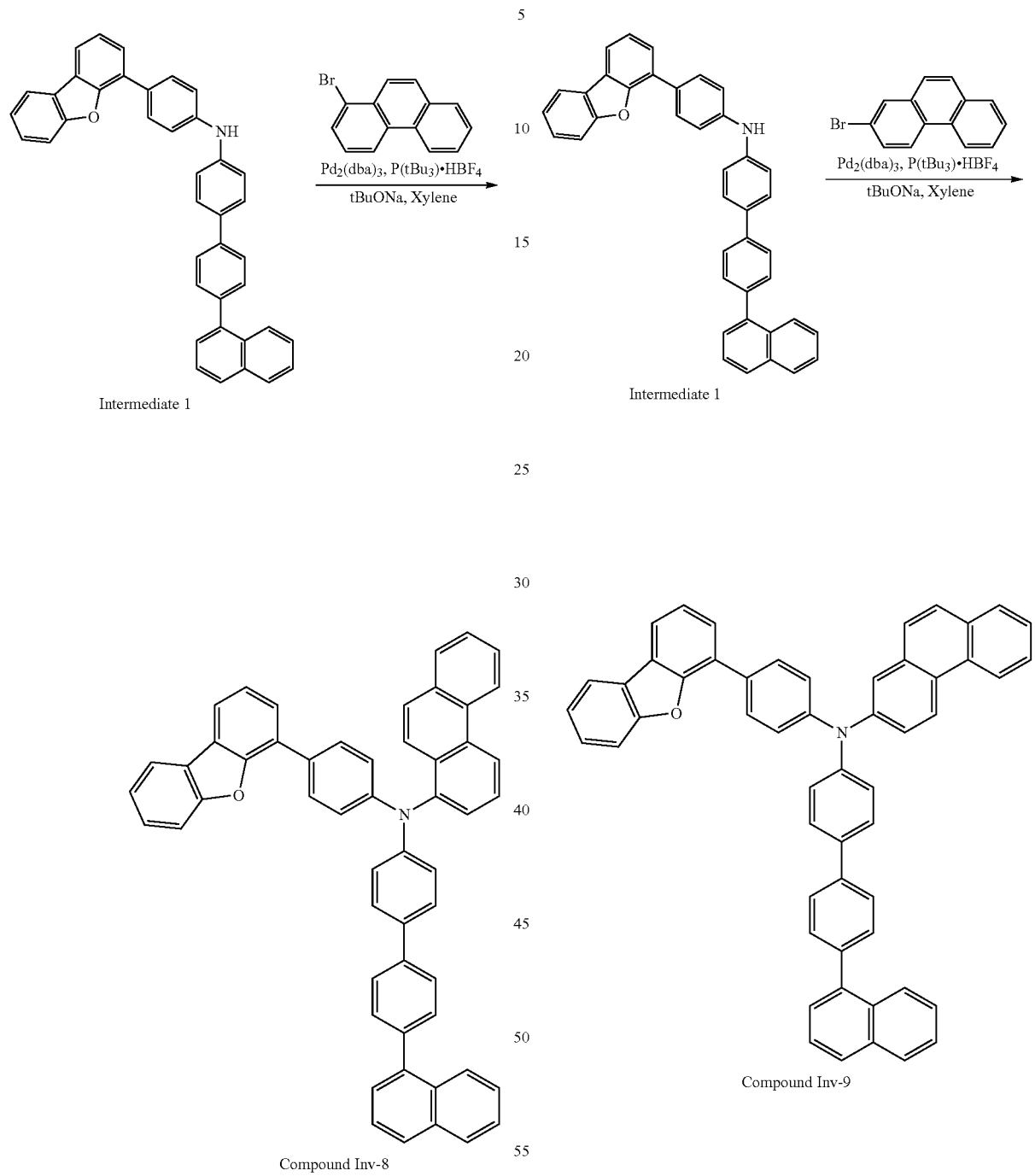

Synthesis Example 9: Synthesis of Compound Inv-9

In the same manner as in Synthesis Example 1 except for using 1-bromophenanthlene in place of 4-bromobiphenyl, a white powder (2.5 g, yield of 50%) was obtained, which was identified as the compound Inv-8 by LC-MS analysis.

In the same manner as in Synthesis Example 1 except for using 2-bromophenanthlene in place of 4-bromobiphenyl, a white powder (4.4 g, yield of 88%) was obtained, which was identified as the compound Inv-9 by LC-MS analysis.

Synthesis Example 10: Synthesis of Compound Inv-10

Synthesis Example 11: Synthesis of Compound Inv-11

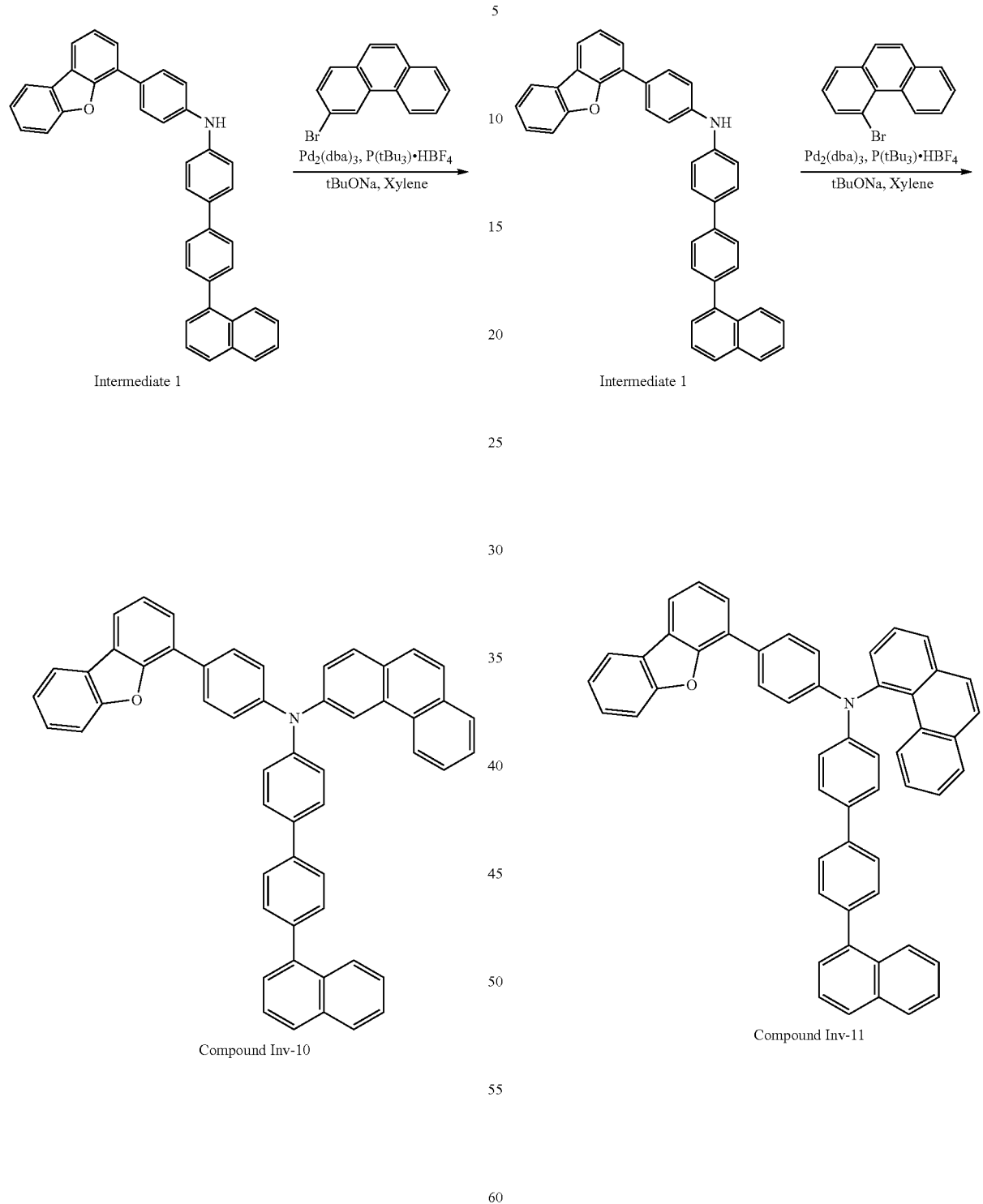

In the same manner as in Synthesis Example 1 except for using 3-bromophenanthlene in place of 4-bromobiphenyl, a white powder (3.5 g, yield of 71%) was obtained, which was identified as the compound Inv-10 by LC-MS analysis.

In the same manner as in Synthesis Example 1 except for using 4-bromophenanthlene in place of 4-bromobiphenyl, a white powder (2.1 g, yield of 43%) was obtained, which was identified as the compound Inv-11 by LC-MS analysis.

Synthesis Example 12: Synthesis of Compound Inv-12

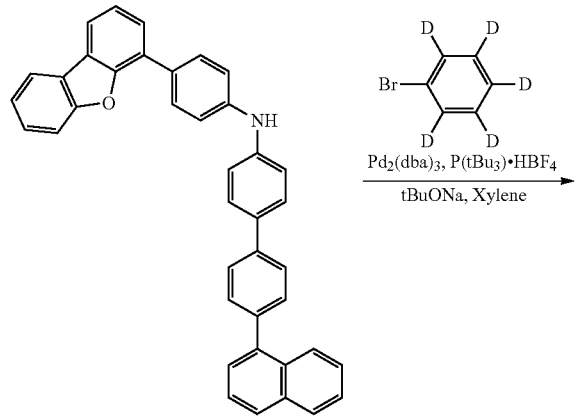

Intermediate 1

Compound Inv-12

In the same manner as in Synthesis Example 3 except for using bromobenzene-d5 in place of bromobenzene, a white powder (3.1 g, yield of 72%) was obtained, which was identified as the compound Inv-12 by LC-MS analysis.

REFERENCE SIGNS LIST

1, 11: Organic EL device
2: Substrate
3: Anode
4: Cathode
5: Light emitting layer
6: Hole transporting region (hole transporting layer)
6a: First hole transporting layer
6b: Second hole transporting layer
7: Electron transporting region (electron transporting layer)
7a: First electron transporting layer
7b: Second electron transporting layer
10, 20: Emission unit

The invention claimed is:
1. A compound represented by formula (3) or (13):

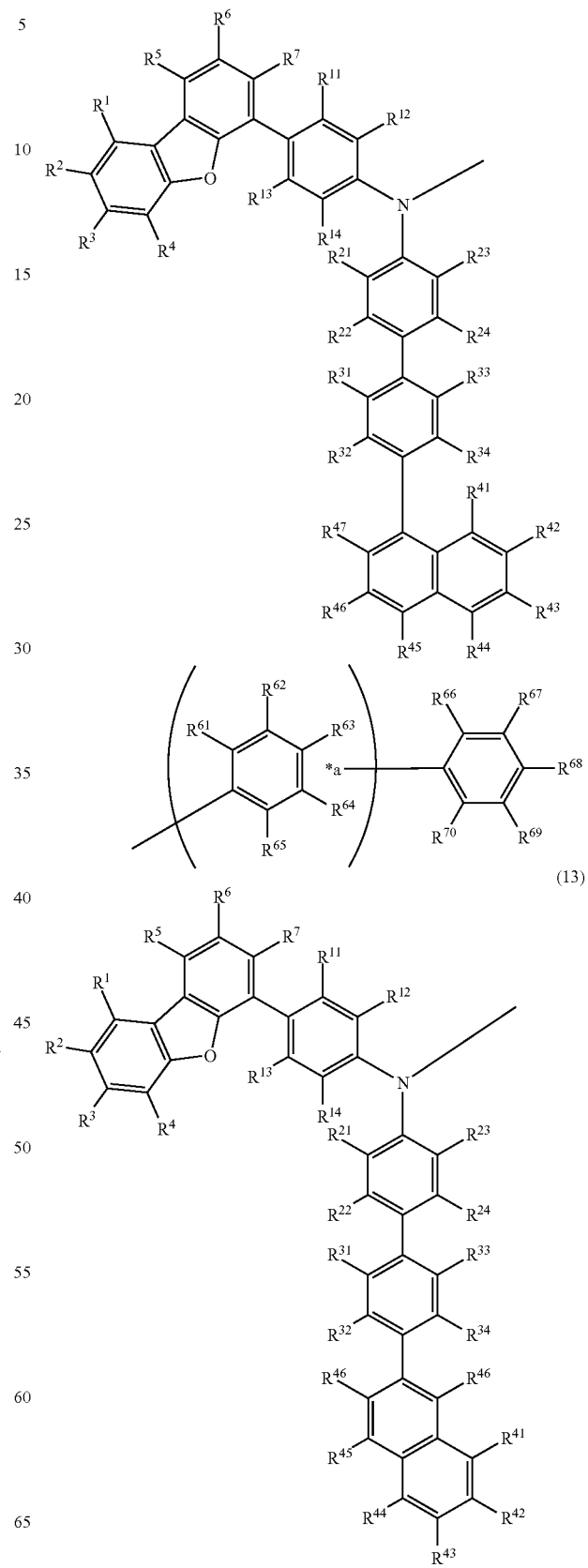

-continued

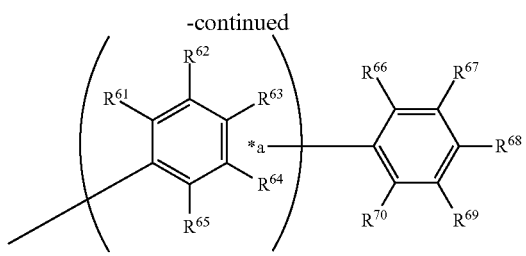

wherein:
  R¹ to R⁷ are each independently a hydrogen atom, a halogen atom, an alkyl group having 1 to 10 carbon atoms, or a cycloalkyl group having 3 to 6 ring carbon atoms;
  R¹¹ to R¹⁴ are each independently a hydrogen atom, a halogen atom, an alkyl group having 1 to 10 carbon atoms, or a cycloalkyl group having 3 to 6 ring carbon atoms;
  R²¹ to R²⁴ are each independently a hydrogen atom, a halogen atom, an alkyl group having 1 to 10 carbon atoms, or a cycloalkyl group having 3 to 6 ring carbon atoms;
  R³¹ to R³⁴ are each independently a hydrogen atom, a halogen atom, an alkyl group having 1 to 10 carbon atoms, or a cycloalkyl group having 3 to 6 ring carbon atoms;
  R⁴¹ to R⁴⁸ are each independently a hydrogen atom, a halogen atom, an alkyl group having 1 to 10 carbon atoms, or a cycloalkyl group having 3 to 6 ring carbon atoms, provided that one selected from R⁴⁷ and R⁴⁸ is a single bond bonded to *1;
  one selected from R⁶¹ to R⁶⁵ is a single bond bonded to *a, and the others of R⁶¹ to R⁶⁵ and R⁶⁶ to R⁷⁰ are each independently a hydrogen atom, a halogen atom, an alkyl group having 1 to 10 carbon atoms, or a cycloalkyl group having 3 to 6 ring carbon atoms;
  an optional substituent for the phenyl group, the biphenylyl group, the naphthyl group, and the phenanthryl group is independently a halogen atom, an alkyl group having 1 to 10 carbon atoms, or a cycloalkyl group having 3 to 6 ring carbon atoms;
  adjacent two selected from R¹ to R⁷, R¹¹ to R¹⁴, R²¹ to R²⁴, R³¹ to R³⁴, and R⁴¹ to R⁴⁸ not the single bond bonded to *1 are not bonded to each other thereby failing to form a ring structure; and
  if the phenyl group, the biphenylyl group, the naphthyl group, or the phenanthryl group has adjacent two optional substituents, the adjacent two optional substituents are not bonded to each other thereby failing to form a ring.

2. The compound according to claim 1, wherein the halogen atom for R¹ to R⁷, R¹¹ to R¹⁴, R²¹ to R²⁴, R³¹ to R³⁴, and R⁴¹ to R⁴⁸ not the single bond bonded to *1 are each independently selected from an iodine atom, a bromine atom, a chlorine atom, and a fluorine atom.

3. The compound according to claim 1, wherein the alkyl group having 1 to 10 carbon atoms for R¹ to R⁷, R¹¹ to R¹⁴, R²¹ to R²⁴, R³¹ to R³⁴ and R⁴¹ to R⁴⁸ not the single bond bonded to *1 are each independently selected from a methyl group, an ethyl group, a n-propyl group, a sec-propyl group, an isopropyl group, a n-butyl group, a sec-butyl group, an isobutyl group, and a t-butyl group.

4. The compound according to claim 1, wherein the cycloalkyl group having 3 to 6 ring carbon atoms for R¹ to R⁷, R¹¹ to R¹⁴, R²¹ to R²⁴, R³¹ to R³⁴, and R⁴¹ to R⁴⁸ not the single bond bonded to *1 are each independently selected from a cyclopropyl group, a cyclobutyl group, a cyclopentyl group, and a cyclohexyl group.

5. The compound according to claim 1, wherein R¹ to R⁷, to R¹¹ to R¹⁴, R²¹ to R²⁴, R³¹ to R³⁴, and R⁴¹ to R⁴⁸ not the single bond bonded to *1 are all hydrogen atoms.

6. The compound according to claim 1, wherein the compound is represented by any of the following formulae:

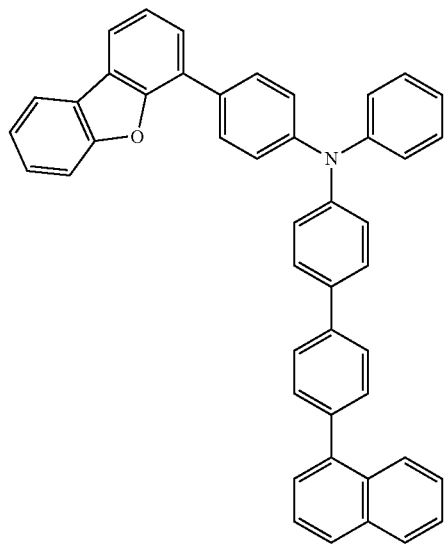

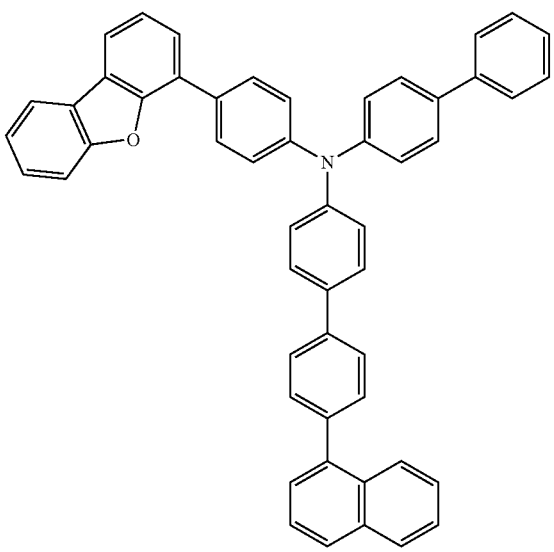

141
-continued
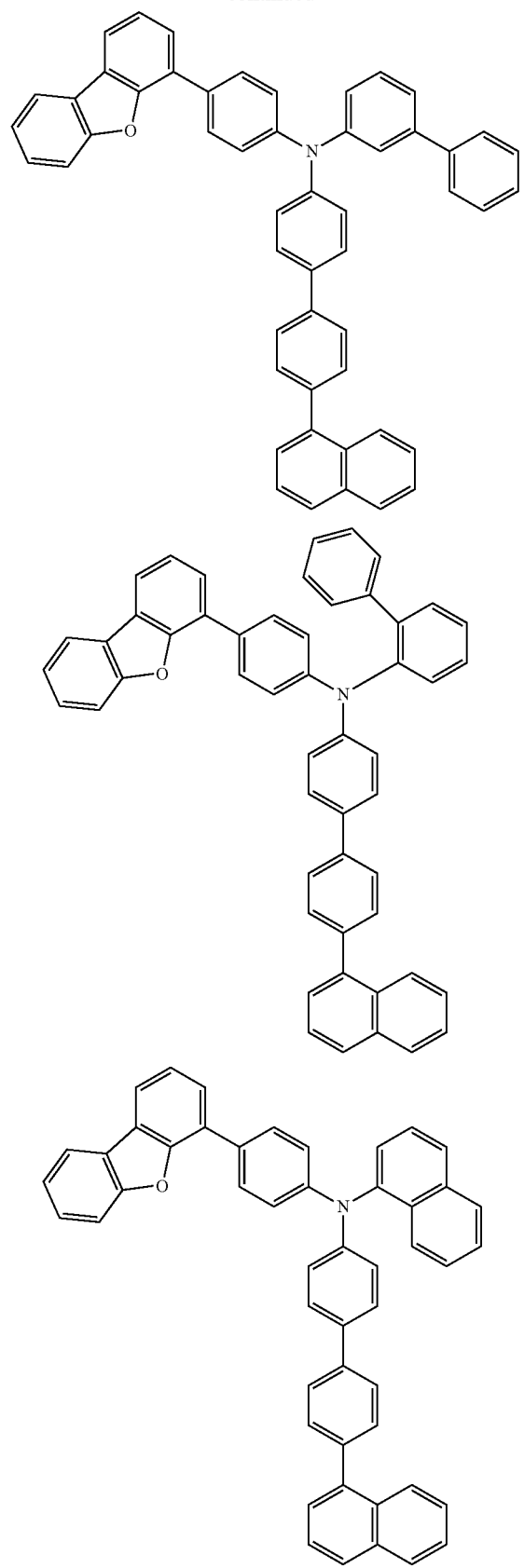
142
-continued
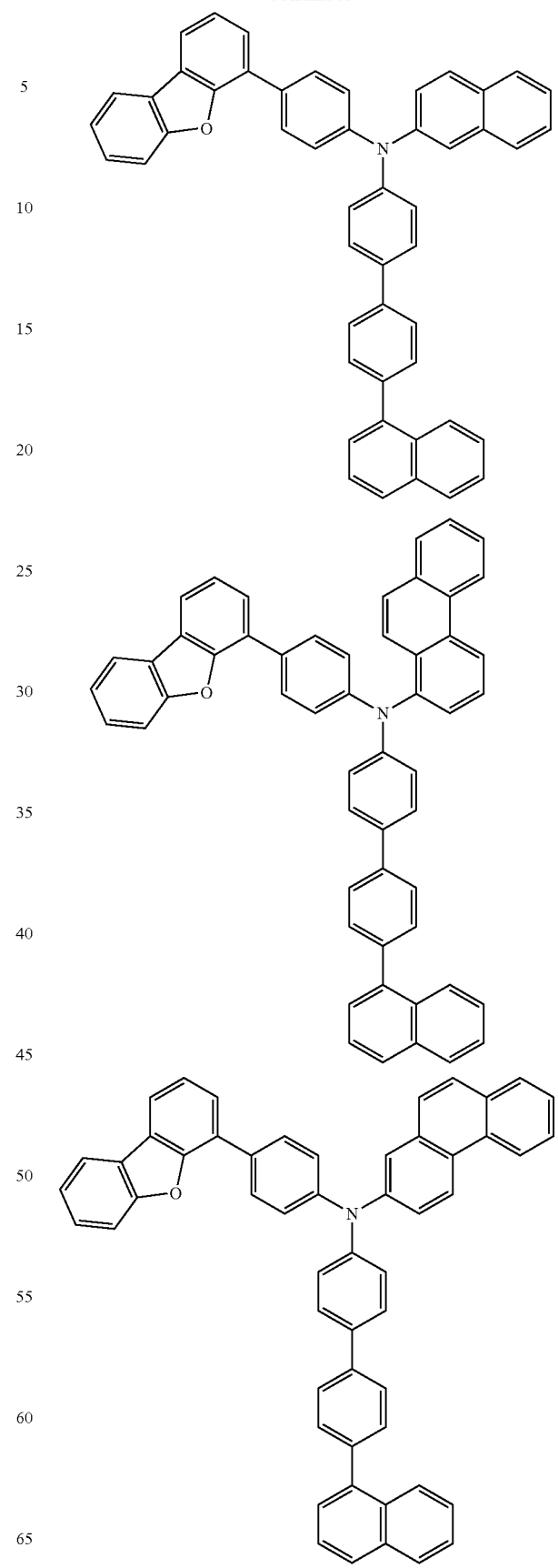

143
-continued
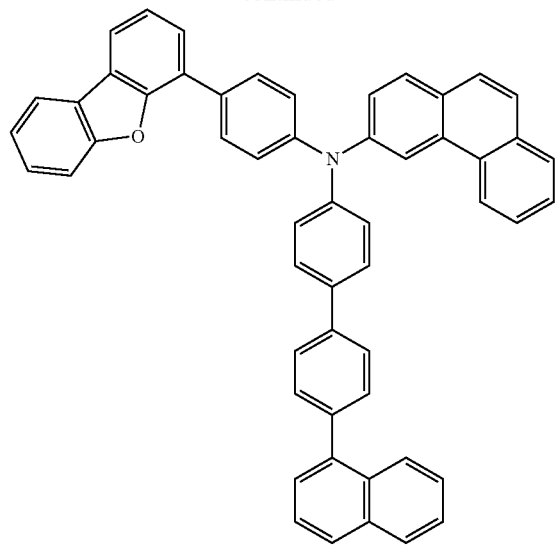
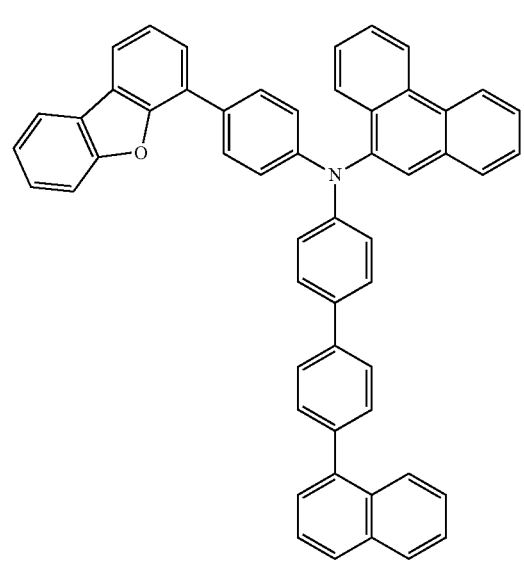
144
-continued
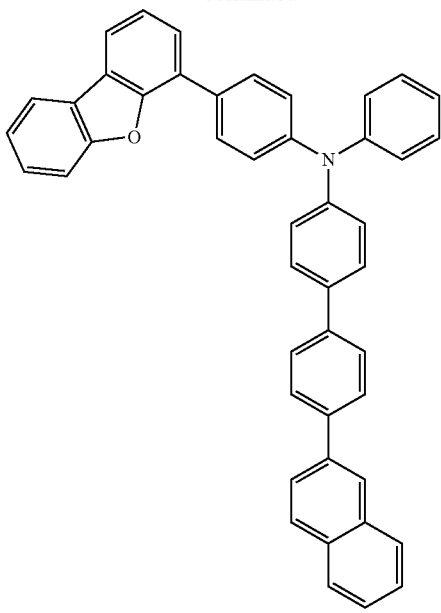
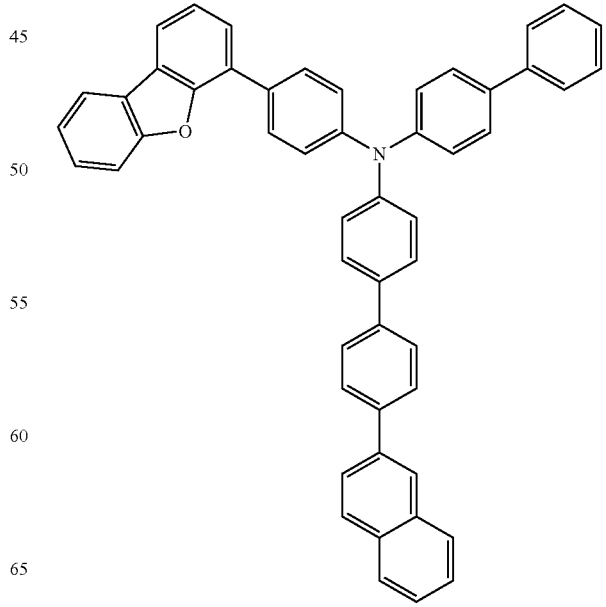

145
-continued
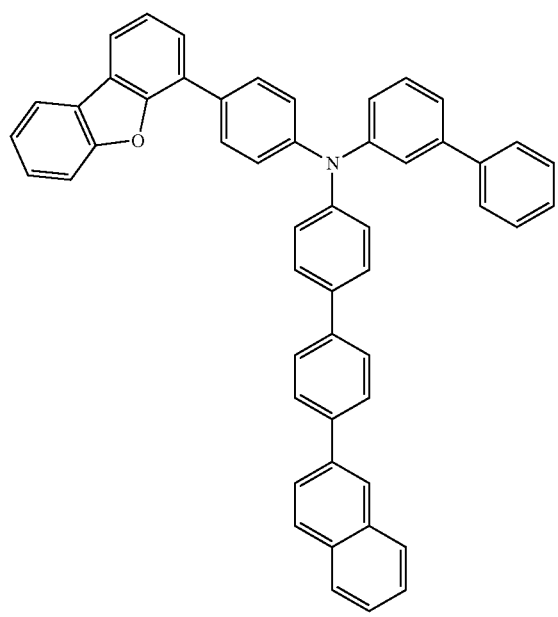
146
-continued
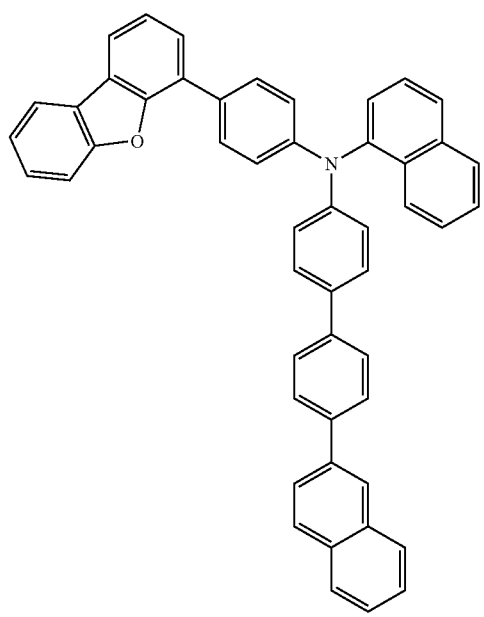
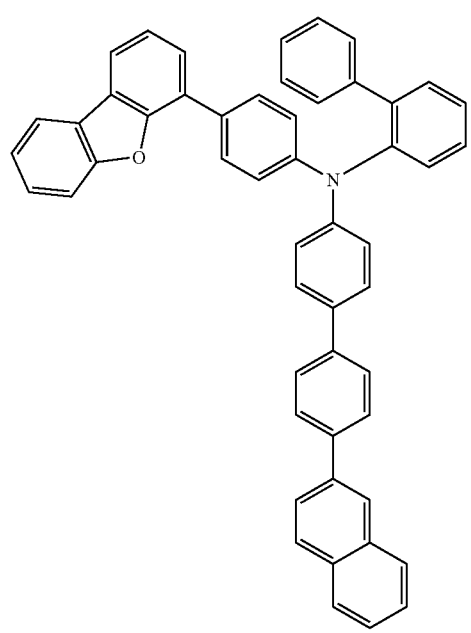

147
-continued
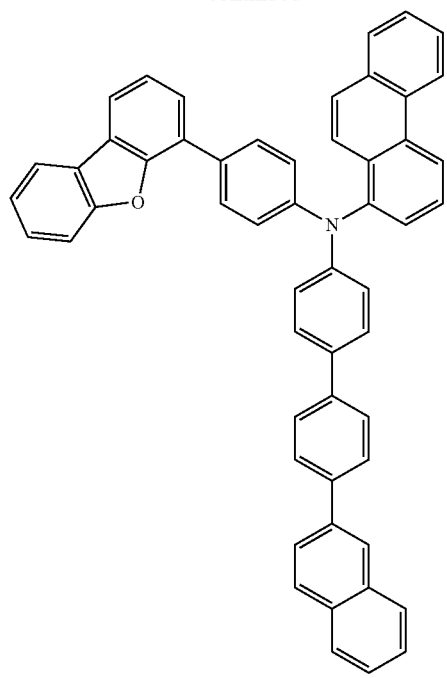
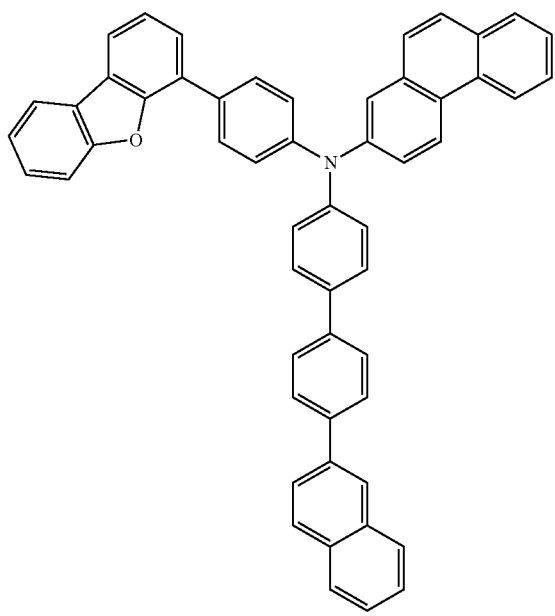
148
-continued
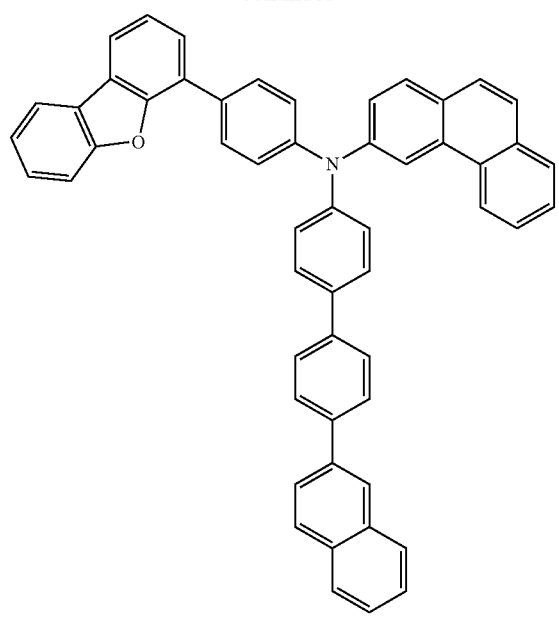
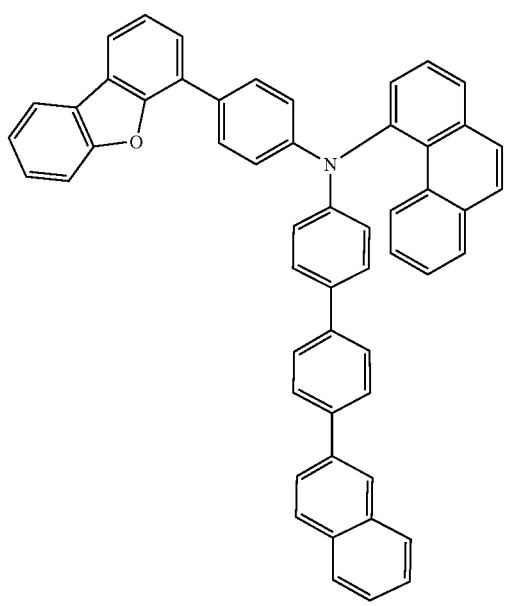

-continued

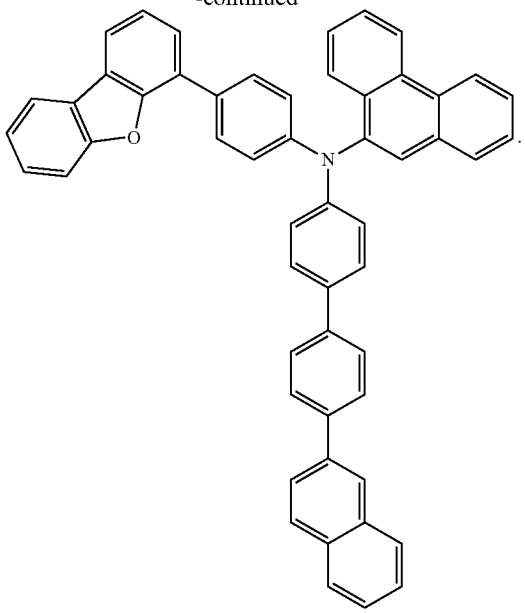

7. A material for organic electroluminescence device, comprising the compound according to claim 1.

8. An organic electroluminescence device comprising a cathode, an anode, and an organic layer between the cathode and the anode, wherein:
the organic layer comprises a light emitting layer; and
at least one layer of the organic layer comprises the compound according to claim 1.

9. The organic electroluminescence device according to claim 8, wherein:
the organic layer comprises a hole transporting region between the anode and the light emitting layer; and
the hole transporting region comprises the compound.

10. The organic electroluminescence device according to claim 9, wherein:
the hole transporting region comprises a first hole transporting layer on anode side and a second hole transporting layer on cathode side; and
the first hole transporting layer, the second hole transporting layer; or both thereof comprise the compound.

11. The organic electroluminescence device according to claim 10, wherein the first hole transporting layer comprises the compound.

12. The organic electroluminescence device according to claim 10, wherein the second hole transporting layer comprises the compound.

13. The organic electroluminescence device according to claim 8, wherein the light emitting layer comprises a fluorescent dopant material.

14. The organic electroluminescence device according to claim 8, wherein the light emitting layer comprises a phosphorescent dopant material.

15. An electronic device comprising the organic electroluminescence device according to claim 8.

* * * * *